United States Patent
Chang et al.

(10) Patent No.: US 10,993,986 B2
(45) Date of Patent: May 4, 2021

(54) PHARMACEUTICAL CONSTRUCTS WITH ENHANCED BINDING AFFINITY WITH ALBUMIN

(71) Applicant: Immunwork Inc., Taipei (TW)

(72) Inventors: Tse-Wen Chang, Taipei (TW);
Hsing-Mao Chu, Taipei (TW);
Chien-Jen Lin, Taipei (TW)

(73) Assignee: IMMUNWORK INC., Taipei (TW)

( * ) Notice: Subject to any disclaimer, the term of this patent is extended or adjusted under 35 U.S.C. 154(b) by 0 days.

(21) Appl. No.: 16/823,358

(22) Filed: Mar. 19, 2020

(65) Prior Publication Data

US 2020/0222498 A1    Jul. 16, 2020

Related U.S. Application Data

(63) Continuation of application No. PCT/CN2018/106515, filed on Sep. 19, 2018.

(30) Foreign Application Priority Data

Sep. 19, 2017 (WO) ................ PCT/CN2017/102242

(51) Int. Cl.
| | | |
|---|---|---|
| *A61K 47/00* | (2006.01) | |
| *A61K 38/12* | (2006.01) | |
| *A61K 47/54* | (2017.01) | |
| *A61K 47/55* | (2017.01) | |

(52) U.S. Cl.
CPC ............ *A61K 38/12* (2013.01); *A61K 47/542* (2017.08); *A61K 47/545* (2017.08); *A61K 47/55* (2017.08)

(58) Field of Classification Search
CPC .... A61K 47/542; A61K 38/12; A61K 47/545; A61K 47/55; A61K 38/08; A61K 38/31; A61K 38/38; C07K 14/655; C07K 14/605; C07K 14/76; C07K 7/06
See application file for complete search history.

(56) References Cited

U.S. PATENT DOCUMENTS

2015/0246958 A1 * 9/2015 Han ........................ C07K 14/62
514/1.3
2016/0271227 A1 * 9/2016 Schneider ............... A61K 47/60

FOREIGN PATENT DOCUMENTS

WO    WO-2016112870 A1 *  7/2016 ........... A61K 31/739
WO    WO-2016184426 A1 * 11/2016 ............... C07K 7/08

OTHER PUBLICATIONS

Zorzi et al. Acylated heptapeptide binds albumin with high affinity and application as tag furnishes long-acting peptidesNat. Commun 8, 16092 (2017). (Year: 2017).*

* cited by examiner

*Primary Examiner* — James H Alstrum-Acevedo
*Assistant Examiner* — Mercy H Sabila

(57) ABSTRACT

The present disclosure provides various molecular constructs having a plurality of fatty acids and a functional element. Methods for treating various diseases using such molecular constructs are also disclosed.

15 Claims, 17 Drawing Sheets

Specification includes a Sequence Listing.

***P<0.001, student t test

```
                       SEQUENCE LISTING

<160> NUMBER OF SEQ ID NOS: 8

<210> SEQ ID NO 1
<211> LENGTH: 31
<212> TYPE: PRT
<213> ORGANISM: Artificial Sequence
<220> FEATURE:
<223> OTHER INFORMATION: Synthesized

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: 2
<223> OTHER INFORMATION: Aib

<400> SEQUENCE: 2

His Xaa Glu Gly Thr Phe Thr Ser Asp Val Ser Ser Tyr Leu Glu Gly
1               5                   10                  15

Gln Ala Ala Lys Leu Glu Phe Ile Ala Trp Leu Val Arg Gly Arg Gly
            20                  25                  30

<210> SEQ ID NO 3
<211> LENGTH: 14
<212> TYPE: PRT
<213> ORGANISM: Artificial Sequence
<220> FEATURE:
<223> OTHER INFORMATION: Synthesized

<400> SEQUENCE: 3

Cys Ser Gly Gly Gly Gly Phe Cys Phe Trp Lys Thr Cys Thr
```

```
1               5                   10
```

<210> SEQ ID NO 4
<211> LENGTH: 19
<212> TYPE: PRT
<213> ORGANISM: Artificial Sequence
<220> FEATURE:
<223> OTHER INFORMATION: Synthesized

<400> SEQUENCE: 4

```
Cys Gly Gly Ser Gly Gly Ser Gly Gly Ser Lys Gly Ser Gly Ser Lys
1               5                   10                  15

Gly Ser Lys
```

<210> SEQ ID NO 5
<211> LENGTH: 18
<212> TYPE: PRT
<213> ORGANISM: Artificial Sequence
<220> FEATURE:
<223> OTHER INFORMATION: Synthesized

<400> SEQUENCE: 5

```
Gly Ser Gly Ser Gly Gly Ser Lys Gly Ser Gly Ser Lys Gly Ser Gly
1               5                   10                  15

Ser Lys
```

<210> SEQ ID NO 6
<211> LENGTH: 14
<212> TYPE: PRT
<213> ORGANISM: Artificial Sequence
<220> FEATURE:
<223> OTHER INFORMATION: Synthesized

<400> SEQUENCE: 6

```
Glu Gly Ser Gly Ser Gly Phe Cys Phe Trp Lys Thr Cys Thr
1               5                   10
```

<210> SEQ ID NO 7
<211> LENGTH: 4
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is a PEGylated amino acid with four EG
      units Xaa is coupled with an alkynylpropionyl group
<220> FEATURE:
<223> OTHER INFORMATION: Synthesized
<220> FEATURE:
<221> NAME/KEY: MOD_RES
<222> LOCATION: 3
<223> OTHER INFORMATION: Xaa is a PEGylated amino acid with four EG
      units
<220> FEATURE:
<221> NAME/KEY: MOD_RES
<222> LOCATION: 4
<223> OTHER INFORMATION: esterification

<400> SEQUENCE: 7

```
Xaa Lys Xaa Lys
1
```

<210> SEQ ID NO 8
<211> LENGTH: 38
<212> TYPE: PRT
<213> ORGANISM: Artificial Sequence
<220> FEATURE:
<221> NAME/KEY: MOD_RES

```
<222> LOCATION: 1
<223> OTHER INFORMATION: Xaa is a PEGylated amino acid with two EG units
      Xaa is coupled with an alkynylpropionyl group
<220> FEATURE:
<223> OTHER INFORMATION: Synthesized
<220> FEATURE:
<221> NAME/KEY: MOD_RES
<222> LOCATION: 3
<223> OTHER INFORMATION: Xaa is a PEGylated amino acid with two EG units
<220> FEATURE:
<221> NAME/KEY: MOD_RES
<222> LOCATION: 4
<223> OTHER INFORMATION: esterification

<400> SEQUENCE: 8

Gly Leu Ala Gly Gly Ser Ala Gln Ser Gln Arg Ala Pro Asp Arg Val
1               5                   10                  15

Leu Cys His Ser Gly Gln Gln Gln Gly Leu Pro Arg Ala Ala Gly Gly
            20                  25                  30

Ser Val Pro His Pro Arg
            35
```

PHARMACEUTICAL CONSTRUCTS WITH ENHANCED BINDING AFFINITY WITH ALBUMIN

CROSS-REFERENCE TO RELATED APPLICATION

This application is a continuation application of International Patent Application No. PCT/CN2018/106515, filed Sep. 19, 2018, designating the United States and claiming priority to International Patent Application No. PCT/CN2017/102242, filed Sep. 19, 2017, and the entire content of both applications is incorporated herein by reference.

BACKGROUND OF THE INVENTION

1. Field of the Invention

The invention pertains to novel pharmaceutical constructs, specifically, pharmaceutical constructs modified with two or more fatty acid or dioic fatty acid molecules, thereby increasing their binding affinity to the albumin and improving the serum life-time thereof.

2. Description of the Related Art

The development of pharmaceuticals with multiple functions has become a much sought-after research area. For example, the multi-arm linker units, as disclosed in published International Patent Application No. WO2016112870 (A1), and its related applications represent major chemical entities for the construction of molecules with two or more functional parts. However, the WO2016112870 publication employs amino acids with build-in functional groups such as tetrazine, cyclooctene, and cyclooctyne, for click chemistry reaction; yet these amino acids are not available for incorporation in the peptide core during solid-phase peptide synthesis. Moreover, according to the WO2016112870 publication, the coupling arm with tetrazine, cyclooctene, or cyclooctyne group is built in via a reaction between the thiol group of a cysteine residue and a maleimide group of a heterobifunctional linker that comprises the maleimide group at one terminus and a tetrazine, cyclooctene, or cyclooctyne group at the other terminus. The product of thiol and maleimide reaction is known to be unstable, undergoing a reverse reaction or exchange reaction with adjacent thiol-group containing molecules, which might affect the stability of the conjugated linkers in storage. Furthermore, when the peptide core contains a cysteine residue, as taught in the WO2016112870 publication, it is not feasible to carry out the continual solid-phase synthesis (branching of the peptide) of linking arms with a functional group that may react with the thiol group on a peptide core. Additionally, the alpha-amino group at the N-terminal of the peptide core requires an extra step of blocking, thereby reducing yield and purity of the peptide core or the linker unit.

Furthermore, it is desirable to lengthen the half-lives of drugs in certain clinical conditions, so that less frequent administrations of the drug are required and less fluctuation of the drug concentrations in the blood occurs, which can translate to decreased costs and enhanced adherence to medication.

Several methodologies have been employed to increase the half-lives of drugs. These can be achieved by structural alteration, such as amino acid residue mutations, of the peptide or protein drug molecules without resorting to special formulation or conjugation with other chemical moieties. For example, making amino acid substitutions to reduce sensitivity to proteases, change isoelectric points, and increase lipid solubility may enhance the half-lives of certain drugs. The genetically altered tissue plasminogen activator, tenecteplase, has several site-specific mutations and is resistant to plasminogen activator inhibitor and hence achieves longer half-life than the wild-type activase. A marketed version of human insulin (insulin glargine), which has an asparagine residue substituted for glycine and reduced solubility in neutral pH, aggregates when injected subcutaneous in a patient. The aggregated insulin then dissolves slowly and diffuses into the blood circulation and hence achieves a longer half-life than that of regular (wild-type) insulin.

Some drugs are mixed with matrix-forming substances, such as poly-lactide-co-glycolide, or packed into liposomes or other types of microspheres/nanoparticles. When the formulated drugs are administered into a patient, they achieve slow release kinetics. Several chemotherapeutic drugs, such as taxol and doxorubicin, and hormones, such as somatostatin analogue, (octreotide acetate) and gonadotropin releasing hormone analogue (leuprorelin), are formulated with microspheres as depots for long-term slow release.

Many protein drugs, such as interferon-$\alpha$, interferon-$\beta$, erythropoietin, human growth hormone, granulocyte colony stimulating factor, adenosine deaminase, and asparaginase, are modified with polyethylene glycol (PEG), to improve pharmacokinetic activity and stability, and reduce immunogenicity. One drawback in using PEG for modification is the heterogeneity of the conjugated products. The long-chain PEG can also wrap around a protein molecule and thus inhibit the activity of the protein drug. Long-chain PEG also resists to degradation and accumulates in patients.

Another methodology to improve the pharmacokinetic properties of a protein drug is to fuse the protein with the CH2-CH3 domains of the Fc portion of an IgG. The protein drug and the CH2-CH3 segment are expressed as a contiguous recombinant peptide, and two of such peptides form a dimeric configuration. The Fc fusion proteins of receptors of several cytokines and cell surface proteins, such as belatacept for cytotoxic T-cell protein 4 (CTLA-4), etanercept for tumor necrosis factor-$\alpha$ (TNF-$\alpha$), aflibercept for vascular endothelial growth factor (VEGF), and rilonacept for interleukin 1 (IL-1), have been developed and broadly used clinically. Many of the cytokine and cytokine receptors have serum half-lives of less than 1 day. The conjugation with Fc of IgG can lengthen their half-lives to more than 1 week.

Fusion with albumin provides another avenue to lengthen the half-lives of peptide or protein therapeutics. Albumin has a half-life of 19 days in the blood circulation. Because albumin is a single polypeptide protein, an albumin fusion protein with a peptide or protein can be produced as a recombinant peptide. For example, albiglutide is an albumin fusion protein with a dipeptideyl peptidese-4-resisitant glucagon-like peptide 1 (GLP-1) dimer and has been approved to treat type-2 diabetes. Albiglutide has a serum half-life of 4-7 days, as compare to 1-2 hours of a regular GLP-1. Idelvion is an albumin fusion protein with coagulation factor IX. It allows treatment once every 14 days to control and prevent bleeding episodes in children and adults with hemophilia B.

Nevertheless, conventional means for increasing the serum half-life of therapeutic drugs are not quite flexible. That is, they often lack the adaptability to drugs that requires different pharmacokinetic profiles. Hence, the pursuit of drugs with improved or adjustable pharmacokinetic characteristics remains an important research and development direction.

SUMMARY

In a first aspect, the present disclosure is directed to a platform technology related to linker units for enhancing the serum half-life of a therapeutic drug. In particular, the linker unit comprises two or more fatty acid derivatives or dioic fatty acid derivatives that may be conjugated with the therapeutic drug (alone, or in the form of a drug bundle) via the click reaction. In this way, the fatty acid chains of a linker unit may fit into different hydrophobic cavities of a single human serum albumin (HSA) or the hydrophobic cavities of different HAS, thereby increasing the binding strength between the linker unit (and hence, the linker unit-drug conjugate, as a whole) and the HSA(s). Also, using the present platform technology, the number of the fatty acid chains and the distance between two fatty acid chain are readily adjustable. In this way, one may alter the pharmacokinetic profile of the therapeutic drug as needed or desired by varying the length and number of the fatty acid chain and the distance between two fatty acid chain.

According to certain embodiments of the present disclosure, the linker unit comprises a center core and 2 to 5 first elements. According to the embodiments of the present disclosure, the center core comprises, (1) 2 to 5 lysine (K) residues;

(2) optionally, one or more fillers, wherein any two of the K residues are adjacent to each other or are separated by the filler;

(3) optionally, a terminal spacer, wherein the terminal spacers is an N-terminal spacer linked to the N-terminus of the first K residue or a C-terminal spacer linked to the C-terminus of the last K residue; and (4) a conjugating moiety, linked to the terminal K residue or, in the case where the terminal spacer is present, the terminal amino acid residue of the terminal spacer by forming an amide bond therewith, wherein the conjugating moiety has a conjugating group selected from the group consisting of azide, alkyne, tetrazine, cyclooctene, and cyclooctyne group.

Generally, there are 2, 3, 4, or 5 K residues of the core. In various embodiments, any two of the K residues are adjacent to each other (i.e., there is no filler inbetween) or are separated by a filler. When there are multiple fillers, the composition of each filler may differ from one another.

In structure, each of the plurality of fillers and the terminal spacer, comprises, independently, (i) 1 to 12 amino acid residues that are independently selected from amino acid residues other than the K residue, or (ii) a PEGylated amino acid having 1 to 12 repeats of ethylene glycol (EG) unit. According to some illustrative embodiments, the filler or terminal spacer may comprise one or more glycine (G) and/or serine (S) residues. In some examples, the filler or terminal spacer consists of 2 to 10 amino acid residues; preferably, 2 to 5 amino acid residues. In some embodiments, the filler or terminal spacer comprises 2 to 5 EG repeats.

According to some embodiments of the present disclosure, the core comprises a N-terminal spacer that is linked to the N-terminus of the first linking amino acid residue starting from the N-terminus. Additionally, or alternatively, the core comprises a C-terminal spacer that is linked to the C-terminus of the last linking amino acid residue starting from the N-terminus.

According to some optional embodiments of the present disclosure, the linker unit comprises two conjugating moieties (e.g., a first conjugating moiety and a second conjugating moiety).

In some optional embodiment, a conjugating moiety may have a functional group that is capable of forming a covalent bond with the α-amino group (—NH$_2$) of the terminal amino acid residue (i.e., the first linking amino acid residue or the N-terminal amino acid residue of the N-terminal spacer) or the carboxyl group (—COOH) of the terminal amino acid residue (i.e., the last linking amino acid residue or the C-terminal amino acid residue of the C-terminal spacer), so that the conjugating moiety is linked thereto. In certain embodiment, the core may have only one of the N- and C-terminal spacers, and has both the first and second conjugating moieties that are respectively linked to the two terminal amino acid residues (which may be the terminal linking amino acid residue or the terminal amino acid residue of the terminal spacer). There also embodiments in which the core comprises both of the N- and C-terminal spacers, and the two conjugating moieties are respectively linked to the terminal amino acid residues of the two terminal spacers. In preferred embodiments, the covalent bond formed between the conjugating moiety and the terminal amino acid residue is an amide bond. As could be appreciated, to ensure the homogeneity of the resultant linker unit, it is important one conjugating moiety only has one functional group that is reactable with either the α-amino group or the carboxyl group.

When choosing the two conjugating groups, it is desirable that the two conjugating groups cannot undergo a click chemistry reaction. According to some embodiment, when the first conjugating group is an azide, alkyne or cyclooctyne group, the second conjugating group cannot be any of the azide, alkyne or cyclooctyne group to avoid the reaction between the two conjugating groups; rather, the linking group can be a tetrazine, or cyclooctene group. In some other embodiments, when the first conjugating group is a tetrazine or cyclooctene group, the second conjugating group cannot be either the tetrazine or cyclooctene group; instead, the second conjugating group can be an azide, alkyne, or cyclooctyne group. As could be appreciated, in the situation where the two conjugating moieties are intended to conjugate with a single species of functional element, the conjugating groups of the two conjugating moieties may be the same or may be subjected to the same click chemistry reaction.

Each of the first elements is independently a $C_{8-28}$ fatty acid derivative or a $C_{8-28}$ dioic fatty acid derivative, and is linked with one of the K residues via the ε-amino acid group of the K residue. According to various embodiments of the present disclosure, the first element is a fatty acid derivative, which is derived from octanoic acid, pelargonic acid, decanoic acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, palmitoleic acid, oleic acid, lionleic acid, ricinoleic acid, or vaccenic acid, eicosapentaenoic acid (EPA), docosahexaenoic acid (DHA). According to certain embodiments of the present disclosure, the first element is a dioic fatty acid derivative, which is derived from suberic acid, azelaic acid, sebacic acid, undecanedioic acid, dodecanedioic acid, brassylic acid, tetradecanedioic acid, pentadecanedioic acid, thapsic acid, heptadecanedioic acid, or octadecanedioic acid. In some embodiments, the present first element is derived from myristic acid or palmitic acid. In other embodiments, the present first element is derived from tetradecanedioic acid or thapsic acid.

In certain embodiments, the fatty acid (or dioic fatty acid) derivative is a chemically modified fatty acid molecule (or dioic fatty acid). For example, the carboxyl group of the fatty acid molecule (or one of the carboxyl group of the dioic fatty acid molecule) is reacted with a chemical moiety with two functional groups, in which one functional group is carboxyl-reactive (thereby, forming a covalent bond with the (dioic) fatty acid molecule), whereas the other is a functional group reactive with the sidechain amino group of the lysine residue. According to optional embodiments of the present disclosure, the chemical entity modifying the (dioic) fatty acid molecule is a glutamate residue, aspartate residue, amino-$EG_2$-acid, gamma-aminobutyric acid, or the like; however, the present disclosure is not limited thereto.

According to embodiments of the present disclosure, the two or more first elements linked with the core may be the same or different. As could be appreciated, during the solid-phase synthesis of the peptide core, instead of attaching the first elements to the core after the core has been synthesized, it is also feasible to incorporate a K amino acid residue modified with a specific first element into the peptide chain. Therefore, according to various embodiments, K residues modified with different first elements may be added sequentially during the solid-phase synthesis, so as to give a batch of homogeneous linker units, wherein each linker units may have two or more different first elements linked thereto.

According to some embodiments of the present disclosure, the present linker unit further comprises a second element that is linked to the conjugating group via copper catalyzed azide-alkyne cycloaddition (CuAAC) reaction, strained-promoted azide-alkyne click chemistry (SPAAC) reaction, or inverse electron demand Diels-Alder (iEDDA) reaction. The second element may be any molecule that provides a therapeutic benefit in the treatment of a disease or a condition. Preferably, the second element is a peptide-based drug, for example, insulin, insulin-like growth factor, glucagon-like peptide-1 agonist, somatostatin and somatostatin analogues, calcitonin, growth hormone, erythropoietin, gonadotropin releasing factor, granulocyte colony stimulating factor, adenosine deaminase, asparaginase, interferon-α, interferon-β, TNF-α receptor, IL-1 receptor, EGF receptor, agalsidase 13, agalsidase a, laronidase, idursulphase, alglucosidase α, and galsulphase, or a derivative or variant thereof.

As could be appreciated, the second molecule may be modified to have a reactive group corresponding to the conjugating group, so that the second element is linked with the conjugating group of the core. In some embodiments, the peptide-based drug may have only one lysine or one unpaired cysteine residue, and such lysine or cysteine residue is not important to the biological activity or the therapeutic functionality of the peptide-based drug; in these cases, the lysine or unpaired cysteine residue is modified with the reactive group. For example, a chemical moiety having the reactive group is reacted with the α-amino group of the lysine residue or the SH group of the cysteine residue. In some embodiments, the chemical moiety having the reactive group may be a bifunctional crosslinker, in which the functional group at one end is reactive with the ε-amino group or the SH group, and the other end has the reactive group. Further, for peptide-based drug with no lysine or cysteine residue, a solvent accessible residue on the surface of the protein molecule, which is not required for the biological activity of the protein, can be mutated to a lysine or cysteine residue. In certain embodiments, the peptide-based drug may have lysine or cysteine residue that is important to the biological activity of the drug, or the peptide-based may have more than one lysine residues or a plurality of paired cysteine residues. In these cases, a solvent accessible residue on the surface of the protein molecule, which is not required for the biological activity of the protein, can be mutated to a cysteine residue. As another example, the alpha-amino group of the N-terminal amino acid residue of the peptide-based drug may be modified with the reactive group; such example is particular suitable in peptide prepared using solid phase synthesis. As could be appreciated, the above-mentioned strategies are only illustrative examples for modifying the peptide-based drug so that it has a reactive group that can undergo the click reaction with the conjugating group of the core, and then present invention is not limited thereto.

In some optional embodiments, the second element may be present in the form of a drug bundle that comprises more than one second elements. For example, the drug bundle may have the structure as described in International Patent Application Publication Nos. WO 2016/112870; WO 2016/184426, WO 2017/036255, and WO 2017/036407; the entirety of these publications is incorporated herein by reference. Alternatively, the drug bundle may comprise a structure that is similar to the structure of the linker unit of the present disclosure, except that the first element (that is, fatty acid or dioic fatty acid derivative) is replaced with the second element identified above. Briefly, the drug bundle comprises a second core, a second conjugating moiety, a plurality of optional second linking arms, one or more optional fillers, and one or two optional terminal spacers, and the second element is linked to the core by via the sidechain amino group of the lysine residues in the second core or the second linking arm.

Preferably, when the linker unit comprises two conjugating groups (i.e., the first and the second conjugating groups), one of the conjugating groups is the azide, the picolyl azide, the alkyne or the cyclooctyne group, and the other of the conjugating groups is the tetrazine or the cyclooctene group.

Optionally, the linker unit may further comprise a second and a third elements respectively linked to the conjugating groups (i.e., the first and the second conjugating groups), in which the second element is linked to the first conjugating group via CuAAC reaction, SPAAC reaction or iEDDA reaction; and the third element is linked to the second conjugating group via CuAAC reaction, SPAAC reaction or iEDDA reaction, which is different from the reaction between the second element and the first conjugating group.

In general, the cyclooctene group is norbornene or trans-cyclooctene (TCO); and the cyclooctyne group is dibenzocyclooctyne (DBCO or DIBO), difluorinated cyclooctyne (DIFO), bicyclononyne (BCN), or dibenzoazacyclooctyne (DIBAC). The tetrazine group is 1,2,3,4-tetrazine, 1,2,3,5-tetrazine or 1,2,4,5-tetrazine, or derivatives thereof. The azide group may be picolyl azide or —N3 group.

BRIEF DESCRIPTION OF THE DRAWINGS

The present description will be better understood from the following detailed description read in light of the accompanying drawings briefly discussed below.

Figure 1A:
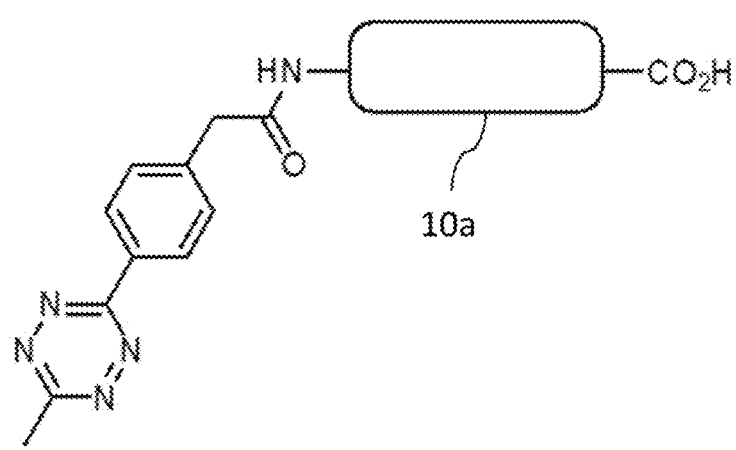
FIGS. 1A to 1H are schematic diagrams illustrating center cores according to certain embodiments of the present disclosure.
Figure 1B:
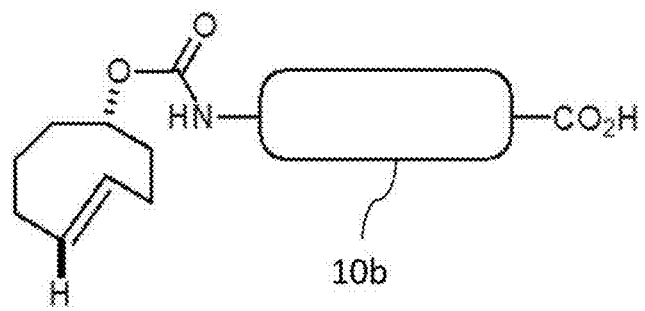
Figure 1C:
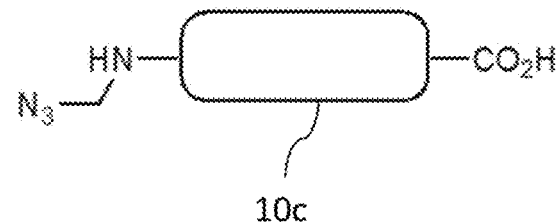
Figure 1D:
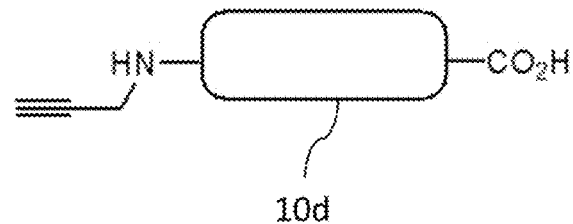

In accordance with common practice, the various described features/elements are not drawn to scale but instead are drawn to best illustrate specific features/elements relevant to the present invention. Also, like reference numerals and designations in the various drawings are used to indicate like elements/parts, where possible.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Specifically, as used herein and in the claims, the singular forms "a" and "an" include the plural reference unless the context clearly indicated otherwise. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

This present disclosure pertains generally to linker units, in which each linker unit comprises two to five hydrophobic chains (a fatty acid bundle) that may increase or alter the serum half-life of a therapeutic drug. The linker unit also comprises an effector element or a drug bundle comprising multiple effector elements. The effector element or drug bundle is linked with the fatty acid bundle via click reaction. The linker unit may also comprise a targeting element capable of directing the linker unit to or around a disease site within the subject.

As used herein, the term "targeting element" refers to the portion of a linker unit that directly or indirectly binds to a target of interest (e.g., a receptor on a cell surface or a protein in a tissue) thereby facilitates the transportation of the present linker unit into the interested target. In some examples, the targeting element may direct the linker unit to the proximity of the target cell. In other cases, the targeting element specifically binds to a molecule present on the target cell surface or to a second molecule that specifically binds a molecule present on the cell surface. In some cases, the targeting element may be internalized along with the present linker unit once it is bound to the interested target, hence is relocated into the cytosol of the target cell. A targeting element may be an antibody or a ligand for a cell surface receptor, or it may be a molecule that binds such antibody or ligand, thereby indirectly targeting the present linker unit to the target site (e.g., the surface of the cell of choice). The localization of the effector (therapeutic agent) in the diseased site will be enhanced or favored with the present linker units as compared to the therapeutic without a targeting function. The localization is a matter of degree or relative proportion; it is not meant for absolute or total localization of the effector to the diseased site.

According to the present invention, the term "effector element" refers to the portion of a linker unit that elicits a biological activity (e.g., inducing or suppressing immune activities, exerting cytotoxic effects, inhibiting enzymes, and the like) or other functional activity (e.g., recruiting immunocytes or other hapten tagged therapeutic molecules), once the linker unit is directed to its target site. The "effect" can be therapeutic or diagnostic. The effector elements encompass those that bind to cells and/or extracellular immunoregulatory factors. The effector element comprises agents such as proteins, nucleic acids, lipids, carbohydrates, glycopeptides, drug moieties (both small molecule drug and biologics), compounds, elements, and isotopes, and fragments thereof.

Although the terms, first, second, third, etc., may be used herein to describe various elements, components, regions, and/or sections, these elements (as well as components, regions, and/or sections) are not to be limited by these terms. Also, the use of such ordinal numbers does not imply a sequence or order unless clearly indicated by the context. Rather, these terms are simply used to distinguish one element from another. Thus, a first element, discussed below, could be termed a second element without departing from the teachings of the exemplary embodiments.

Here, the terms "link," "couple," and "conjugates" are used interchangeably to refer to any means of connecting two components either via direct linkage or via indirect linkage between two components.

The term "polypeptide" as used herein refers to a polymer having at least two amino acid residues. Typically, the polypeptide comprises amino acid residues ranging in length from 2 to about 200 residues; preferably, 2 to 50 residues. Where an amino acid sequence is provided herein, L-, D-, or beta amino acid versions of the sequence are also contemplated. Polypeptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages," e.g., where the peptide bond is replaced by an a-ester, a β-ester, a thioamide, phosphoramide, carbomate, hydroxylate, and the like. In the present disclosure, the term "peptide-based therapeutics" or "peptide-based drugs" is used in a broad sense to include any molecules with a therapeutic effect and comprises mainly amino acid residues, such as immunoglobulins, antibodies, antibody fragments, enzymes, growth factors, receptors, cytokines, and so on.

In certain embodiments, conservative substitutions of the amino acids comprising any of the sequences described herein are contemplated. In various embodiments, one, two, three, four, or five different residues are substituted. The term "conservative substitution" is used to reflect amino acid substitutions that do not substantially alter the activity (e.g., biological or functional activity and/or specificity) of the molecule. Typically, conservative amino acid substitutions involve substitution one amino acid for another amino acid with similar chemical properties (e.g., charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are considered to be derived synthetically from the standard amino acids without sufficient change to the structure of the parent, are isomers, or are metabolite precursors. In the present application, the amino acid residues (1) lysine, which contains an $NH_2$ group in its side chain, (2) cysteine, which contains an SH group in its side chain, (3) serine and threonine, which contain an OH group in their side chain, and (4) aspartic acid and glutamic acid, which contain a $CO_2H$ group in their side chain, are considered four distinctive groups of amino acids. These four groups of amino acids each contain in their side chains a unique functional group, which may be applied for conjugating to various chemical components. Non-natural amino acids, which contain the same functional groups in the side chains may be substituted for similar purposes. It is important to point out that the $CO_2H$ group of an aspartic acid or glutamic acid residue can undergo amide bond formation reaction with the $NH_2$ group of an element. Such reaction chemistry is similar to the amide bond formation between the $NH_2$ group of a lysine residue and an element that has a $CO_2H$ group. Thus, aspartic acid or glutamic acid residue can be used in place of lysine residue in a center core and the conjugation of the first elements can both use the same reaction chemistry for amide bond formation.

In certain embodiments, polypeptides comprising at least 80%, preferably at least 85% or 90%, and more preferably at least 95% or 98% sequence identity with any of the sequences described herein are also contemplated.

"Percentage (%) amino acid sequence identity" with respect to the polypeptide sequences identified herein is defined as the percentage of polypeptide residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two polypeptide sequences was carried out by computer program Blastp (protein-protein BLAST) provided online by Nation Center for Biotechnology Information (NCBI). The percentage amino acid sequence identity of a given polypeptide sequence A to a given polypeptide sequence B (which can alternatively be phrased as a given polypeptide sequence A that has a certain % amino acid sequence identity to a given polypeptide sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "PEGylated amino acid" as used herein refers to a polyethylene glycol (PEG) chain with one amino group and one carboxyl group. Generally, the PEGylated amino acid has the formula of $NH_2$—$(CH_2CH_2O)_n$—$CO_2H$. In the present disclosure, the value of n ranges from 1 to 20; preferably, ranging from 2 to 12.

As used herein, the term "terminus" with respect to a polypeptide refers to an amino acid residue at the N- or C-end of the polypeptide. With regard to a polymer, the term "terminus" refers to a constitutional unit of the polymer (e.g., the polyethylene glycol of the present disclosure) that is positioned at the end of the polymeric backbone. In the present specification and claims, the term "free terminus" is used to mean the terminal amino acid residue or constitutional unit is not chemically bound to any other molecular.

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present linker unit or a pharmaceutical composition comprising the same to a subject, who has a medical condition a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The term "effective amount" as used herein refers to the quantity of the present linker unit that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of subject being treated, the duration of the treatment, the nature of concurrent therapy (if any), and the specific formulations employed and the structure of the compounds or its derivatives. Effective amount may be expressed, for example, as the total mass of active component (e.g., in grams, milligrams or micrograms) or a ratio of mass of active component to body mass, e.g., as milligrams per kilogram (mg/kg).

The terms "application" and "administration" are used interchangeably herein to mean the application of a linker unit or a pharmaceutical composition of the present invention to a subject in need of a treatment thereof.

As used herein, the term "consecutive" used in connection with the K residue of the present disclosure refers to two K residues of a polypeptide that are adjacent to each other (i.e., without any other amino acid residues disposed between them). In certain examples of the present disclosure, two consecutive K residues in the center core are separated by at least one filler of the present disclosure, for example, two consecutive K residues in the center core may be separated by GS, GGS, or GSG.

The terms "subject" and "patient" are used interchangeably herein and are intended to mean an animal including the human species that is treatable by the linker unit, pharmaceutical composition, and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammals except human.

Albumin is a major protein in serum, amounting 35-50 g/L/ Albumin can serve as a transporter and depot for many substances, including some fatty acids, metabolites, drug molecules, etc. Each albumin molecule contains at least seven pockets (or hydrophobic cavities), and a fatty acid chain may fit snugly into such pocket. Therefore, the association with albumin can alter the pharmacokinetic properties of a pharmaceutical. Several pharmaceuticals are modified with a long-chain fatty acid and thereby attain the ability to associate with albumin in a non-covalent fashion and have much increased half-lives.

A commercial version of insulin (insulin detemir) has a fatty acid, myristic acid, conjugated to the amino group of a lysine residue (the 29th amino acid residue on the B chain). A version of GLP-1 agonist (liraglutide), has a fatty acid (palmitoyl group) conjugated to a glutamic acid residue, which is then conjugated to the amino group of a lysine residue (the 25th amino acid residue); the other lysine residue at the 33rd position has been mutated to arginine. The modified insulin and GLP-1 receptor agonist can bind to albumin and hence achieve long-acting pharmacokinetics.

The concept of using albumin as a depot for pharmaceuticals can be applied more generally and broadly for many more pharmaceuticals. For many existing drugs and new drugs under development, if the methods of modifying pharmaceuticals with binding affinity to albumin can be increased, perhaps new utilities can be established for various clinical indications.

Enzyme replacement therapy has been employed for a number of rare genetic diseases. The therapeutic enzymes are typically produced as recombinant proteins. For example, agalsidase β and agalsidase α for Fabry's disease; laronidase for Hurler-Scheie syndrome (also known as mucopolysaccharidosis type 1, MPS-I); idursulphase for Hunter's disease (also known as MPS-II); alglucosidase α for Pompe's disease; galsulphase for Maroteaux-Lamy syndrome. These enzymes have not been prepared for long acting and need to be dosed frequently. Because the patients using those enzymes are affected by severe clinical conditions, a less frequent drug administration should help those patients and cut down the expenses in using those enzymes. Therefore, there are persuading reasons to prepare new versions of those enzymes with longer half-lives.

The present disclosure is based on a novel platform that allows for a flexible and facile means for constructing fatty acid bundles that can be conjugated with a therapeutic drug (that is, an effector) so as to alter or, preferably, increase the pharmacokinetic characteristics (such as, serum half-life) of the effector element. The present platform is advantageous in that the number of the fatty acid (and diacid; unless otherwise specified, the term fatty acid also includes the dioic fatty acid) chain can be adjusted by altering the number of the K residues of the core. Also, the distance between two K residues can be varied by changing the length of the filler between the K residues of the core. As could be appreciated, the more the fatty acid chain carried by the present linker unit, the higher the chance that the linker unit may non-covalently associate with more pockets of a single HSA or with the pocket of different HSAs. Also, the distance between two fatty acid chain may affect the kinetic of the association between the fatty acid chain and the same or different HSAs.

PART I Multi-Arm Linkers for Treating Specific Diseases

I-(i) Peptide Core for Use in Multi-Arm Linker

The proteins, which account for the highest concentrations in blood, include albumin (35-50 g/L), immunoglobulin (Ig) G (7-18 g/L), IgA (0.8-6 g/L), IgM (0.4-4 g/L) and fibrinogen (2-4.5 g/L) in human adults. It is known that these proteins have longer half-life as compared to other proteins. For example, albumin has a circulating half-life of 19 days and IgG (IgG1, IgG2, and IgG4) has a half-life of over 20 days. Based on the pharmacokinetic property, these proteins may serve as a harbor for transitional, intermittent docking of pharmaceutical molecules thereby extending the half-life thereof.

Accordingly, the first aspect of the present disclosure pertains to a linker unit that comprises, (1) a center core that comprises 2-5 lysine (K) residues, and (2) 2-5 first elements respectively linked to the K residues of the center core. The present center core is characterized in having one or two conjugating groups bonded to its N- or/and C-terminus. According to the embodiments of the present disclosure, the conjugating group is useful in efficiently coupling a functional element (e.g., an effector element) to the center core, while each of the first elements is a fatty acid (or diacid) exhibiting a binding affinity toward albumin, or a single-chain variable fragment (scFv) specific for albumin, IgG, IgA or IgM. The present linker unit provides a means to extend the half-life of the functional element, and thus, improving the therapeutic effect thereof.

According to some embodiments of the present disclosure, each of the 2 to 5 first elements is a fatty acid or diacid, or a derivative thereof. In the preparation of the present linker unit, the first element is linked to the side chain of the K residue via forming an amide bond between the $CO_2H$ group of the fatty acid (or diacid) and the amine group of the K residue. In some embodiments, the fatty acid or diacid is modified with a chemical entity, and such fatty acid or diacid derivative is linked with the side chain amino group of the K residue via the functional group of the chemical entity. For example, the fatty acid or diacid is modified with glutamate, according to some embodiment of the present disclosure.

According to various embodiments of the present disclosure, the first element is a fatty acid derivative, which is derived from octanoic acid, pelargonic acid, decanoic acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, palmitoleic acid, oleic acid, lionleic acid, ricinoleic acid, or vaccenic acid, eicosapentaenoic acid (EPA), docosahexaenoic acid (DHA). According to certain embodiments of the present disclosure, the first element is a dioic fatty acid derivative, which is derived from suberic acid, azelaic acid, sebacic acid, undecanedioic acid, dodecanedioic acid, brassylic acid, tetradecanedioic acid, pentadecanedioic acid, thapsic acid, heptadecanedioic acid, or octadecanedioic acid. In some embodiments, the present first element is derived from myristic acid or palmitic acid. In other embodiments, the present first element is derived from tetradecanedioic acid or thapsic acid.

According to the embodiments of the present disclosure, the center core is a polypeptide that has 5-120 amino acid residues in length, and comprises 2 to 5 K residues, in which each K residue and its next K residue (i.e., two consecutive K residues) are adjacent with each other or separated by a filler.

As could be appreciated, the number of the first elements linked to the center core is mainly determined by the number of K residues comprised in the center core. Since there are at least two K residues comprised in the present center core, the present linker unit may comprise a plurality of first elements.

Depending on the K residues comprised in the center core, the amino acid residues of the filler are respectively selected from the group consisting of, glycine (G), serine (S), arginine (R), histidine (H), threonine (T), asparagine (N), glutamine (Q), proline (P), alanine (A), valine (V), isoleucine (I), leucine (L), methionine (M), phenylalanine (F), tyrosine (Y), and tryptophan (W) residues.

According to some embodiments of the present disclosure, the amino acid residues of fillers are independently selected from the group consisting of, G, S, R, and H residues. In an alternative example, the amino acid residues of the filler are respectively R or H residues.

The filler placed between the K residues may be variations of specified amino acid residues in somewhat random sequences and/or lengths. Longer fillers may be used for a polypeptide with fewer K residues, and shorter fillers for a polypeptide with more K residues. Hydrophilic amino acid residues, such as N, O, R, and H, may be inserted into the fillers together with G and S. As alternatives for fillers made up with G and S residues, fillers may also be adopted from flexible, soluble loops in common human serum proteins, such as albumin and immunoglobulins.

Alternatively, the filler can be a PEGylated amino acid having 2 to 12 repeats of ethylene glycol (EG) unit.

In general, the fillers in a center core may be the same or different. Specifically, each of the fillers may comprise the same of different amino acid residues/EG units. Alternatively, some of the fillers of the center core may be the PEGylated amino acid having 3 repeats of EG units, while the others of the fillers of the center core may be the PEGylated amino acid having 5-7 repeats of EG units.

In addition to the fillers, the present center core further comprises one or two optional terminal spacers having a conjugating group bonded thereto. The terminal spacer comprises (i) two or more amino acid residues that are independently selected from amino acid residues other than the K residue, or (ii) a PEGylated amino acid having 2 to 12 repeats of EG unit. According to the embodiments of the present disclosure, the conjugating group is bonded to the alpha-$NH_2$ group of the terminal spacer (i.e., the alpha-$NH_2$ group of the amino acid residue/PEGylated amino acid disposed at the N-terminus of the terminal spacer), or bonded to the $CO_2H$ group of the terminal spacer (i.e., the $CO_2H$ group of the amino acid residue/PEGylated amino acid disposed at the C-terminus of the terminal spacer).

According to one embodiment of the present disclosure, the center core comprises one terminal spacer, which is disposed upstream of the N-terminal K residue; in this embodiment, the conjugating group is bonded to the alpha-$NH_2$ group of the terminal spacer. According to another embodiment of the present disclosure, the center core comprises one terminal spacer, which is disposed downstream of the C-terminal K residue; in this embodiment, the conjugating group is bonded to the $CO_2H$ group of the terminal spacer. According to still another embodiment of the present disclosure, the center core comprises two terminal spacers, in which one of the terminal spacers is disposed upstream of the N-terminal K residue and has a first conjugating group bonded to the alpha-$NH_2$ group thereof; and the other of the terminal spacers is disposed downstream of the C-terminal K residue and has a second conjugating group bonded to the $CO_2H$ group thereof.

The conjugating group is selected from the group consisting of, an azide, a picolyl azide, an alkyne, a tetrazine, a cyclooctene, a cyclooctyne, a maleimide, a vinyl sulfone, a mono-sulfone, a methylsulfonyl benzothiazole, an iodo, and an iodoacetamide groups. According to the preferred example of the present disclosure, the conjugating group is the azide, the picolyl azide, the alkyne, the tetrazine, the cyclooctene or the cyclooctyne group. As would be appreciated, when the center core has two conjugating groups bonded thereto, the two conjugating groups may be the same or different. Preferably, the two conjugating groups are different; for example, one of the conjugating groups may be the azide, the alkyne or the cyclooctyne group, and the other of the conjugating groups may be the tetrazine or the cyclooctene group.

In general, the cyclooctene group may be norbornene or TCO group; and the cyclooctyne group may be DBCO/DIBO, DIFO, BCN or DIBAC group. Regarding the tetrazine group, it may be 1,2,3,4-tetrazine, 1,2,3,5-tetrazine or 1,2,4,5-tetrazine, or derivatives thereof. According to one embodiment of the present disclosure, the tetrazine group is 6-methyl-tetrazine.

Figure 1E:
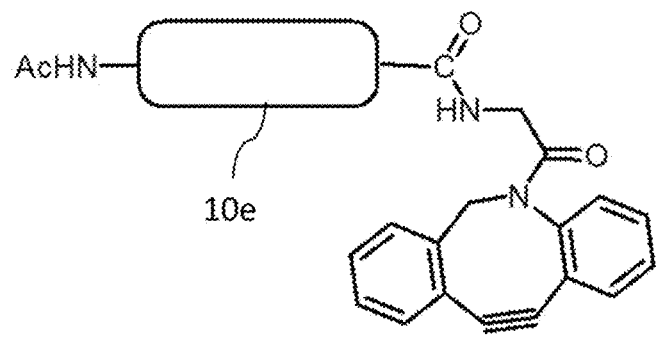

Reference is now made to FIGS. 1A-1E, in which each of the center core 10a, 10b, 10c, 10d and 10e has a conjugating group bonded thereto. In FIGS. 1A to 1D, a tetrazine group, a TCO group, an azide group and an alkyne group are respectively bonded to the alpha-$NH_2$ groups of the terminal spacers of center cores 10a, 10b 10c and 10d. FIG. 1E provides an alternative example, in which an acetyl group serving as a protecting group is bonded with the alpha-$NH_2$ group of the N-terminal spacer of the peptide core 10e, while a DBCO group serving as a conjugating group is bonded with the $CO_2H$ group of the C-terminal amino acid residue of the center core 10e.

Figure 1F:
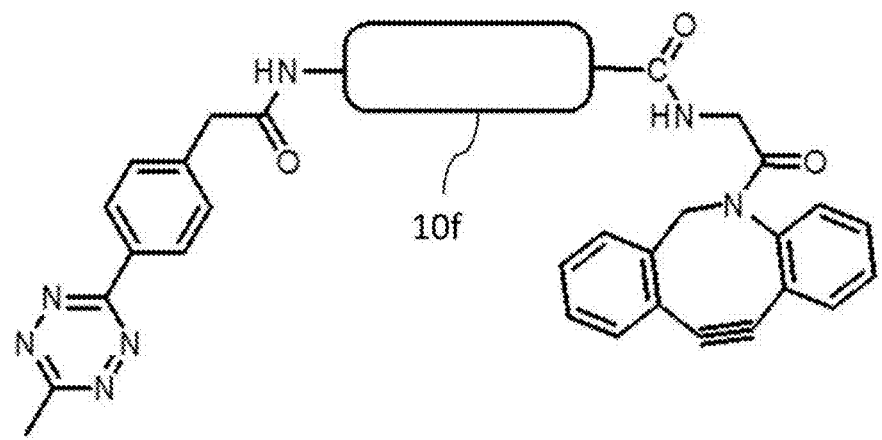
Figure 1G:
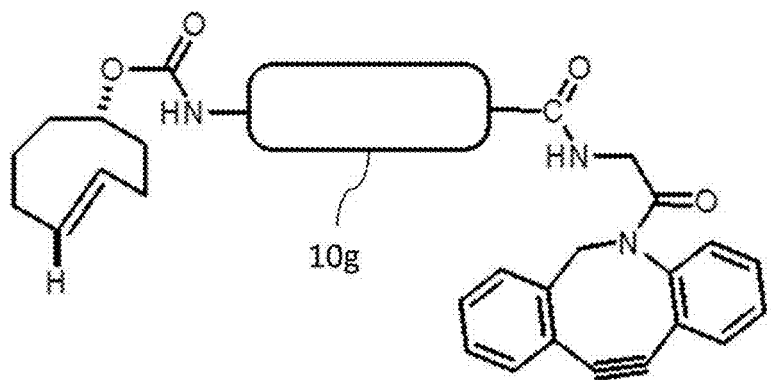
Figure 1H:
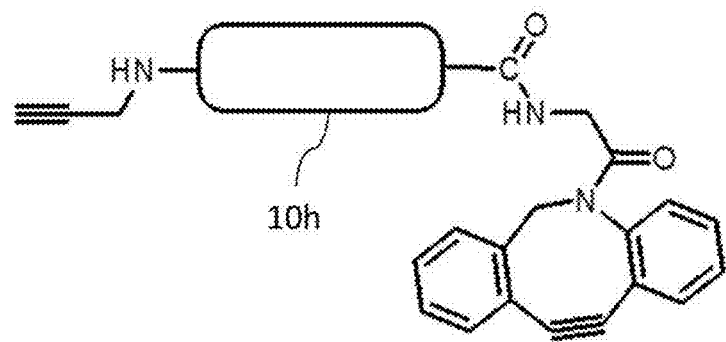

In some embodiments of the present disclosure, the center core comprises two conjugating groups. FIG. 1F illustrates such an example, in which a tetrazine group and a DBCO group are respectively bonded to the alpha-$NH_2$ group of the N-terminal spacer and the $CO_2H$ group of the C-terminal spacer of the peptide core 10f. FIG. 1G provides another example, in which a TCO group and a DBCO group are respectively bonded to the alpha-$NH_2$ group of the N-terminal spacer and the $CO_2H$ group of the C-terminal spacer of the peptide core 10g. In an alternative example, the alpha-$NH_2$ group of the N-terminal spacer and the $CO_2H$ group of the C-terminal spacer of the peptide core 10h are respectively bonded with an alkyne group and a DBCO group (FIG. 1H).

Schemes 1-3 provide the examples of producing the center core having one or two specified conjugating groups bonded thereto.

The synthesis of a polypeptide using PEGylated amino acids involves fewer steps than that with regular amino acids such as G and S residues. In addition, PEGylated amino acids with varying lengths (i.e., numbers of repeated ethylene glycol units) may be employed, offering flexibility for solubility and spacing between adjacent amino groups of K residues. In addition to PEGylated amino acids, the center cores may also be constructed to comprise artificial amino acids, such as D-form amino acids, homo-amino acids, N-methyl amino acids, etc. Preferably, the PEGylated amino acids with varying lengths of polyethylene glycol (PEG) are used to construct the center core, because the PEG moieties contained in the amino acid molecules provide conformational flexibility and adequate spacing between conjugating groups, enhance aqueous solubility, and are generally weakly immunogenic. The synthesis of PEGylated amino acid-containing center core is similar to the procedures for the synthesis of regular polypeptides.

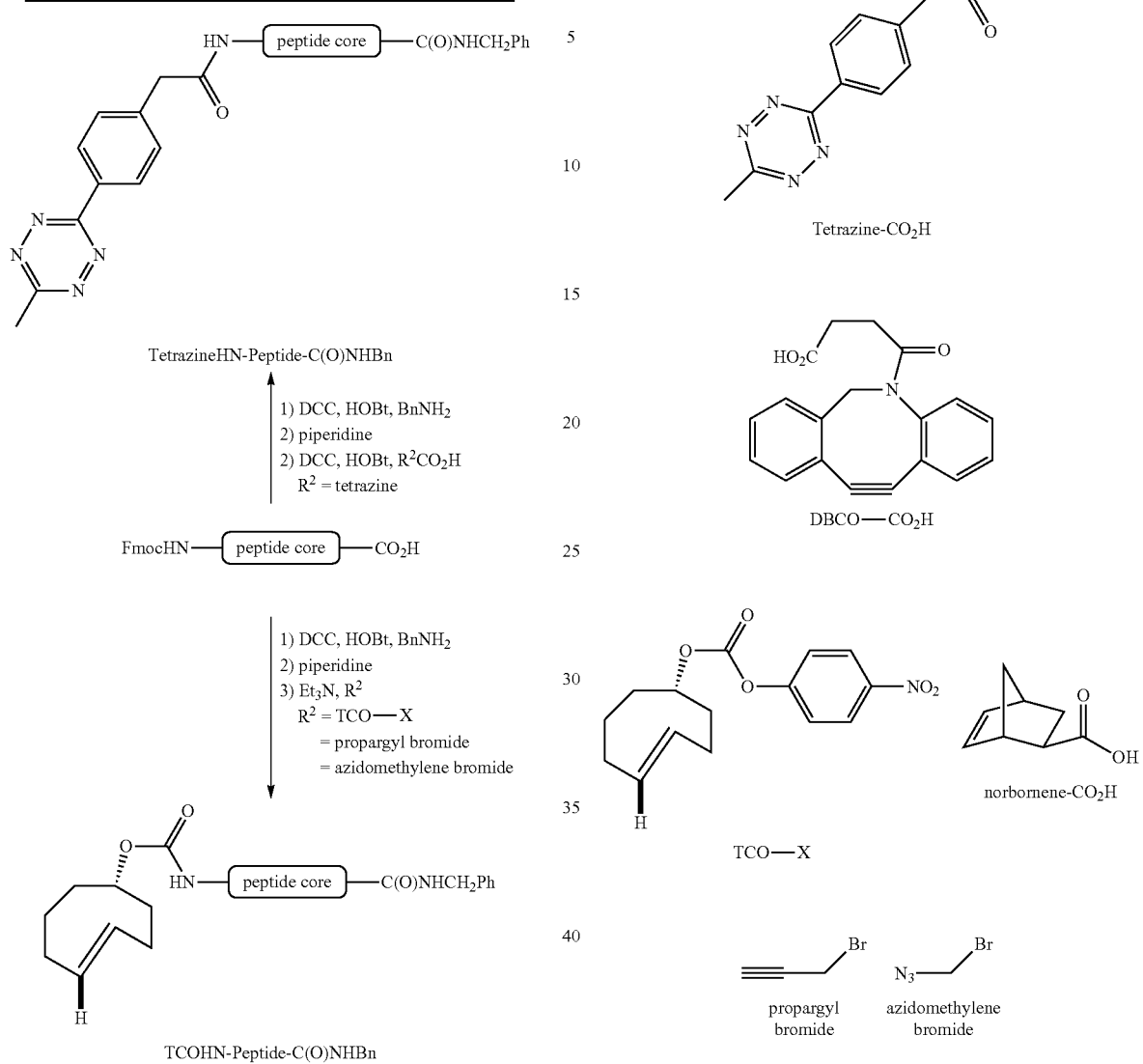
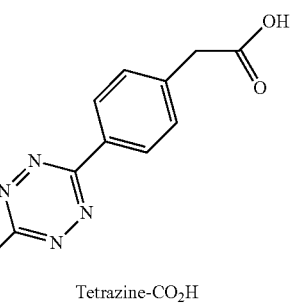
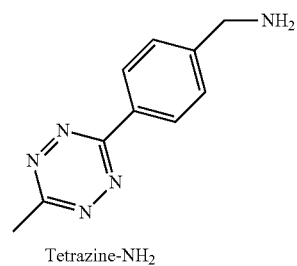

-continued

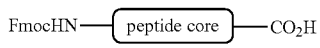

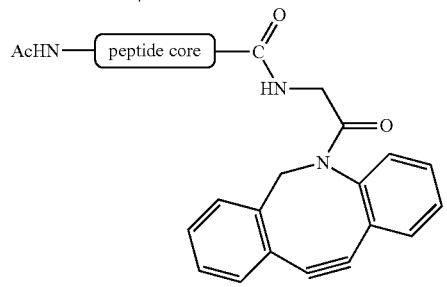

AcHN-Peptide-C(O)NHDBCO

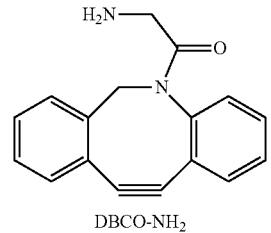

DBCO-NH$_2$

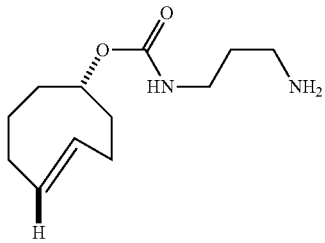

TCO-NH$_2$

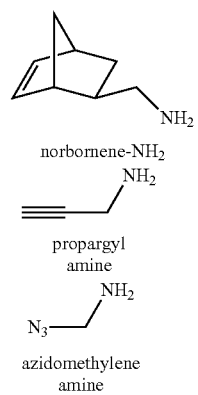

norbornene-NH$_2$ propargyl amine azidomethylene amine

For stability purpose, in the case when the N-terminus of the center core is not bonded with a conjugating group, it is preferably bonded with an acetyl group.

In the present disclosure, the reaction between the alpha-NH$_2$ group of the center core and the conjugating group, or between the CO$_2$H group of the center core and the conjugating group is denoted by the symbol "x" throughout the drawings.

<<Scheme 3 Production of center core having two conjugating groups respectively bonded to the N-and C-termini thereof>>

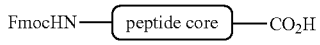

1) DCC, HOBT, DBCO—NH$_2$
2) piperidine
3) 3) Et$_3$N, R$^2$
   R$^2$ = TCO—X
     = propargyl bromide
     = azidomethylene bromide

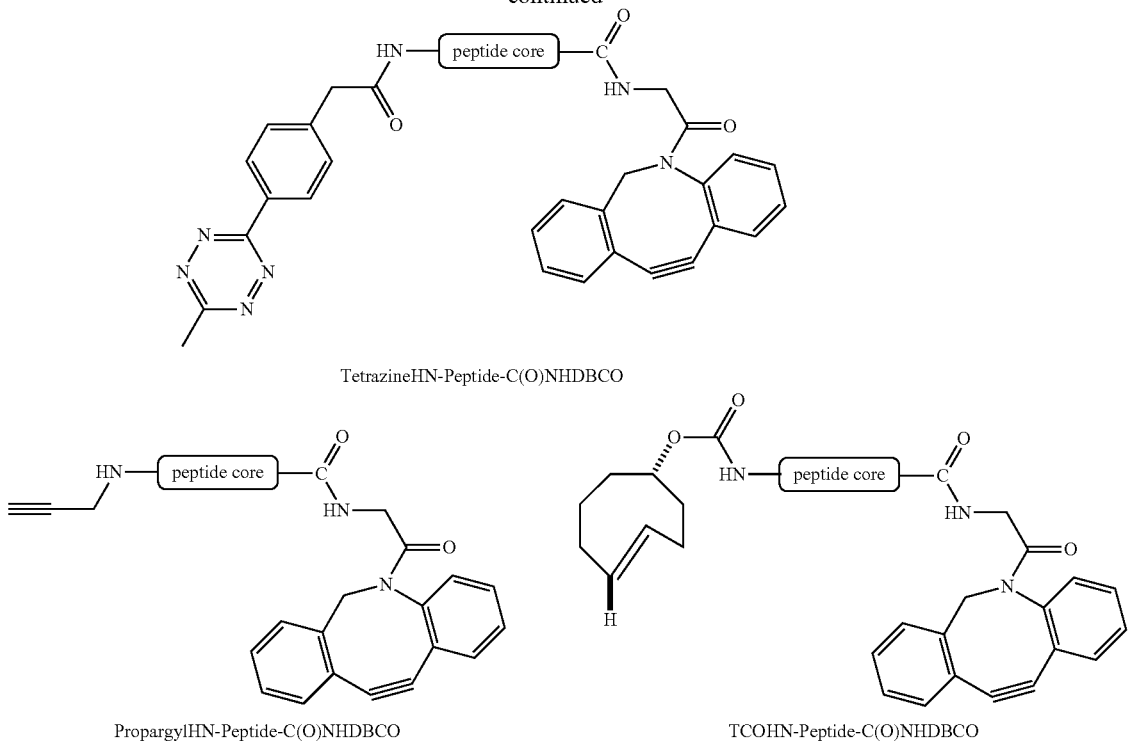

TetrazineHN-Peptide-C(O)NHDBCO

PropargylHN-Peptide-C(O)NHDBCO

TCOHN-Peptide-C(O)NHDBCO

Figure 2A:
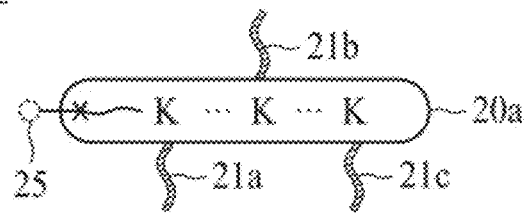
FIGS. 2A to 2C are schematic diagrams illustrating linker units according to certain embodiments of the present disclosure.

Reference is now made to FIG. 2A. As illustrated, the linker unit 20A comprises a center core 20a comprising three K residues respectively separated by fillers (denoted by the dots throughout the drawings). A terminal spacer (denoted by the symbol "~" throughout the drawings) is disposed upstream of the first K residue, and has a tetrazine group 25 bonded to the alpha-$NH_2$ group thereof. In this example, three first elements 21a-21c are respectively linked to the K residues.

Figure 2B:
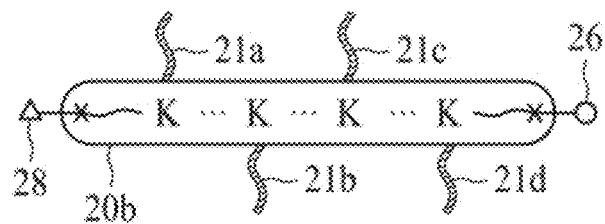

FIG. 2B provides a linker unit comprising two conjugating groups according to another embodiment of the present disclosure. The center core 20b comprises four K residues. A first and a second terminal spacers are respectively disposed at the N-terminus and the C-terminus of the center core, in which a DBCO group 28 is bonded to the alpha-$NH_2$ group of the first terminal spacer, and a TCO group 26 is bonded to the $CO_2H$ group of the second terminal spacer. In this example, the K residues are respectively linked to the first elements 21a-21d.

Alternatively, the first element may be an scFv specific for albumin, IgG, IgA or IgM. In this case, the first element is linked to the center core via a linking arm. Specifically, a PEG chain having an $NH_2$-reactive group (e.g., an N-hydroxysuccinimidyl (NHS) group) at one terminus and a functional group at the other terminus can be linked to any K residue of the center core by forming an amide bond between the $NH_2$-reactive group of the PEG chain and the amine group of the K residue. In the present disclosure, the PEG chain linked to the K residue is referred to as a linking arm, which has a functional group at the free-terminus thereof. In general, the functional group is selected from the group consisting of, a hydroxyl, a tert-Butyldimethylsilyl (TBDMS), an NHS, a maleimide, a vinyl sulfone, a mono-sulfone, methylsulfonyl benzothiazole, an iodo, an iodoacetamide, an azide, a picolyl azide, an alkyne, a cyclooctyne, a tetrazine and a cyclooctene groups. Depending on desired purposes, the maleimide group may be a substituted maleimide, for example, aryl-maleimide, 3-bromo-maleimide and 3,4-dibromo-maleimide. Preferably, when the conjugating group is the azide, the picolyl azide, the alkyne, or the cyclooctyne group, the functional group is not any of the azide, the picolyl azide, the alkyne or the cyclooctyne group. Alternatively, when the conjugating group of the center core is the tetrazine or the cyclooctene group, then the functional group is neither the tetrazine group nor the cyclooctene group.

Accordingly, the first element having a corresponding functional group may be linked to the free terminus of the linking arm via any of the following chemical reactions, (1) forming an amide bond therebetween: in this case, the linking arm has an NHS group at the free terminus, and the first element has an amine group;

(2) forming an ester bond therebetween: in this case, the linking arm has a hydroxyl or TBDMS group at the free terminus, and the first element has an hydroxyl-reactive group (e.g. a tosyl-O group);

(3) the thiol-maleimide (or vinyl sulfone) reaction: in this case, the linking arm has a maleimide, a vinyl sulfone, a mono-sulfone or a methylsulfonyl benzothiazole group at the free terminus, and the first element has a thiol group;

(4) the SN2 reaction: in this case, the linking arm has an iodo or an iodoacetamide group at the free terminus, and the first element has a thiol group;

(5) the Copper(I)-catalyzed alkyne-azide cycloaddition reaction (CuAAC reaction, or the "click" reaction for short): one of the free terminus of the linking arm and the first element has an azide or a picolyl azide group, while the other has an alkyne group; the CuAAC reaction is exemplified in Schemes 4 and 5;

(6) the inverse electron demand Diels-Alder (iEDDA) reaction: one of the free terminus of the linking arm and the first element has a tetrazine group, while the other has a TCO or a norbornene group; the iEDDA reaction is exemplified in Schemes 6 and 7; or (7) the strained-promoted azide-alkyne click chemistry (SPAAC) reaction: one of the free terminus of the linking arm and the first element has an azide group, while the other has an cyclooctyne group; the SPAAC reaction is exemplified in Scheme 8.

<<Scheme 4 CuAAC reaction occurred between an azide and alkyne groups>>

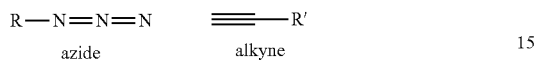
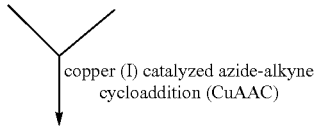
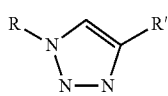

<< Scheme 5 CuAAC reaction occurred between a picolyl azide and an alkyne groups>>

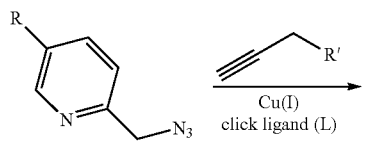
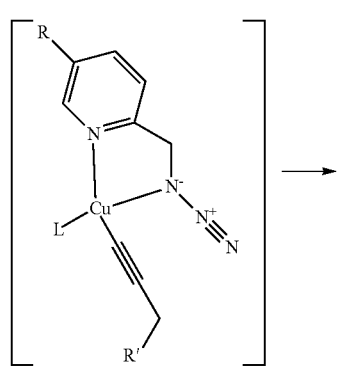
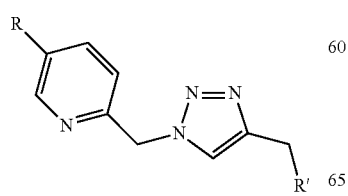

<< Scheme 6 iEDDA reaction occurred between a TCO an a tetrazine groups>>

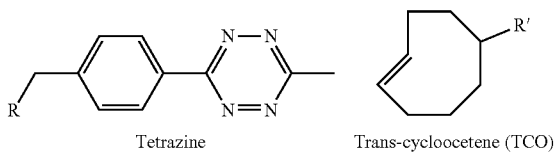
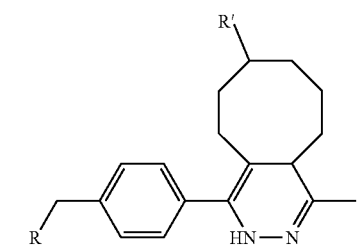

<< Scheme 7 iEDDA reaction occurred between a norbornene and a tetrazine groups>>

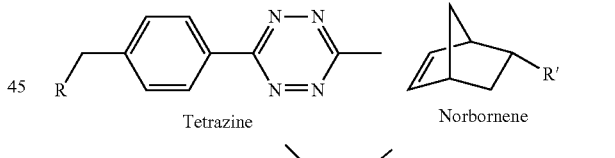
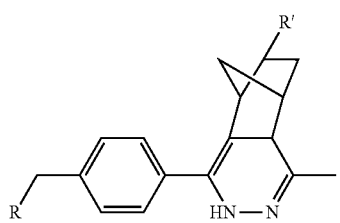

<<Scheme 8 SPAAC reaction occurred between an azide and a DBCO groups>>

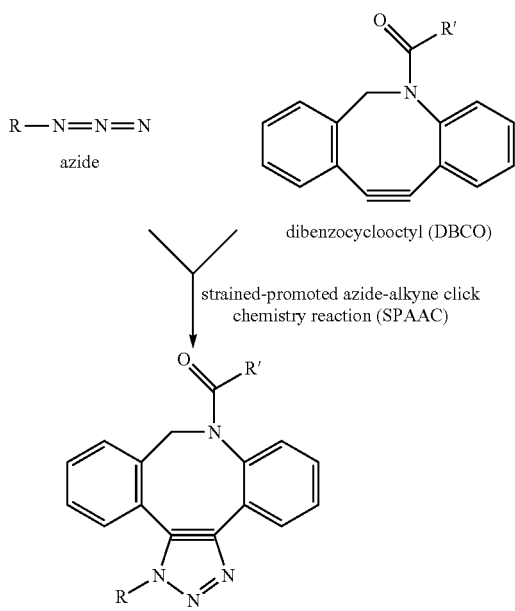

Figure 2C:
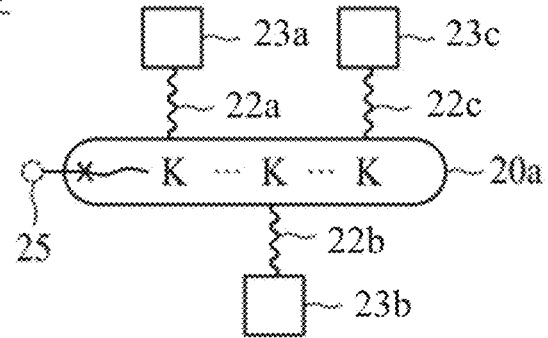

Reference is now made to FIG. 2C, in which the linker unit 20C has a similar structure with the linker unit 20A, except that the three first elements (23a, 23b and 23c) are respectively linked to the K residues via the linkage of three linking arms (22a, 22b and 22c).

According to certain embodiments of the present disclosure, the center core comprises two conjugating groups respectively bonded the alpha-$NH_2$ group of the N-terminal spacer and the $CO_2H$ group of the C-terminal spacer of the center core. In these embodiments, one of the conjugating groups is the azide, the picolyl azide, the alkyne or the cyclooctyne group, and the other of the conjugating group is the tetrazine or the cyclooctene group; preferably, the functional group of the linking arm is the hydroxyl, the TBDMS, the NHS, the maleimide, the vinyl sulfone, the monosulfone, the methylsulfonyl benzothiazole, the iodo or the iodoacetamide group.

The linking arm is preferably a PEG chain having 2-20 repeats of EG units. Alternatively, the linking arm may be a PEG chain having 2-20 repeats of EG units with a disulfide linkage at the terminus that is not linked with the linking arm. As would be appreciated, applicable linking arms are not limited by PEG chains. Peptides comprising glycine, serine and other amino acid hydrophilic residues, and polysaccharides, and other biocompatible linear polymers, which are modified to contain functional groups (e.g., an NHS, a maleimide, an azide, an alkyne, a tetrazine, or a strained alkyne group), can be used.

As could be appreciated, certain features discussed above regarding the linker units 20A-20C, or any other following linker units are common to other linker units disclosed herein, and hence some or all of these features are also applicable in the following examples, unless it is contradictory to the context of a specific embodiment. However, for the sake of brevity, these common features may not be explicitly repeated below.

The present linker unit may further comprise one or two functional elements linked to the conjugating group (e.g., azide, picolyl azide, alkyne, tetrazine, cyclooctene or cyclooctyne group) of the center core. Specifically, the functional element may be optionally conjugated with a short PEG chain (preferably having 2-12 repeats of EG units) and then linked to the conjugating group.

According to some embodiments of the present disclosure, the center core comprises one conjugating group (i.e., azide, picolyl azide, alkyne, tetrazine, cyclooctene or cyclooctyne group); and accordingly, a functional element (i.e., a second element) having an azide-reactive group (e.g., an alkyne or a DBCO group), an alkyne-reactive group (e.g., an azide or an picolyl azide group), a tetrazine-reactive group (e.g., a TCO or a norbornene group), a cyclooctene-reactive (e.g., an azide group) or a cyclooctyne-reactive group (e.g., a tetrazine group) can be linked to the conjugating group of the center core via the CuAAC reaction, iEDDA reaction or the SPAAC reaction.

Figure 3A:
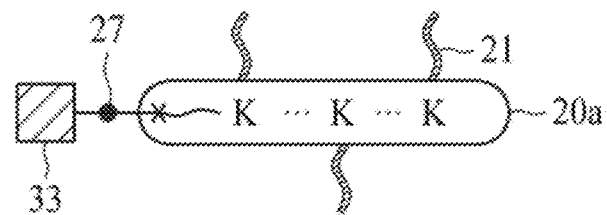
FIGS. 3A to 3C are schematic diagrams illustrating T-E linker units according to some embodiments of the present disclosure.

Reference is now made to FIG. 3A, in which the linker unit 30A has a similar structure with the linker unit 20A, except that the second element 33 is linked to the tetrazine group bonded to the terminal spacer. The solid dot 27 depicted in FIG. 3A represents the chemical bond resulted from the iEDDA reaction occurred between the tetrazine group and the second element.

According to other embodiments of the present disclosure, the center core comprises two conjugating groups. As mentioned above, when the first conjugating group is the azide, the picolyl azide, the alkyne or the cyclooctyne group, then the second conjugating group is preferably the tetrazine or the cyclooctene group. Accordingly, two functional elements (i.e., the second and the third elements) can be respectively linked to the center core via SPAAC and iEDDA reactions, or via CuAAC and iEDDA reactions. For example, a second element having a cyclooctyne-reactive group (e.g., an azide group) can be linked to the first conjugating group via the SPAAC reaction; while a third element having a alkyne-reactive group (e.g., an azide or an picolyl azide group), a tetrazine-reactive group (e.g., a TCO or a norbornene group), or a cyclooctene-reactive group (e.g., a tetrazine group) can be linked to the second conjugating group via the CuAAC or the iEDDA reaction. Alternatively, a second element having a tetrazine-reactive group (e.g., a TCO or a norbornene group) or the cyclooctene-reactive group (e.g., a tetrazine group) can be linked to the first conjugating group via the iEDDA reaction; and a third element having an azide-reactive group (e.g., an alkyne or a DBCO group), an alkyne-reactive (e.g., an azide or a picolyl azide group) or a cyclooctyne-reactive group (e.g., an azide group) can be linked to the second conjugating group via the CuAAC or the SPAAC reaction.

Figure 3B:
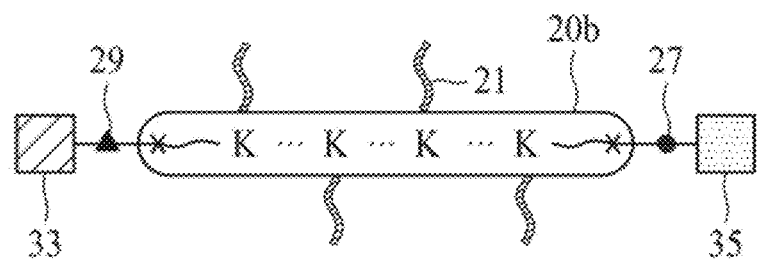

FIG. 3B provides an example of the present linker unit 30B comprising two conjugating groups respectively linked to the second and the third elements. The linker unit 30B has a similar structure with the linker unit 20B, except that the second element 33 is linked to the DBCO group, and the third element 35 is linked to the TCO group. The solid triangle 29 depicted in FIG. 3B represents the chemical bond resulted from the SPAAC reaction occurred between the DBCO group and the second element; and the solid dot 27 depicted in FIG. 3B represents the chemical bond resulted from iEDDA reaction occurred between the TCO group and the third element.

Figure 3C:
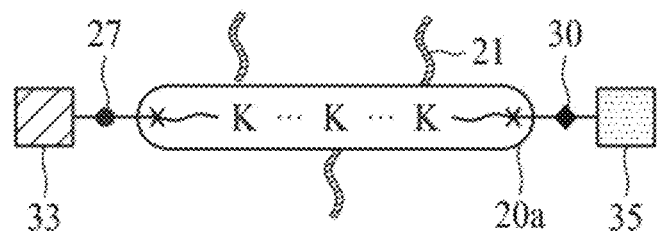

FIG. 3C provides an alternative example of present linker unit. The linker unit 30C comprises two functional elements (i.e., the second and the third elements), in which the second element 33 is linked to the tetrazine group bonded to the N-terminal spacer of the center core 20a, and the third element 35 is linked to the azide group bonded to the C-terminal spacer of the center core 20a. The solid dot 27 depicted in FIG. 3C represents the chemical bond resulted from iEDDA reaction occurred between the tetrazine group and the second element; and the diamond 30 depicted in FIG. 3C represents the chemical bond resulted from CuAAC reaction occurred between the azide group and the third element.

Depending on desired purposes, the functional element linked to the conjugating group of the center core may be any of molecule that provides a therapeutic benefit in the treatment of a disease or a condition. Exemplary functional elements include, but are not limited to, insulin, insulin-like growth factor, glucagon-like peptide-1 agonist, somatostatin and somatostatin analogues, calcitonin, growth hormone, erythropoietin, gonadotropin releasing factor, granulocyte colony stimulating factor, adenosine deaminase, asparaginase, interferon-$\alpha$, interferon-$\beta$, TNF-$\alpha$ receptor, IL-1 receptor, EGF receptor, agalsidase $\beta$, agalsidase $\alpha$, laronidase, idursuiphase, alglucosidase a, and galsuiphase, or a derivative or variant thereof.

I-(ii) Use of Multi-Arm Linker

The present disclosure also pertains to method for treating various diseases using the suitable linker unit. Generally, the method comprises the step of administering to a subject in need of such treatment an effective amount of the linker unit according to embodiments of the present disclosure.

Compared with previously known therapeutic constructs, the present linker unit discussed in Part I is advantageous in three points:

(1) The number of the first elements (i.e., the fatty acid, or the scFv specific to albumin, IgG, IgA or IgM) may be adjusted in accordance with the needs and/or applications. The present linker unit may comprise one functional element (i.e., the second element) or two functional elements (i.e., the second and the third elements) in accordance with the requirements of the application (e.g., the disease being treated, the route of administration of the present linker unit, and the binding avidity and/or affinity of the antibody carried by the present linker unit). For example, when the present linker unit is directly delivered into the tissue/organ (e.g., the treatment of eye), a second element acting as the effector element may be enough, thus would eliminate the need of a third element acting as the targeting element. However, when the present linker unit is delivered peripherally (e.g., oral, enteral, nasal, topical, transmucosal, intramuscular, intravenous, or intraperitoneal injection), it may be necessary for the present linker unit to simultaneously comprise a targeting element that specifically targets the present linker unit to the lesion site; and an effector element that exhibits a therapeutic effect on the lesion site. For the purpose of increasing the targeting or treatment efficacy or increasing the stability of the present linker unit, a third element (e.g., a second targeting element, a second effector element, or a PEG chain) may be further included in the present linker unit.

(2) The first element is provided in the form of a bundle. As described above, the number of the first elements (i.e., the fatty acids) may vary with the number of K residues comprised in the center core. If the number of K residues in the center core ranges from 2 to 5, then at least two first elements may be comprised in each linker unit that efficiently improves the half-life and the therapeutic effect of the functional elements (i.e., the second and/or the third element).

(3) The linker unit can be efficiently linked to the functional element or another molecular construct (see, Part II below) via the conjugating group bonded thereto. The present center core can be commercially synthesized. Otherwise, as the procedure illustrated in Schemes 4-8, the present center core can be easily made from a synthetic polypeptide, in which the N-terminal 9-fluorenylmethoxycarbonyl (Fmoc) serving as a protecting group to protect the a-amine group is replaced by the conjugating group (i.e., azide, picolyl azide, alkyne, tetrazine, cyclooctene or cyclooctyne group). Additionally or alternatively, the conjugating group may be bonded to the polypeptide via reacting with the $CO_2H$ group of the polypeptide. The thus-produced center core comprises one or two conjugating groups, which serves as a connector to link functional elements (e.g., the present second and/or third element) and the center core without the need of additional processing steps.

PART II Joint-Linker Molecular Constructs for Treating Specific Diseases

Another aspect of the present disclosure pertains to a molecular construct comprising at least two linker units, in which one linker unit carries a plurality of fatty acids (e.g., a fatty acid bundle), whereas another other linker unit carries a plurality of effector elements (e.g., a drug bundle). In the present disclosure, molecular constructs comprising two or more linker units are referred to as joint-linker molecular constructs. According to various embodiments of the present disclosure, the joint-linker molecular construct comprises two linker units as discussed in Part I.

II-(i) Structure of Joint-Linker Molecular Construct

According to some embodiments of the present disclosure, the molecular construct comprises two linker units, and the linker units are coupled to each other via either the CuAAC reaction, the SPAAC reaction, or the iEDDA reaction. In the embodiments, the first linker unit comprises (1) a center core, (2) a plurality of first elements respectively linked to the K residues of the center core, and (3) a conjugating group bonded to the N- or C-terminus of the center core that is selected from the group consisting of, an azide, a picolyl azide, an alkyne, a tetrazine, a cyclooctene and a cyclooctyne groups. Similarly, the second linker unit comprises (1) a center core, (2) a plurality of second elements respectively linked to the K residues of the center core, and (3) a conjugating group bonded to the N- or C-terminus of the center core that is selected from the group consisting of, an azide, a picolyl azide, an alkyne, a tetrazine, a cyclooctene and a cyclooctyne groups. The first and the second linker units may be coupled to each other via the CuAAC reaction, the SPAAC reaction, or the iEDDA reaction occurred between the conjugating groups.

According to some embodiments, each of the first elements is a fatty acid, or an scFv specific to albumin, IgG, IgA or IgM; and each of the second elements is a functional element that provides a therapeutic benefit in the treatment of a disease or a condition; for example, insulin, insulin-like growth factor, glucagon-like peptide-1 agonist, somatostatin and somatostatin analogues, calcitonin, growth hormone, erythropoietin, gonadotropin releasing factor, granulocyte colony stimulating factor, adenosine deaminase, asparaginase, interferon-$\alpha$, interferon-$\beta$, TNF-$\alpha$ receptor, IL-1 receptor, EGF receptor, agalsidase $\beta$, agalsidase $\alpha$, laronidase, idursulphase, alglucosidase $\alpha$, and galsulphase, or a derivative or variant thereof. For peptides or small proteins that have only one lysine residue, which is not essential for the biological activity of the peptides or proteins, the $\epsilon$-amino group of the lysine residue provides a functional group for reacting with a heterobifunctional crosslinker having an amino-reactive group, such as an N-hydroxysuccinimide (NHS) at one end and a functional group for chemistry at the other end. Since all proteins have multiple lysine residues and their cysteine residues are in pairs forming disulfide bonds, the lysine and cysteine residues are not ideal as sites for attaching a functional group for click chemistry. For such a protein, a solvent accessible residue on the protein surface, which is not required for the biological activity of the protein, can be mutated to a cysteine residue. This cysteine residue thus provides a sulfhydryl group, which can be reacted with a heterobifunctional crosslinker with a SH-reactive functional group, such as a maleimide group, at one end and a functional group for click chemistry at the other end.

Alternatively, the first linker unit comprises two conjugating groups respectively bonded to the N- and C-termini thereof, in which one of the conjugating groups is linked to a functional element, and the other of the conjugating groups is an azide, a picolyl azide, an alkyne, a tetrazine, a cyclooctene or a cyclooctyne group.

Still alternatively, both the first and the second linker units comprise two conjugating groups respectively bonded to the N- and C-termini thereof, in which one of the conjugating groups is linked to a functional element, and the other of the conjugating groups is an azide, a picolyl azide, an alkyne, a tetrazine, a cyclooctene or a cyclooctyne group. In this case, the functional elements of the first and the second linker units may be the same or different.

II-(iii) Use of Joint-Linker Molecular Construct

The present disclosure also pertains to method for treating various diseases using the suitable joint-linker molecular construct. Generally, the method comprises the step of administering to a subject in need of such treatment an effective amount of the joint-linker molecular construct according to embodiments of the present disclosure.

EXPERIMENTAL EXAMPLES

Example 1: Synthesis of Azide-Containing Glucagon-Like Peptide-1 (GLP-1) Agonist Human active GLP-1 is a peptide hormone deriving from the processing of the proglucagon peptide (1-37). Human GLP-1 (7-36) amide and GLP-1 (7-37) are the two truncated and equipotent biological active forms.

In this example, an azide-containing GLP-1 agonist was prepared, in which an azide group was linked to a GLP-1 agonist molecule (SEQ ID NO: 1) via the connection of a glutamate residue. Specifically, the y carboxyl group of the glutamate residue was linked to the E-amino group of the lysine residue of the GLP-1 agonist molecule (SEQ ID NO: 1), and the a-amino group of the glutamate residue is modified with an azidoacetyl group.

The azide-containing GLP-1 agonist was designed by the present inventors and the synthesis was outsourced to Shanghai WuXi AppTech Co., Ltd. (Shanghai, China). The procedure employed a stepwise Fmoc SPPS (solid phase peptide synthesis) procedure using O-Benzotriazole-N,N,N', N'-tetramethyl-uronium-hexafluoro-phosphate (HBTU)/N, N-diiso-propylethylamine (DIEA)/N,N-dimethylformamide (DMF) coupling chemistry, in which HBTU served as an in situ activating reagent for Fmoc protected amino acids and DIEA was used as an organic base during coupling. $N^\alpha$-Fmoc, side-chain protected amino acids, and 2-chlorotrityl chloride resin (CTC resin) were used in the synthesis. The following side-chain protection strategies were employed: Arg (Pbf), Trp (Boc), Thr (OtBu), Lys (N-Dde), Tyr (OtBu), Glu (OtBu), Gln (Trt), Ser (OtBu), His (Trt). For each coupling cycle, except the first cycle, 3 mmole Na-Fmoc-amino acid, 6 mmole DIEA and 2.85 mmole equivalent of HBTU were used. The Fmoc protecting group on the a-amine was removed with 20% piperridine in DMF solution (three times volume of peptide resin).

In step (i), the peptide synthesis started by covalently linking the first amino acid onto the resin: the amino acid Fmoc-Gly-OH (1.0 mmol, 297.5 mg) and CTC resin (1.0 mmole, substitution=1.0 mmole/g, 1.0 g) were dissolved in dichloromethane (DCM), and then DIEA (4.0 mmole) was added and the resulting mixture was swelled under nitrogen gas bubbling. Next, methanol (MeOH, 1.0 mL) as a capping reagent was added into the Fmoc-protected peptide resin and mixed for 0.5 hour to covalently link with unreacted carbocations on the CTC resin.

In step (ii), the methanol-contained capping solution was drained and then washed with DMF 3 times. In step (iii), after washing of the resin, the Fmoc protecting group on CTC resin was removed by adding 20% piperidine in DMF solution for 30 minutes. In step (iv), the resulting solution was drained and washed with DMF 5 times. In step (v), the manual coupling of the $2^{nd}$ amino acid was performed by adding Fmoc-Arg(Pbf)-OH (3 equiv) and the activating agent (HBTU) onto the resin under nitrogen gas bubbling for about 1 hour. Next, steps (ii) to (v) were repeated, each time with another amino acid according to peptide sequence. For each cycle of coupling steps, the coupling reaction was monitored by ninhydrin test.

For the cleavage of side-chain protected peptide from CTC resin, 40.0 mL cleavage buffer (5% TIS/5% $H_2O$/90% TFA) was prepared and added to the flask containing the resin, with stirring for 2 hours. The crude peptide was precipitated into cold tert-butyl methyl ether and centrifuged for 3 minutes at 6000 rpm. The crude peptide was washed by Tert-butyl methyl ether two additional times (total 400.0 mL) and was dried under vacuum for 2 hours.

Azide-containing GLP-1 agonist was purified by reverse phase HPLC on an Agilent SB-phenyl preparative HT column (250 mm×30 mm; 7 μm), using a mobile phase of acetonitrile and 0.075% trifluoroacetic acid, a linear gradient of 0% to 60% acetonitrile over 60 minutes, at a flow rate of 20 mL/min and a column temperature of 25° C.

Figure 4A:
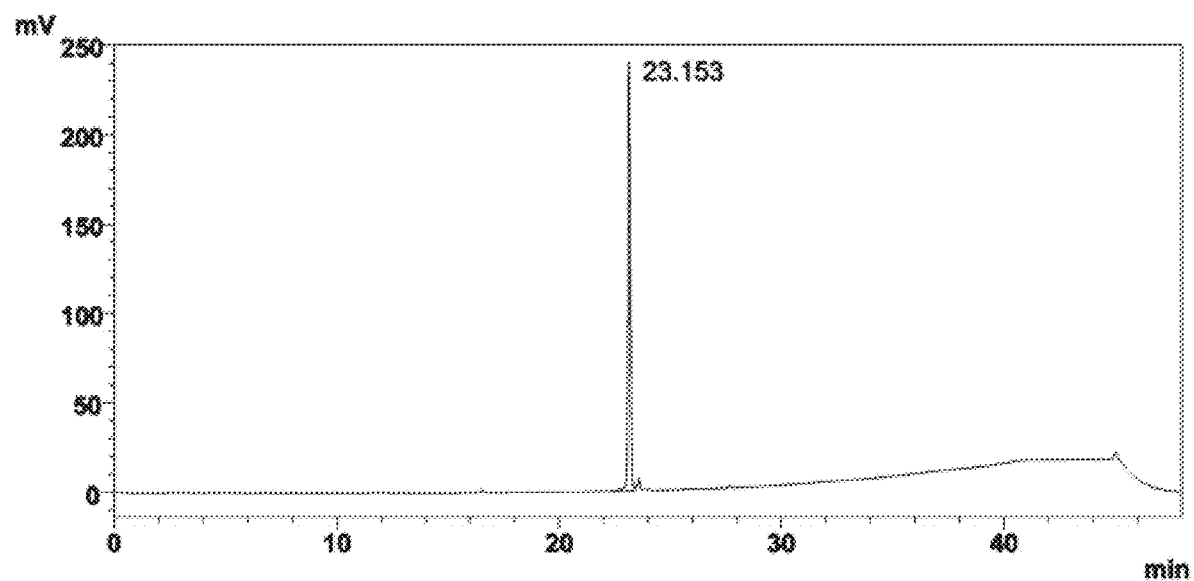
FIGS. 4A and 4B respectively show the reverse phase analytical HPLC profile and the MALDI-TOF result of azide-containing GLP-1 agonist, according to one example of the present disclosure.

The purified sample of azide-containing GLP-1 agonist was analyzed by reverse phase analytical HPLC on a Supelco C18 column (250 mm×4.6 mm; 5 μm), using a mobile phase of acetonitrile and 0.1% trifluoroacetic acid, a linear gradient of 0% to 100% acetonitrile over 30 minutes, at a flow rate of 1.0 ml/min and a column temperature of 25° C. FIG. 4A shows the reverse phase analytical HPLC profile of azide-containing GLP-1 agonist with the peak of the azide-containing GLP-1 agonist at OD254 nm with a retention time of 23.153 minutes.

The identification of the samples was carried out by MALDI-TOF mass spectrometry. Mass spectrometry analyses were performed by the Mass Core Facility at the Institute of Molecular Biology (IMB), Academia Sinica, Taipei, Taiwan. Measurements were performed on a Bruker Autoflex III MALDI-TOF/TOF mass spectrometer (Bruker Daltonics, Bremen, Germany).

Figure 4B:
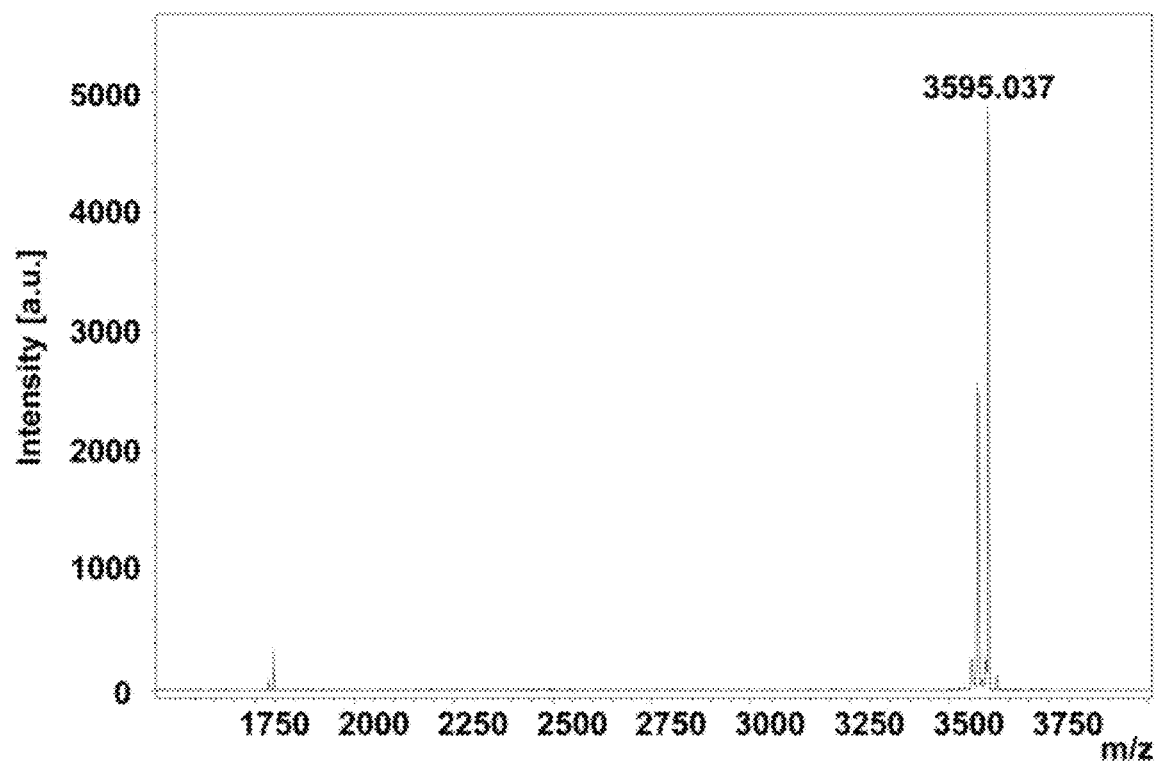

The mass spectroscopic analysis of the thus-synthesized azide-containing GLP-1 agonist, as provided in FIG. 4B, indicated that the molecular construct had a m.w. of 3,595.037 daltons. Abbreviations: Pbf, 2,2,4,6,7-Pentamethyldihydrobenzofuran-5-sulfonyl chloride; Boc, tert-butyloxycarbonyl; tBu, tert-butyl ether; Dde, 1-(4,4-dimethyl-2, 6-dioxocyclohex-1-ylidene)ethyl; Trt, triphenylmethyl; TIS, triisopropylsilane; TFA, trifluoroacetic acid.

Example 2: Synthesis of c-Aminoisobutyric Acid (Aib)-Substituted Glucagon-Like Peptide-1 (GLP-1) Agonist Having an Azide Group In this example, an Aib-substituted GLP-1 agonist having an azide group was prepared (SEQ ID NO: 2) (as illustrated below), in which the alanine residue at the residue position 8 of SEQ ID NO:1 was replaced by an Aib residue (one-letter code: U) for higher resistance to the dipeptidyl peptidase IV (DPP 4) degradation. In this example, the y carboxyl group of the glutamate residue was linked to the c-amino group of the lysine residue of the GLP-1 agonist molecule (SEQ ID NO: 2), and the α-amino group of the glutamate residue is modified with an azidoacetyl group.

Similar to the Example 1, the Aib-substituted GLP-1 agonist having an azide group was designed by the present inventors and the synthesis was outsourced to Shanghai WuXi AppTech Co., Ltd. (Shanghai, China). The procedure of the synthesis was performed as described in the preceding example.

The purified sample of Aib-substituted GLP-1 agonist having an azide group was analyzed by reverse phase analytical HPLC on a Supelco C18 column (250 mm×4.6 mm; 5 μm), using a mobile phase of acetonitrile and 0.1% trifluoroacetic acid, a linear gradient of 0% to 100% acetonitrile over 30 minutes, at a flow rate of 1.0 ml/min and a column temperature of 25° C. The identification of the sample was carried out by MALDI-TOF mass spectrometry (data not shown).

Example 3: Synthesis of a Somatostatin Analog Having a Cysteine Residue for Coupling Reaction As illustrated below, a somatostatin analog (SEQ ID NO: 3) containing a free cysteine residue for coupling to the maleimide group of the linking arm of a multi-arm linker was designed. The somatostatin analog was synthesized by a standard solid phase method, which was outsourced to Ontores Biotechnologies Co., Ltd. (Hangzhou, China). The somatostatin analog had a purity of more than 95%.

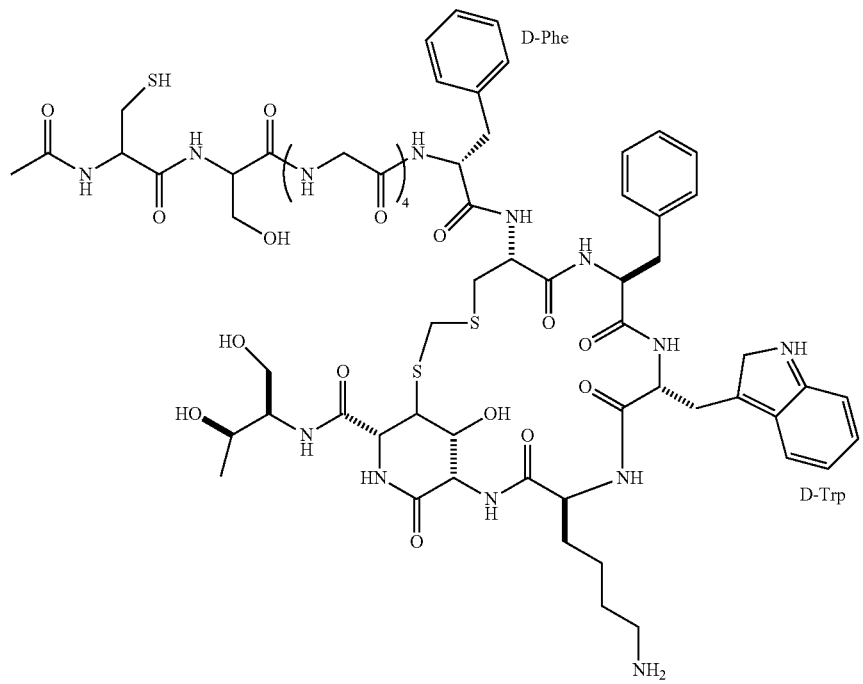

Figure 5:
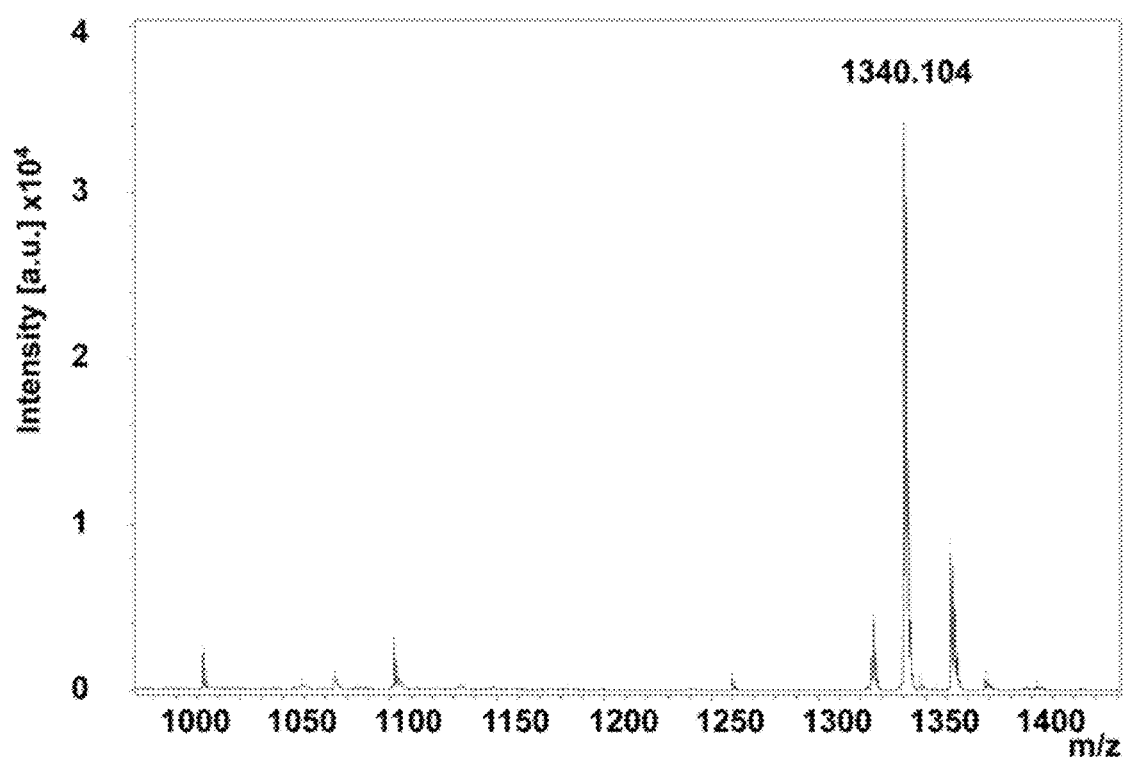
FIG. 5 show the MALDI-TOF result of alkyne-containing linker unit having two palmitoyl chains, according to one example of the present disclosure.

The identification of the synthesized peptide was carried out by mass spectrometry MALDI-TOF. FIG. 5 shows the result of mass spectrometry MALDI-TOF indicated that the present molecular construct had a m.w. of 1,493.587 daltons.

Example 4: Synthesis of DBCO-Containing Multi-Arm Linker Unit Conjugated with Three Somatostatin Analogs The procedure of synthesizing DBCO-containing multi-arm linker was as follows; in step (i), the synthesized peptide 2 (SEQ ID NO:4) (Chinapeptide Inc., Shanghai, China) was dissolved in 100% anhydrous DMSO at a final concentration of 10 mM. For conjugating the SH group of the cysteine residue with maleimide-PEG$_3$-DBCO (Conju-probe Inc., San Diego, USA) to create a functional linking group DBCO, the peptide and maleimide-PEG$_3$-DBCO were mixed at a 1/1 ratio and incubated at room temperature for 16 hours.

The identification of the synthesized DBCO-containing peptide 2 (illustrated below) was carried out by MALDI-TOF mass spectrometry.

In step (ii), the thus-synthesized DBCO-containing peptide 2 was then dissolved in dissolved in 100% DMSO at a final concentration of 10 mM. DBCO-containing peptide 2 and organic base DABCO were mixed at ⅕ molar ratio in 100% DMSO. Subsequently, NHS-PEG$_{12}$-Mal crosslinker was added to the DBCO-containing peptide 2 solution at a final molar ratio of 1/6 (DBCO-containing peptide 2: NHS-PEG$_{12}$-Mal) in 100% anhydrous DMSO. The reaction mixture was further incubated overnight at room temperature.

The DBCO-containing peptide 2 conjugated with three PEG$_{12}$-Mal linking arms (illustrated below) was purified by reversed-phase HPLC on a Supelco C18 column (250 mm×10 mm; 5 μm), using a mobile phase of acetonitrile and 0.1% trifluoroacetic acid, a linear gradient of 0% to 100% acetonitrile over 30 minutes, at a flow rate of 3.0 ml/min and a column temperature of 25° C.

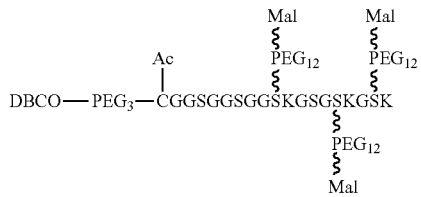

The mass spectroscopic analysis of the thus-synthesized DBCO-containing peptide 2 conjugated with three PEG$_{12}$-Mal linking arms indicated that the molecular construct had a m.w. of 4,480.89 daltons.

In step (iii), the thiol group of the somatostatin analog of Example 3 was reacted with a DBCO-containing peptide 2 conjugated with three PEG$_{12}$-Mal linking arms. The somatostatin analog was dissolved in 100% DMSO at a final concentration of 25 mM, while the DBCO-containing peptide 2 conjugated with three linking arms was dissolved in 100% DMSO at a 1 mM final concentration. The DBCO-containing peptide 2 conjugated with three PEG$_{12}$-Mal linking arms was added to the somatostatin solution at a final concentration of 3.6 mM (3.6-fold molar excess over 1 mM DBCO-containing peptide 2 multi-arm linker solution). The reaction mixture was incubated overnight at room temperature.

Figure 6A:
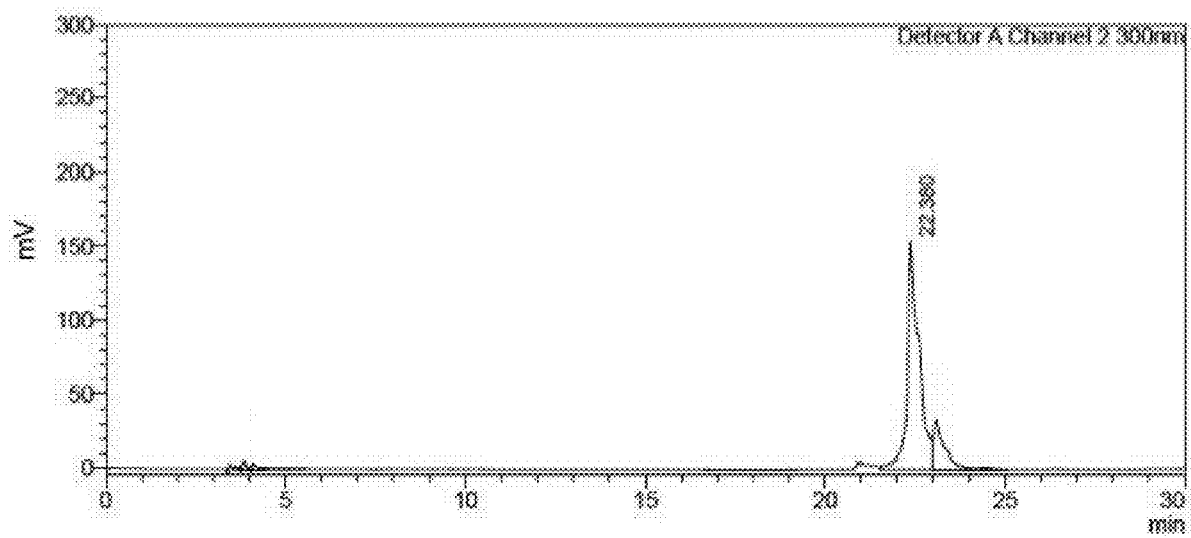
FIGS. 6A and 6B respectively show the reverse phase analytical HPLC profile and the MALDI-TOF result of DBCO-containing multi-arm linker unit conjugated with three somatostatin analogs, according to one example of the present disclosure.

The DBCO-containing multi-arm linker unit conjugated with three somatostatin analogs (3-somatostatin DBCO drug bundle) was purified by reversed-phase high-performance liquid chromatography (RP-HPLC) on a Supelco C18 column (250 mm×10 mm; 5 μm), using a mobile phase of acetonitrile and 0.1% trifluoroacetic acid, a linear gradient of 0% to 100% acetonitrile over 30 minutes, at a flow rate of 3.0 mL/min and a column temperature of 25° C. The elution profile of the reverse phase HPLC of 3-somatostatin DBCO drug bundle showed that the eluting peak thereof has a retention time of 22.38 minutes, monitored at OD254 nm by detection of UV absorbance, shown in FIG. 6A.

Figure 6B:
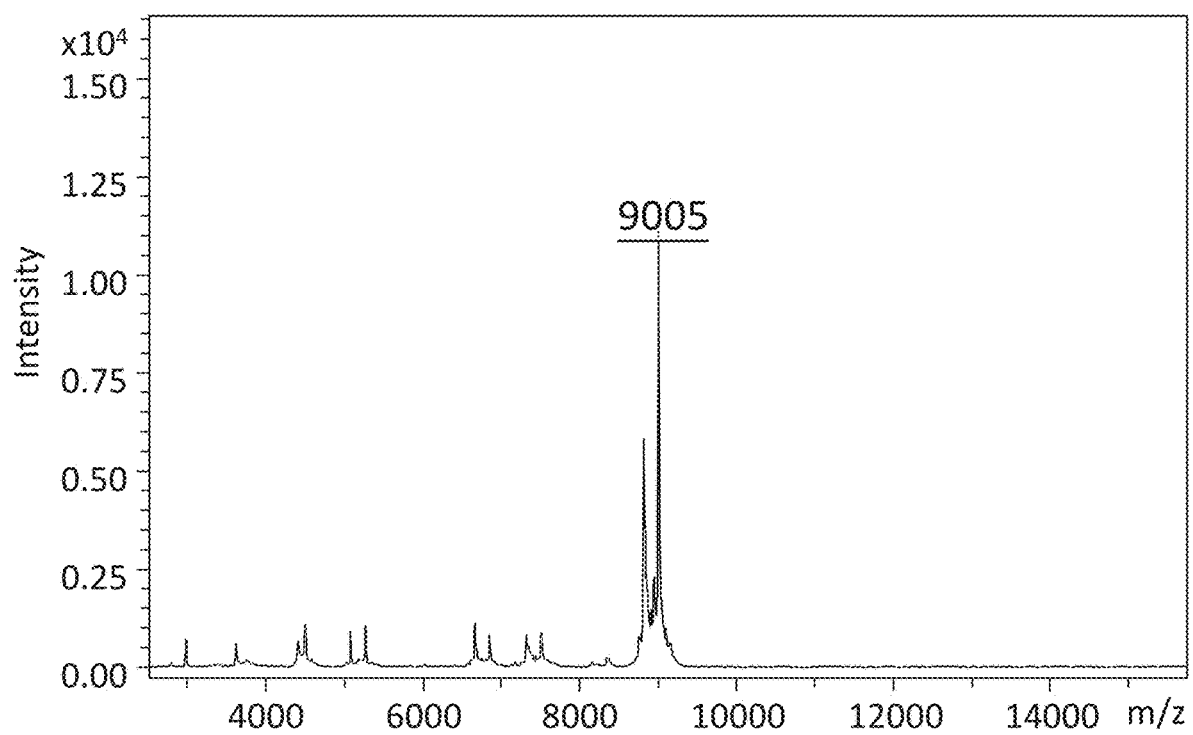

FIG. 6B shows that the result of mass spectroscopic analysis of the thus-synthesized 3-somatostatin DBCO drug bundle (illustrated below), indicated that the molecular construct had a m.w. of 9,005 daltons.

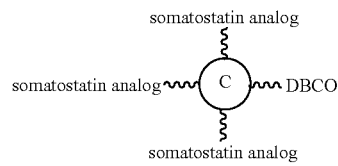

Example 5: Synthesis of Azide-Containing Multi-Arm Linker Unit with Peptide 3 as a Peptide Core (SEQ ID NO:5) with a Linking Arm Covalently Linked with the Octreotide Peptide (SEQ ID NO:6)

In this example, 3-octreotide azide-drug bundles were prepared using standard Fmoc chemistry by manual synthesis. The drug bundle is an azide-containing linker unit using the peptide 3 as a peptide core (SEQ ID NO:5) and three linking arms, each covalently linked with an octreotide peptide (SEQ ID NO:6). The inventors designed the linker unit and outsourced the production of the 3-octreotide azide-drug bundles to Shanghai WuXi AppTech Co., Ltd. (Shanghai, China).

The thus-synthesized molecule, as illustrated below, was composed of a multi-arm linker unit covalently linked with three octreotide and a free azide group. The identification of the samples was carried out by MALDI-TOF mass spectrometry.

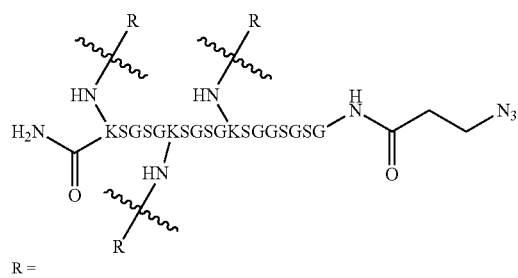

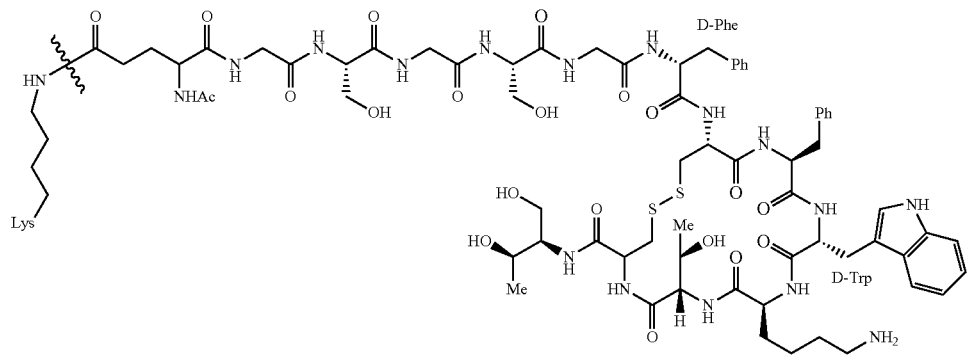

Example 6: Synthesis of an Alkyne-Containing Linker Unit Having Two Palmitoyl Chains as a Fatty Acid Bundle In this example, an alkyne-containing fatty acid bundle having two palmitoyl chains (illustrated below) was prepared.

4 EG repeats. Two palmitoyl chains were respectively linked to the K residues of the peptide center core via forming an amide bond between the $CO_2H$ group of the palmitic acid and the amine group of the K residue (illustrated below). The synthesis of this new molecule-"alkyne-$EG_4$-2FA-C16" (abbreviated as alkyne-2FA) was carried out by Shanghai WuXi AppTech Co., Ltd.

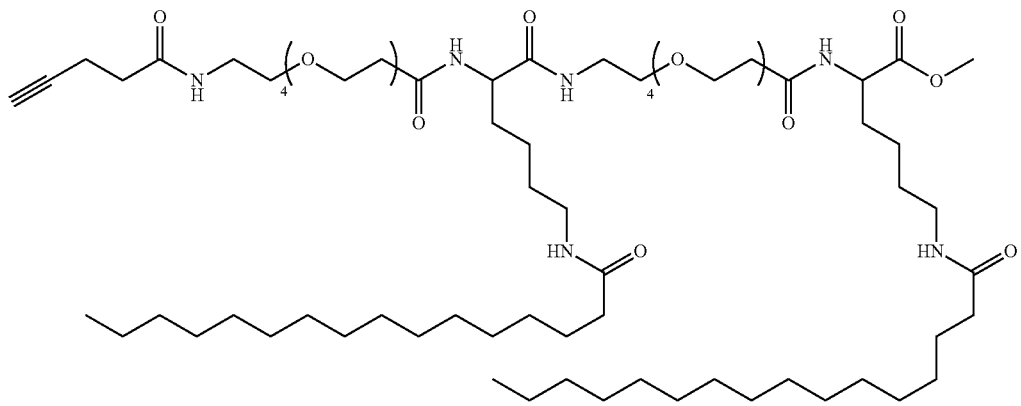

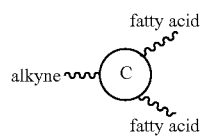

The peptide core (alkyne-ethyl-Xaaa-K-Xaaa-K-OMe, SEQ ID NO: 7) has two K residues and an alkynylpropionyl group disposed at its N-terminus. The filler between the two K residues and the N-terminal spacer between the alkyne group and the first K residue are PEGylated amino acid with In step (i), the peptide synthesis started by covalently linking the first amino acid onto the resin: the amino acid Fmoc-Lys(Dde)-OH (6.0 mmol) and CTC resin (3.0 mmole) were dissolved in dichloromethane (DCM), and then DIEA (12.0 mmole) was added and the resulting mixture was swelled for 2 hours under nitrogen gas bubbling.

In step (ii), the peptide-resin mixture solution was drained and washed with DMF 3 times. In step (iii), after washing of the resin, the Fmoc protecting group on CTC resin was removed by adding 20% piperidine in DMF solution for 30 minutes. In step (iv), the treated solution was drained and washed with DMF 5 times. In step (v), the manual coupling of the $2^{nd}$ amino acid was performed by adding Fmoc-$PEG_4$-

OH (2 equiv) and the activating agent (HBTU) onto the resin under nitrogen gas bubbling for about 1 hour. Next, steps (ii) to (v) were repeated each time with another amino acid according to peptide sequence. Dde protecting groups of two lysine residues were removed by adding 3% $N_2H_4$/DMF solution to peptide resin solution and incubating for 20 minutes. In the last cycle of synthesis, palmitic acid (1.0 equiv) was added and the activating agent (HBTU) onto the resin under nitrogen gas bubbling for about 1 hour.

For the cleavage of side-chain protected peptide from CTC resin, the cleavage buffer (95% TFA/2.5% TIPS/2.5% $H_2O$) was prepared and added to the flask containing the peptide-resin solution and stirring at room temperature for 1 hour. The crude peptide was precipitated into cold tert-butyl methyl ether and centrifuged for 2 minutes at 5000 rpm. The crude peptide was washed by Tert-butyl methyl ether two additional times and was dried under vacuum for 2 hours.

For preparing methyl ester of C-terminus, the crude peptide was dissolved in 4N HCl in MeOH solution. The solution was reacted for about 2 hours and monitored by liquid chromatography-mass spectrometry (LCMS). After the reaction was complete, the reaction was quenched by DIEA and adjusted pH value to 7.0. The resulting solution was dried under vacuo.

Figure 7:
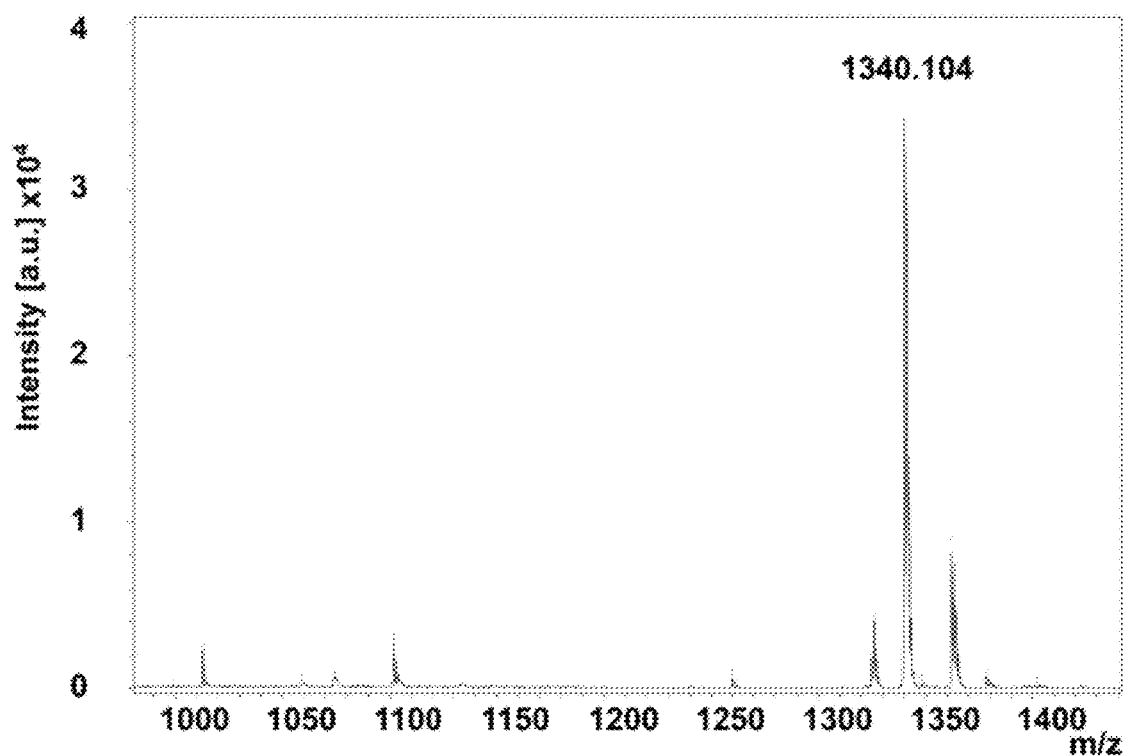
FIG. 7 shows the MALDI-TOF analysis of alkyne-containing linker unit with two palmityl chains, according to one example of the present disclosure.

The alkyne-containing linker unit having two palmitoyl chains was purified by reverse phase HPLC on a Luna preparative C4 column (250 mm×25 mm; 10 μm), using a mobile phase of acetonitrile and 0.075% trifluoroacetic acid, a linear gradient of 55% to 90% acetonitrile over 60 minutes, at a flow rate of 20 mL/min and a column temperature of 25° C. The mass spectroscopic analysis of the thus-synthesized alkyne-containing linker unit having two aliphatic chains, as provided in FIG. 7, indicated that the molecular construct had a m.w. of 1,340.104 daltons. Abbreviations: TIPS, triisopropylsilane.

Example 7: Synthesis of Four Alkyne-Containing Fatty Acid Bundles Inserted with an Additional Glutamate Residue as a Spacer Between Lys Residue and Aliphatic Chain in Peptide Central Core In this example, four additional alkyne-containing fatty acid bundles were prepared.

As illustrated below, one of the fatty acid bundles was called "alkyne-$EG_4$-2E-2FA-C16" having two palmitoyl chains was prepared. The peptide central core (alkyne-ethyl-Xaaa-K-Xaaa-K-OMe, SEQ ID NO: 7) has two lysine residues and an alkyne group disposed at its N-terminus. The spacers between the two lysine residues and between the alkyne-ethyl group and its adjacent lysine residue are PEGylated amino acid with 4 EG repeats. Two palmitoyl chains were respectively linked to the lysine residues of the peptide center core via additional glutamate spacers forming the amide bonds between the gamma-$CO_2H$ group of glutamate residue and the amine group of the lysine residue and between the alpha-amine group of glutamate residue and the $CO_2H$ group of palmitic acid.

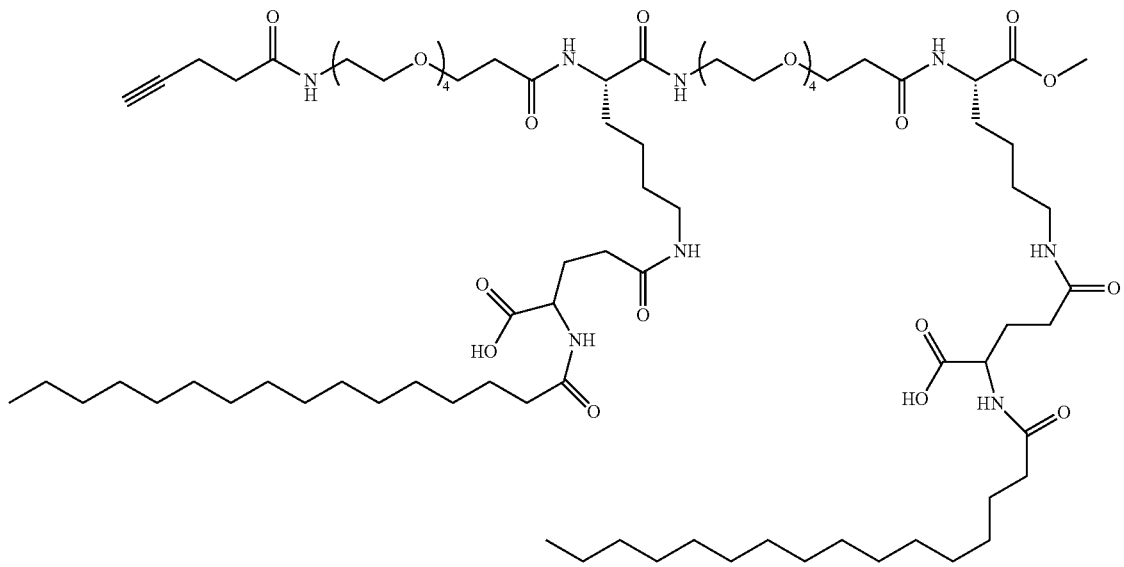

The alkyne-EG$_4$-2E-2FA-C16-acid fatty acid bundle (as illustrated below) was prepared. The peptide central core (alkyne-ethyl-Xaa$_4$-K-Xaa$_4$-K-OMe, SEQ ID NO: 7) has two lysine residues and an alkyne group disposed at its N-terminus. The spacers between the two lysine residues and between the alkyne group and its adjacent lysine residue are PEGylated amino acid with 4 EG repeats. Two palmitoyl chains with diacid groups (that is, a hexadecanedioic acid or thapsic acid) were respectively linked to the lysine residues of the peptide center core via additional glutamate spacers forming the amide bonds between the gamma-CO$_2$H group of glutamate residue and the amine group of the lysine residue and between the alpha-amine group of glutamate residue and one of the two CO$_2$H group of palmitic diacid.

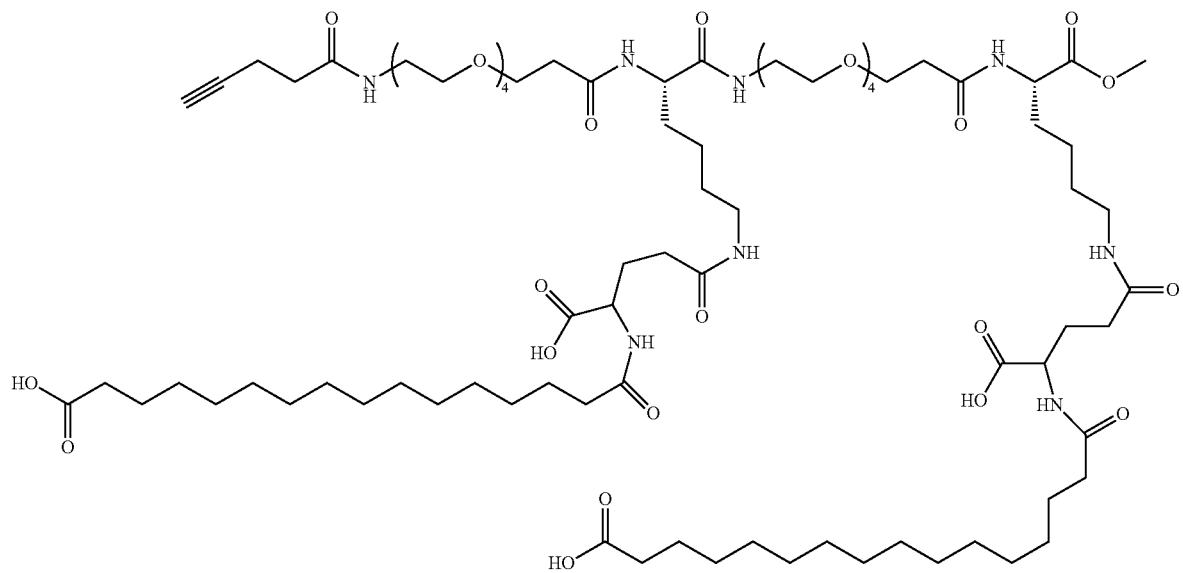

The alkyne-EG$_2$-2E-2FA-C16-acid fatty acid bundle (as illustrated below) was prepared. The peptide central core (alkyne-ethyl-Xaa$_2$-K-Xaa$_2$-K-OMe, SEQ ID NO:8) has two lysine residues and an alkyne group disposed at its N-terminus. The spacers between the two lysine residues and between the alkyne group and its adjacent lysine residue are PEGylated amino acid with 2 EG repeats. Two palmitoyl chains with diacid groups were respectively linked to the lysine residues of the peptide center core via additional glutamate spacers forming the amide bonds between the gamma-CO$_2$H group of glutamate residue and the amine group of the lysine residue and between the alpha-amine group of glutamate residue and one of the two CO$_2$H groups of palmitic diacid.

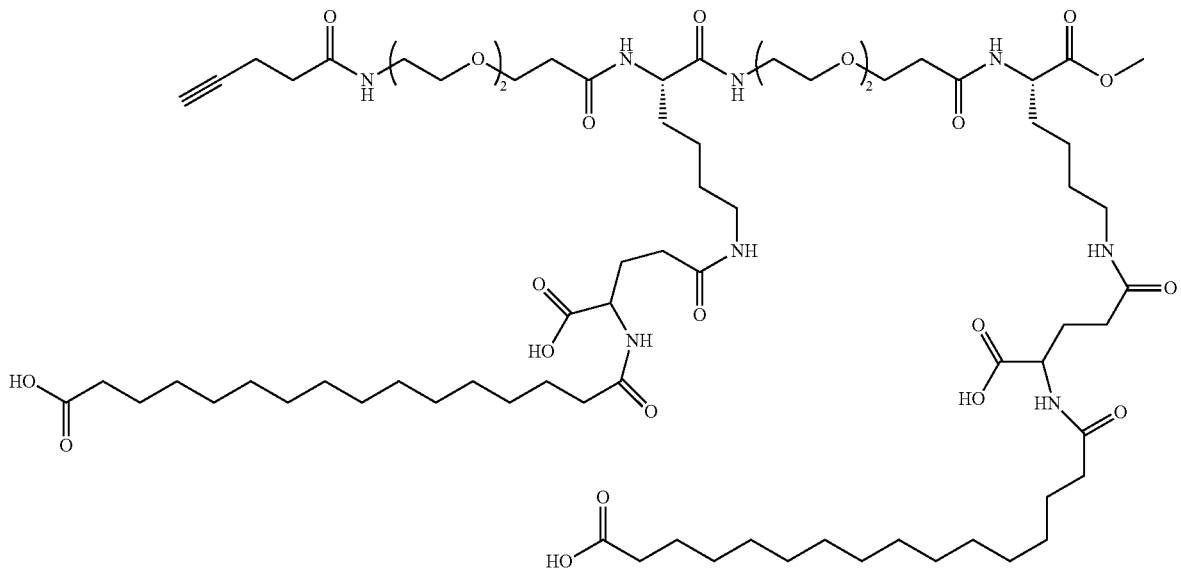

The alkyne-EG$_2$-2E-2FA-C18-acid fatty acid bundle (as illustrated below) was prepared. The peptide central core (alkyne-ethyl-Xaa$_2$-K-Xaa$_2$-K-OMe, SEQ ID NO:8) has two lysine residues and an alkyne group disposed at its N-terminus. The spacers between the two lysine residues and between the alkyne group and its adjacent lysine residue are PEGylated amino acid with 2 EG repeats. Two stearoyl chains with diacid groups (that is, an octadecanedioic acid) were respectively linked to the lysine residues of the peptide center core via additional glutamate spacers forming the amide bonds between the gamma-CO$_2$H group of glutamate residue and the amine group of the lysine residue and between the alpha-amine group of glutamate residue and one of the two CO$_2$H groups of octadecanedioic acid.

Gemini C18 (150 mm×30 mm; 5 μm) in series, using a mobile phase of acetonitrile and 0.075% trifluoroacetic acid, a linear gradient of 40% to 70% acetonitrile within 60 minutes, at a flow rate of 20 mL/min and a column temperature of 25° C. The product was lyophilized to give the desired product (33.2 mg, 2.85% yield) as a white solid.

Figure 8A:
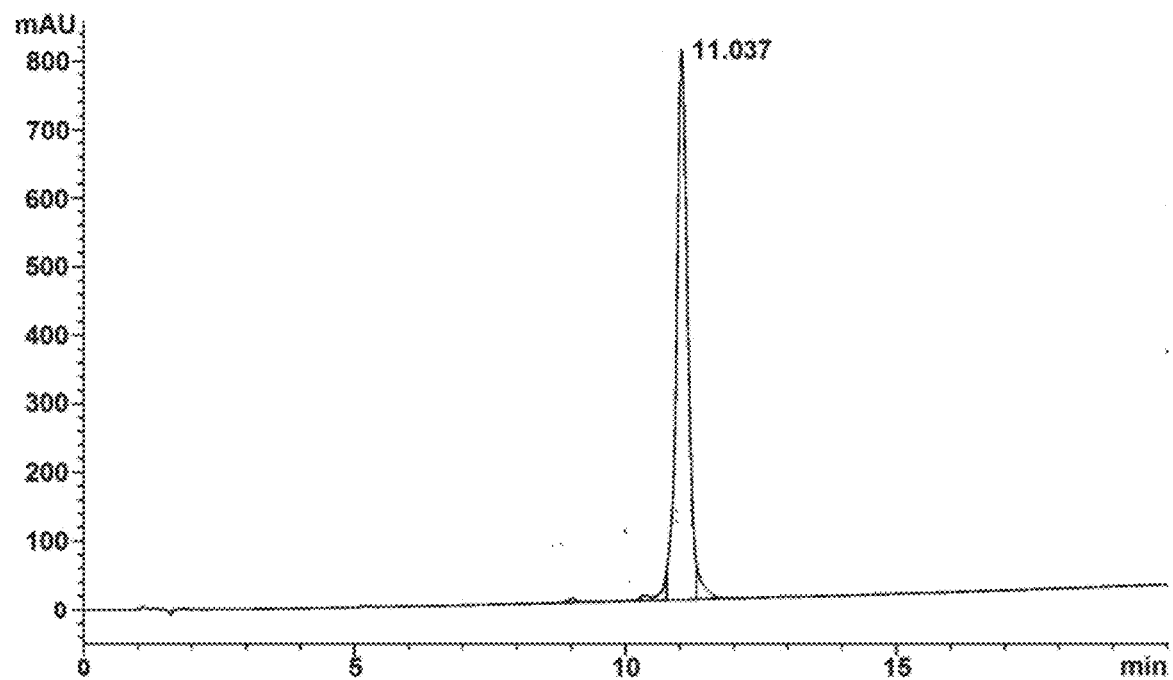
FIG. 8A and FIG. 8B respectively show the reverse phase analytical HPLC profile and the MALDI-TOF result of GLP-1-Ala$^8$-EG$_4$-2FA-C16 agonist, according to one example of the present disclosure.
Figure 8B:
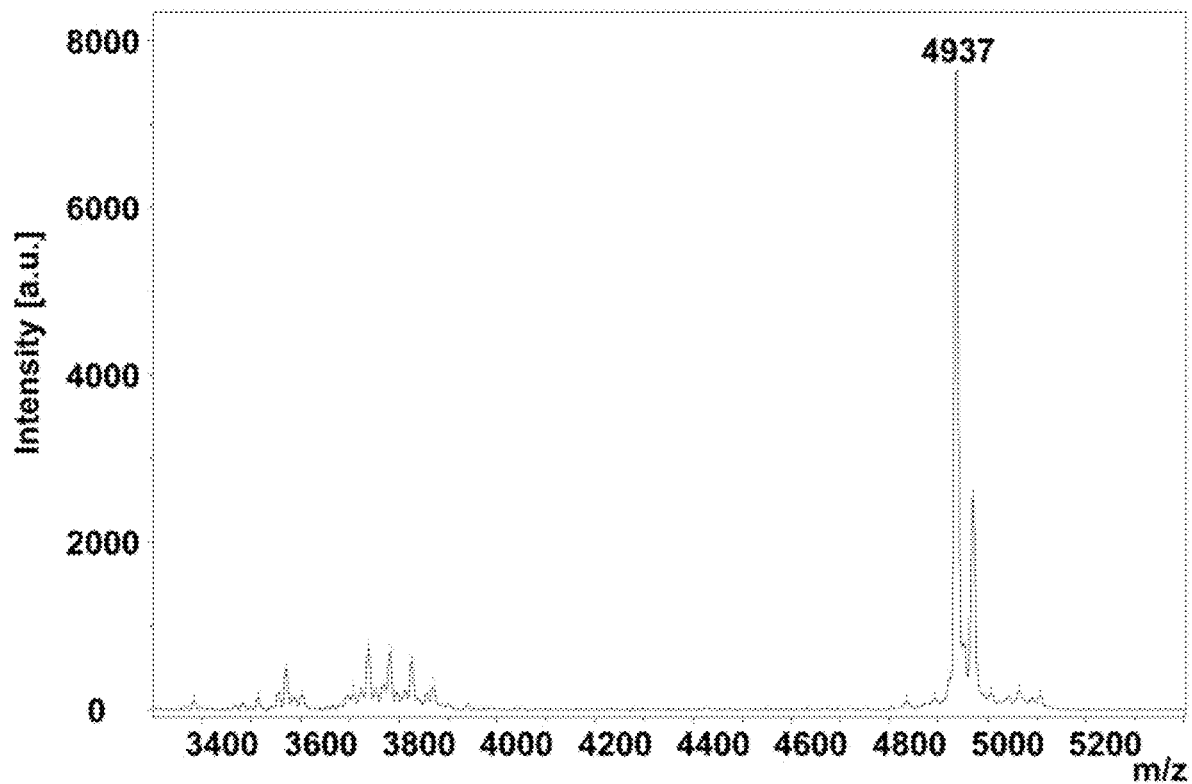

FIG. 8A depicted the reverse phase HPLC elution profile for the purification of GLP-1-2FA agonist, in which the peak of the GLP-1-2FA agonist appeared at OD 215 nm with a retention time of 11.037 minutes. The mass spectroscopic analysis of the thus-synthesized GLP-1-Ale$^8$-EG$_4$-2FA-C16 agonist, as provided in FIG. 8B, indicated that the molecular construct of GLP-1-Ala$^8$-EG$_4$-2FA-C16 agonist had a m.w. of 4,937 daltons.

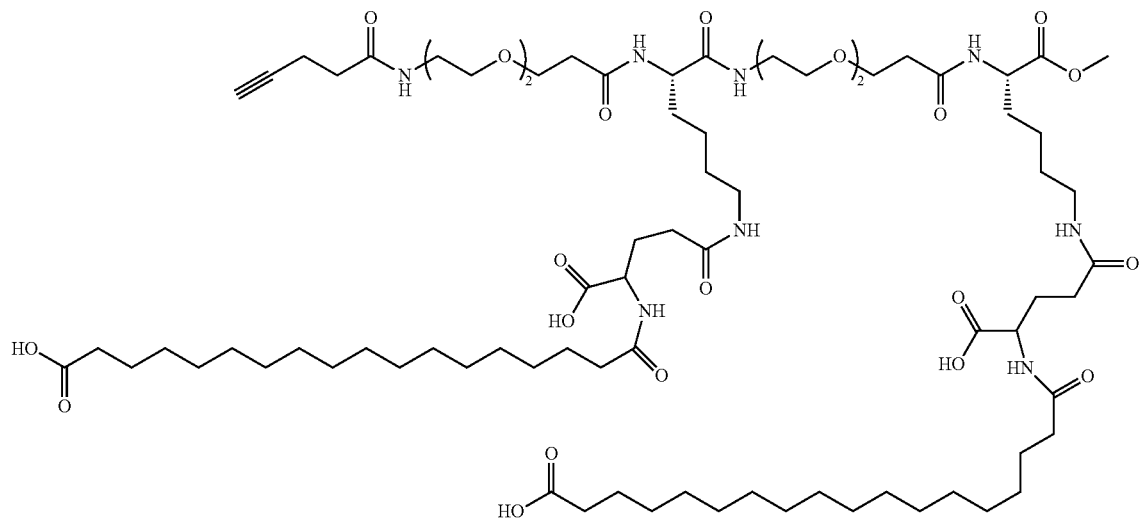

Similar to the Example 6, the syntheses of these four fatty acid bundle molecules-"alkyne-EG$_4$-2E-2FA-C16, alkyne-EG$_4$-2E-2FA-C16-acid, alkyne-EG$_2$-2E-2FA-C16-acid and alkyne-EG$_2$-2E-2FA-C18-acid" were outsourced to Shanghai WuXi AppTech Co., Ltd.

Example 8: Synthesis of Molecular Construct Composed of One GLP-1 Agonist and Two Aliphatic Chains (GLP-1-Ale-EG$_4$-2FA-C16 Agonist)

In this example, azide-containing GLP-1 agonist of Example 1 and alkyne-containing linker unit having two palmitoyl chains of Example 6 were coupled via CuAAC between azide and alkyne groups to produce "GLP-1-Ala$^8$-EG$_4$-2FA-C16 agonist".

The synthesis was outsourced to Shanghai WuXi AppTech Co., Ltd. Briefly, a mixture of azide-containing GLP-1 agonist of Example 1 (850.0 mg, 236.4 μmol, 1.0 equiv) and alkyne-containing linker unit having two palmitoyl chains of Example 6 (158.4 mg, 118.2 μmol, 0.5 equiv) in DMSO (30.0 mL) was degassed and purged with nitrogen gas for 3 times, CuI (22.5 mg, 118.2 μmol, 0.5 equiv) and DIEA (61.1 mg, 472.8 μmol, 82.4 μL, 2.0 equiv) were added, and the mixture was stirred at 25° C. for 1 hour under nitrogen gas atmosphere. Completion of the reaction was confirmed by liquid chromatography mass spectrum (LC-MS).

GLP-1-2FA agonist was purified by reverse phase HPLC on a Luna C18 column (200 mm×25 mm; 10 μm) and Example 9: Synthesis of Molecular Construct Composed of One GLP-1 Agonist and Two Palmitoyl Chains with Additional Glutamate Residues as Spacers (GLP-1-Ala$^8$-EG$_4$-2E-2FA-C16 Agonist)

In this example, azide-containing GLP-1 agonist of Example 1 and one of alkyne-containing fatty acid bundles (alkyne-EG$_4$-2E-2FA-C16) of Example 7 were coupled via CuAAC between azide and alkyne groups to produce "GLP-1-Ala$^8$-EG$_4$-2E-2FA-C16 agonist".

Similar to Example 8, the synthesis was outsourced to Shanghai WuXi AppTech Co., Ltd.

Figure 9A:
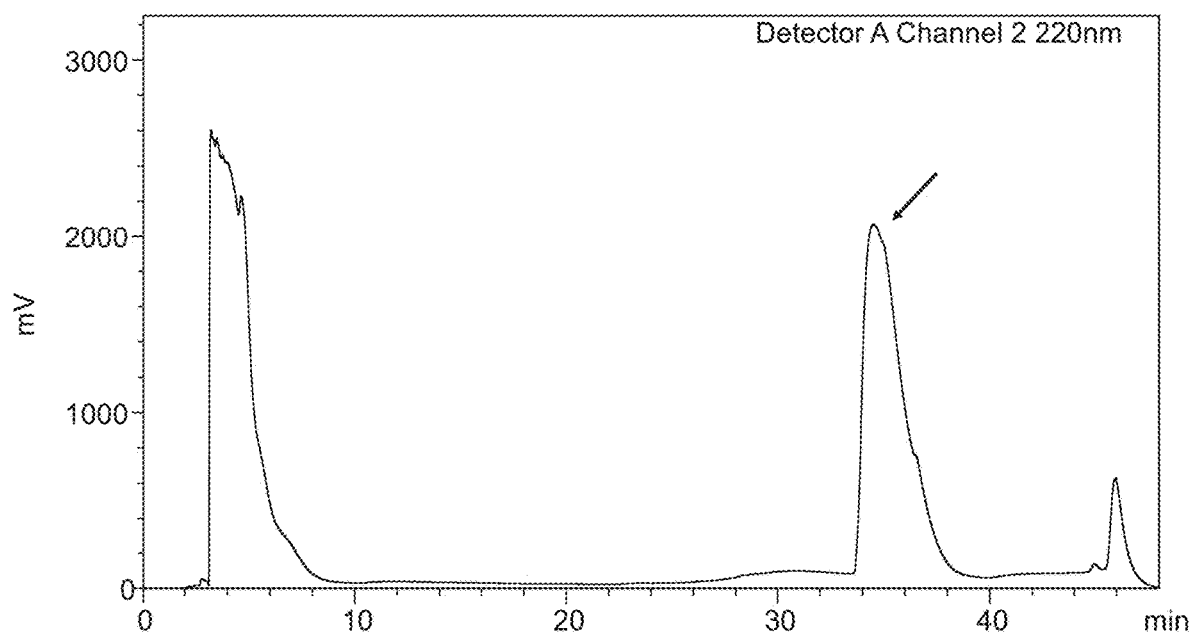
FIG. 9A and FIG. 9B respectively show the reverse phase analytical HPLC profile and the MALDI-TOF result of GLP-1-Ala$^8$-EG$_4$-2E-2FA-C16, according to one example of the present disclosure.

FIG. 9A depicted the reverse phase HPLC elution profile for the purification of GLP-1-Ala$^8$-EG$_4$-2E-2FA-C16 agonist, in which the peak of the GLP-1-EG$_4$-2E-2FA-C16 agonist appeared at OD 215 nm with a retention time of 34.53 minutes with the peak being indicated with an arrow.

Figure 9B:
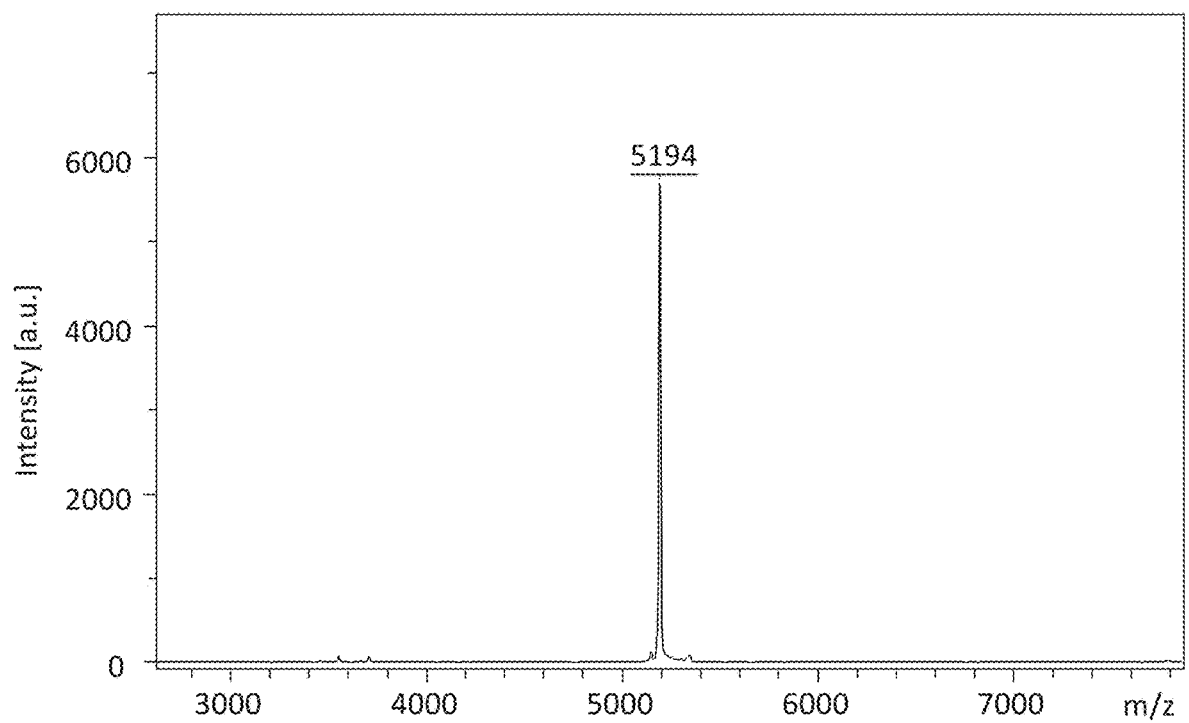

The mass spectroscopic analysis of the thus-synthesized GLP-1-EG$_4$-2E-2FA-C16 agonist, as provided in FIG. 9B, indicated that the molecular construct of GLP-1-Ale-EG$_4$-2E-2FA-C16 agonist had a m.w. of 5,194 daltons.

Example 10: Synthesis of Molecular Construct Composed of One Aib-Substituted GLP-1 Agonist and Two Palmitoyl Chains with Additional Glutamate Residues as Spacers (GLP-1-Aib$^8$-EG$_4$-2E-2FA-C16 Agonist)

In this example, Aib-substituted GLP-1 agonist having an azide group of Example 2 and one of alkyne-containing fatty acid bundles (alkyne-EG$_4$-2E-2FA-C16) of Example 7 were coupled via CuAAC between azide and alkyne groups to produce "GLP-1-Aib$^8$-EG$_4$-2E-2FA-C16 agonist".

Similar to Example 8, the synthesis was outsourced to Shanghai WuXi AppTech Co., Ltd.

Figure 10A:
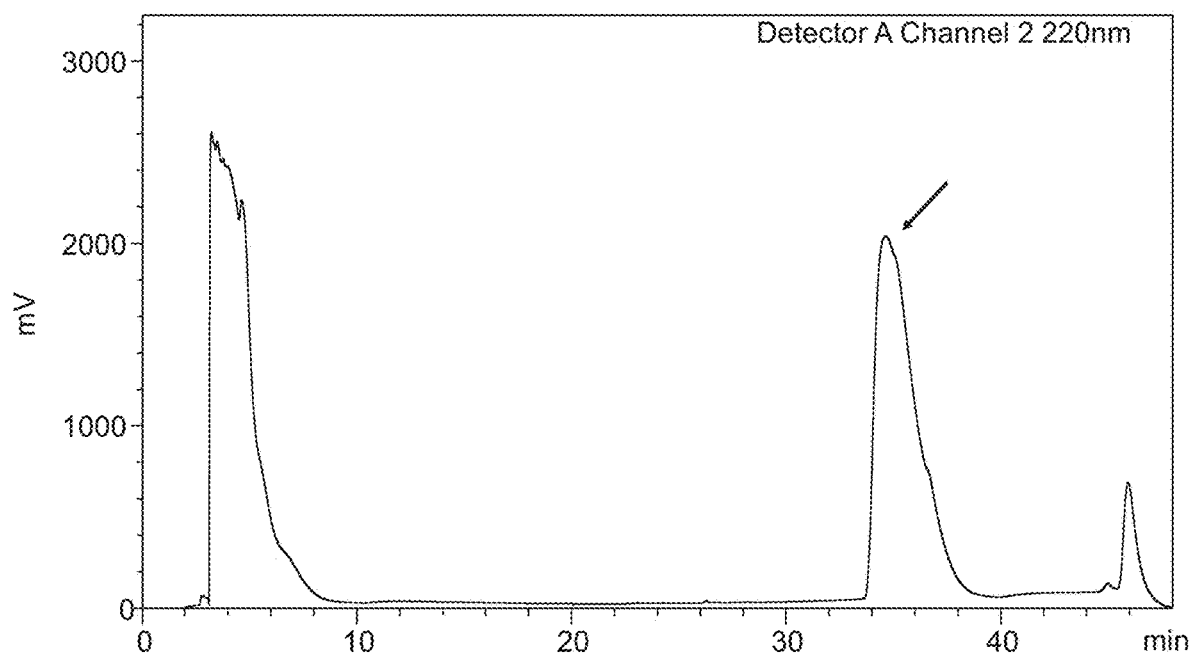
FIG. 10A and FIG. 10B respectively show the reverse phase analytical HPLC profile and the MALDI-TOF of GLP-1-Aib$^8$-EG$_4$-2E-2FA-C16 agonist, according to one example of the present disclosure.

FIG. 10A depicted the reverse phase HPLC elution profile for the purification of GLP-1-Aib$^8$-EG$_4$-2E-2FA-C16 agonist, in which the peak of the GLP-1-Aib-EG$_4$-2E-2FA-C16 agonist appeared at OD 215 nm with a retention time of 34.635 minutes with the peak being indicated with an arrow.

Figure 10B:
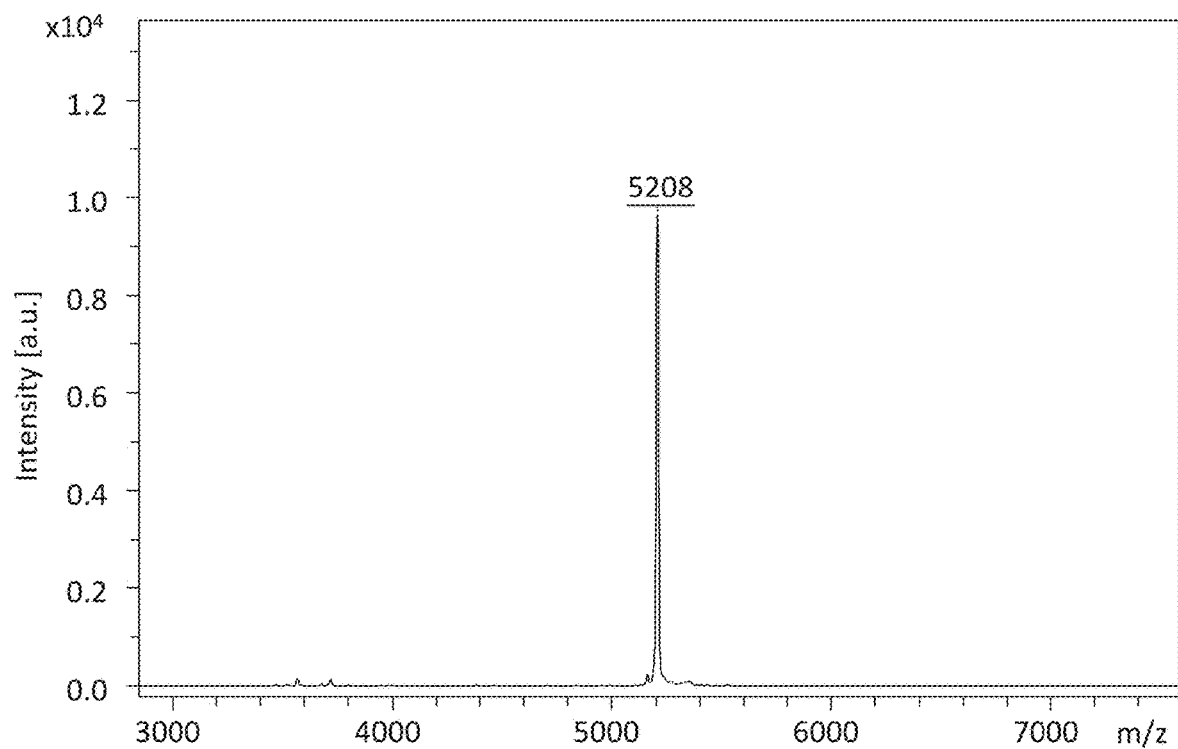

The mass spectroscopic analysis of the thus-synthesized GLP-1-Aib$^8$-EG$_4$-2E-2FA-C16 agonist, as provided in FIG. 10B, indicated that the molecular construct of GLP-1-Aib$^8$-EG$_4$-2E-2FA-C16 agonist had a m.w. of 5,208 daltons.

Example 11: Synthesis of Molecular Construct Composed of One Aib-Substituted GLP-1 Agonist and Two Palmitoyl Diacid Chains with Additional Glutamate Residues as Spacers (GLP-1-Aib$^8$-EG$_4$-2E-2FA-C16-Acid Agonist)

In this example, Aib-substituted GLP-1 agonist having an azide group of Example 2 and one of alkyne-containing fatty acid bundles (alkyne-EG$_4$-2E-2FA-C16-acid) of Example 7 were coupled via CuAAC between azide and alkyne groups to produce "GLP-1-Aib$^8$-EG$_4$-2E-2FA-C16-acid agonist".

Similar to Example 8, the synthesis was outsourced to Shanghai WuXi AppTech Co., Ltd.

Figure 11A:
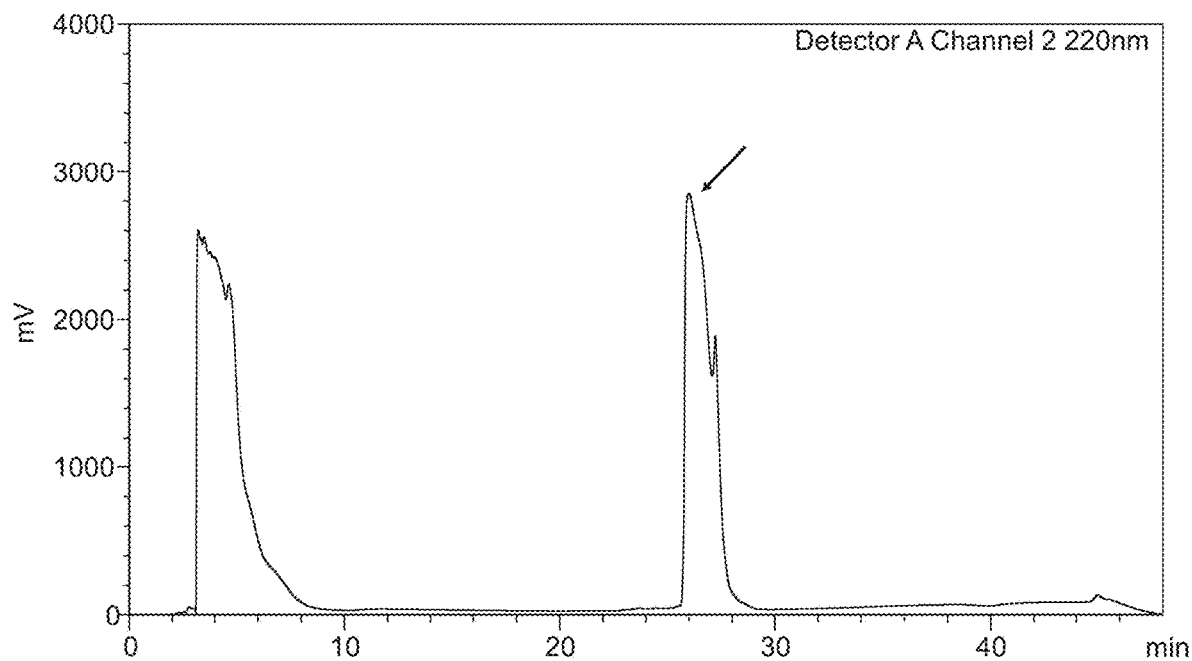
FIG. 11A and FIG. 11B respectively show the reverse phase analytical HPLC profile and the MALDI-TOF of GLP-1-Aib$^8$-EG$_4$-2E-2FA-C16-acid agonist, according to one example of the present disclosure.

FIG. 11A depicted the reverse phase HPLC elution profile for the purification of GLP-1-Aib$^8$-EG$_4$-2E-2FA-C16-acid agonist, in which the peak of the GLP-1-Aib$^8$-EG$_4$-2E-2FA-C16-acid agonist appeared at OD 215 nm with a retention time of 25.988 minutes with the peak being indicated with an arrow.

Figure 11B:
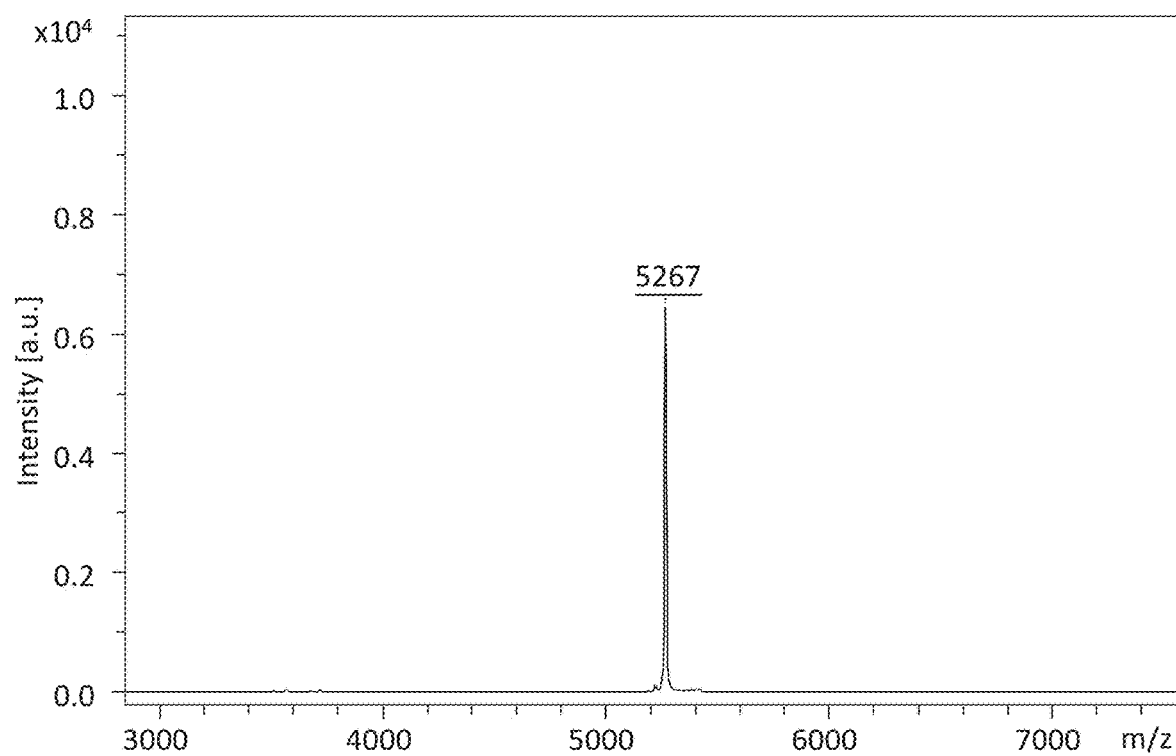

The mass spectroscopic analysis of the thus-synthesized GLP-1-Aib$^8$-EG$_4$-2E-2FA-C16-acid agonist, as provided in FIG. 11B, indicated that the molecular construct of GLP-1-Aib$^8$-EG$_4$-2E-2FA-C16-acid agonist had a m.w. of 5,267 daltons.

Example 12: Synthesis of Molecular Construct Composed of One Aib-Substituted GLP-1 Agonist and Two Palmitoyl Diacid Chains with Additional Glutamate Residues as Spacers (GLP-1-Aib$^8$-EG$_2$-2E-2FA-C16-Acid Agonist)

In this example, Aib-substituted GLP-1 agonist having an azide group of Example 2 and one of alkyne-containing fatty acid bundles (alkyne-EG$_2$-2E-2FA-C16-acid) of Example 7 were coupled via CuAAC between azide and alkyne groups to produce "GLP-1-Aib$^8$-EG$_2$-2E-2FA-C16-acid agonist".

Similar to Example 8, the synthesis was outsourced to Shanghai WuXi AppTech Co., Ltd.

Figure 12A:
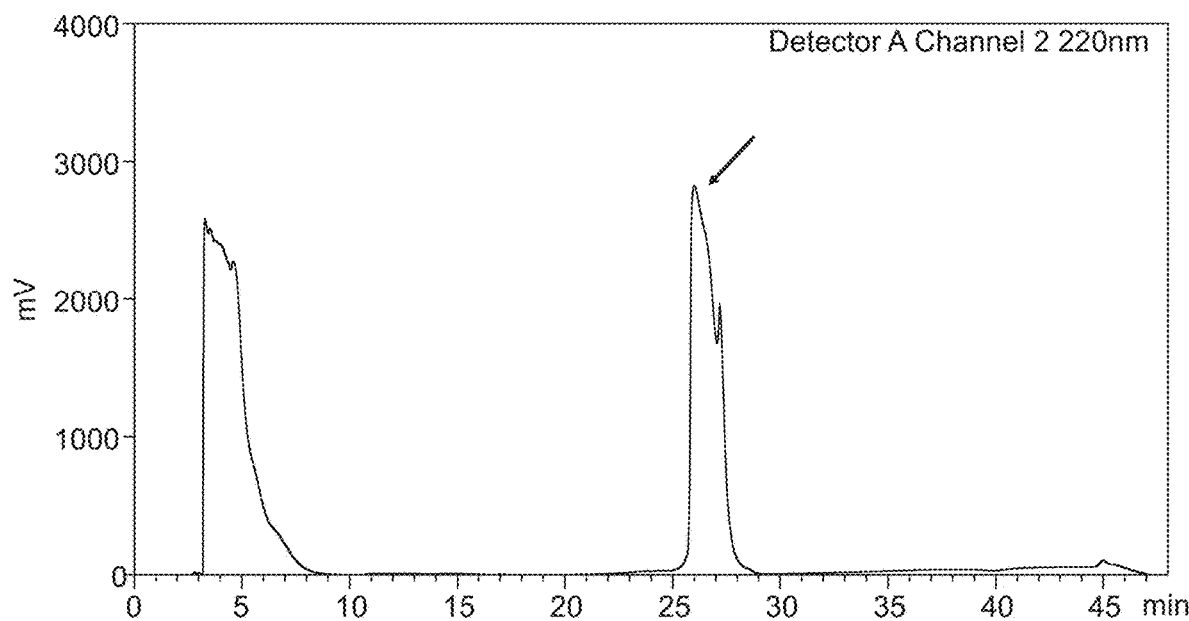
FIG. 12A and FIG. 12B respectively show the reverse phase analytical HPLC profile and the MALDI-TOF of GLP-1-Aib$^8$-EG$_2$-2E-2FA-C16-acid agonist, according to one example of the present disclosure.

FIG. 12A depicted the reverse phase HPLC elution profile for the purification of GLP-1-Aib$^8$-EG$_2$-2E-2FA-C16-acid agonist, in which the peak of the GLP-1-Aib$^8$-EG$_2$-2E-2FA-C16-acid agonist appeared at OD 215 nm with a retention time of 26.0 minutes with the peak being indicated with an arrow.

Figure 12B:
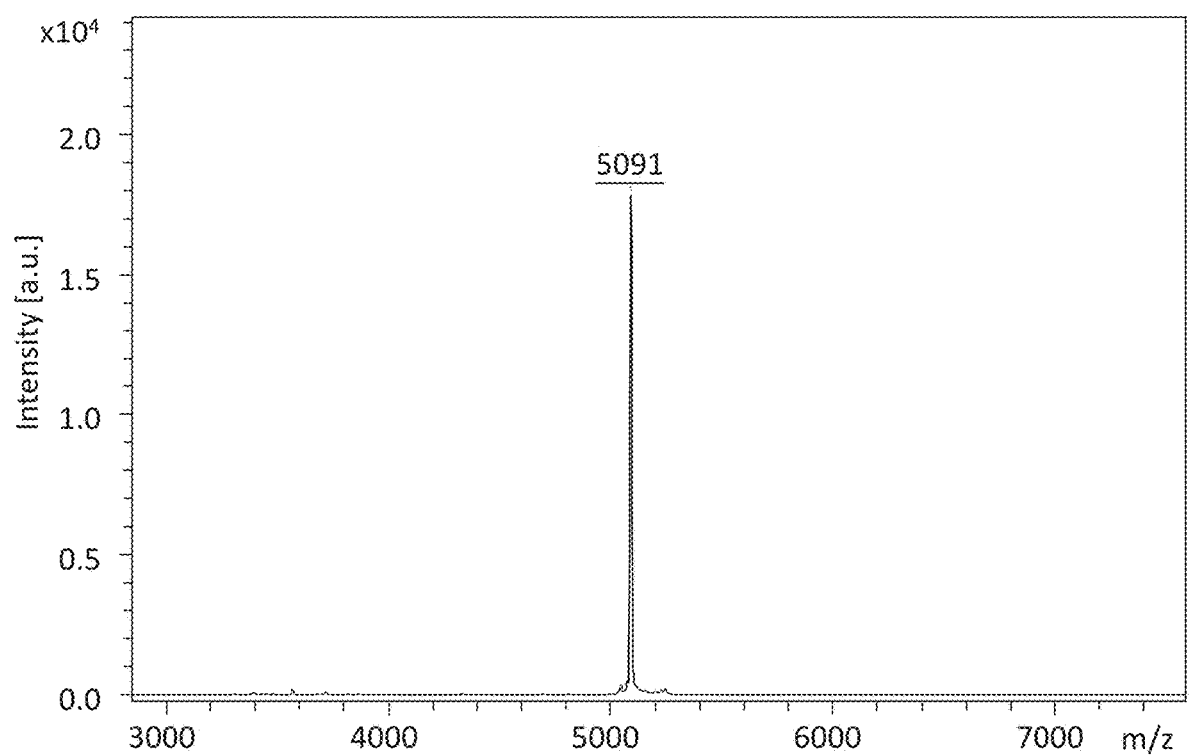

The mass spectroscopic analysis of the thus-synthesized GLP-1-Aib$^8$-EG$_4$-2E-2FA-C16-acid agonist, as provided in FIG. 12B, indicated that the molecular construct of GLP-1-Aib$^8$-EG$_2$-2E-2FA-C16-acid agonist had a m.w. of 5,091 daltons.

Example 13: Synthesis of Molecular Construct Composed of One Aib-Substituted GLP-1 Agonist and Two Stearoyl Diacid Chains with Additional Glutamate Residues as Spacers (GLP-1-Aib$^8$-EG$_2$-2E-2FA-C18-Acid Agonist)

In this example, Aib-substituted GLP-1 agonist having an azide group of Example 2 and one of alkyne-containing fatty acid bundles (alkyne-EG$_2$-2E-2FA-C18-acid) of Example 7 were coupled via CuAAC between azide and alkyne groups to produce "GLP-1-Aib$^8$-EG$_2$-2E-2FA-C18-acid agonist".

Similar to Example 8, the synthesis was outsourced to Shanghai WuXi AppTech Co., Ltd.

Figure 13A:
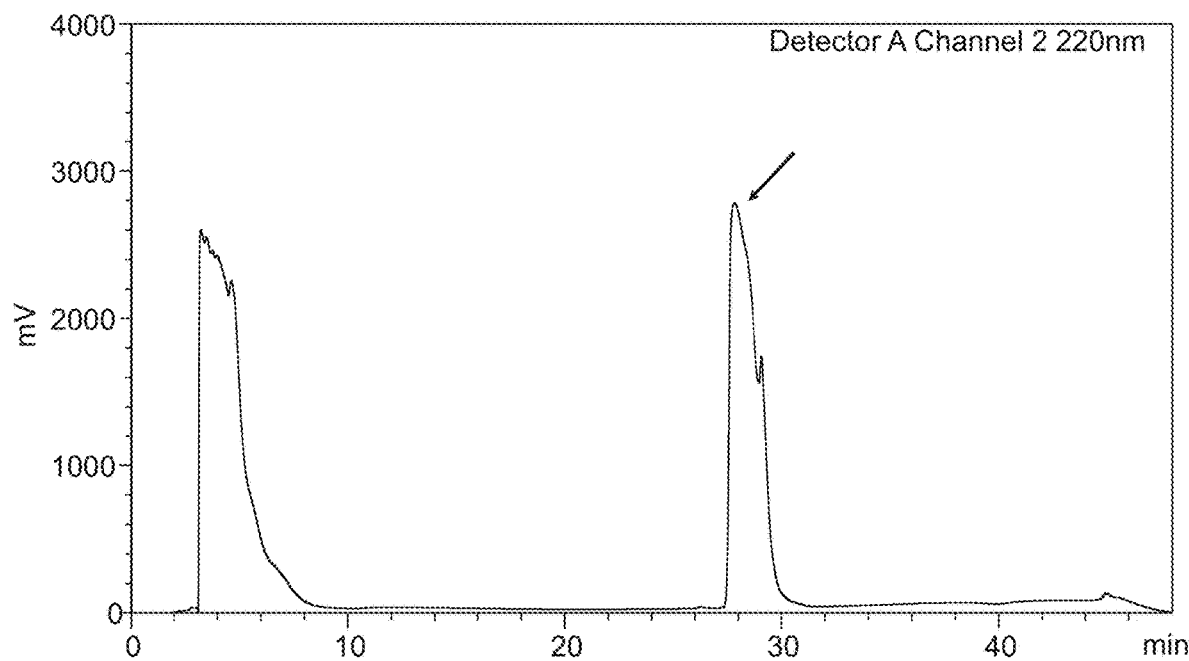
FIG. 13A and FIG. 13B respectively show the reverse phase analytical HPLC profile and the MALDI-TOF of GLP-1-Aib$^8$-EG$_2$-2E-2FA-C18-acid agonist, according to one example of the present disclosure.

FIG. 13A depicted the reverse phase HPLC elution profile for the purification of GLP-1-Aib$^8$-EG$_2$-2E-2FA-C18-acid agonist, in which the peak of the GLP-1-Aib$^8$-EG$_2$-2E-2FA-C18-acid agonist appeared at OD 215 nm with a retention time of 27.815 minutes with the peak being indicated with an arrow.

Figure 13B:
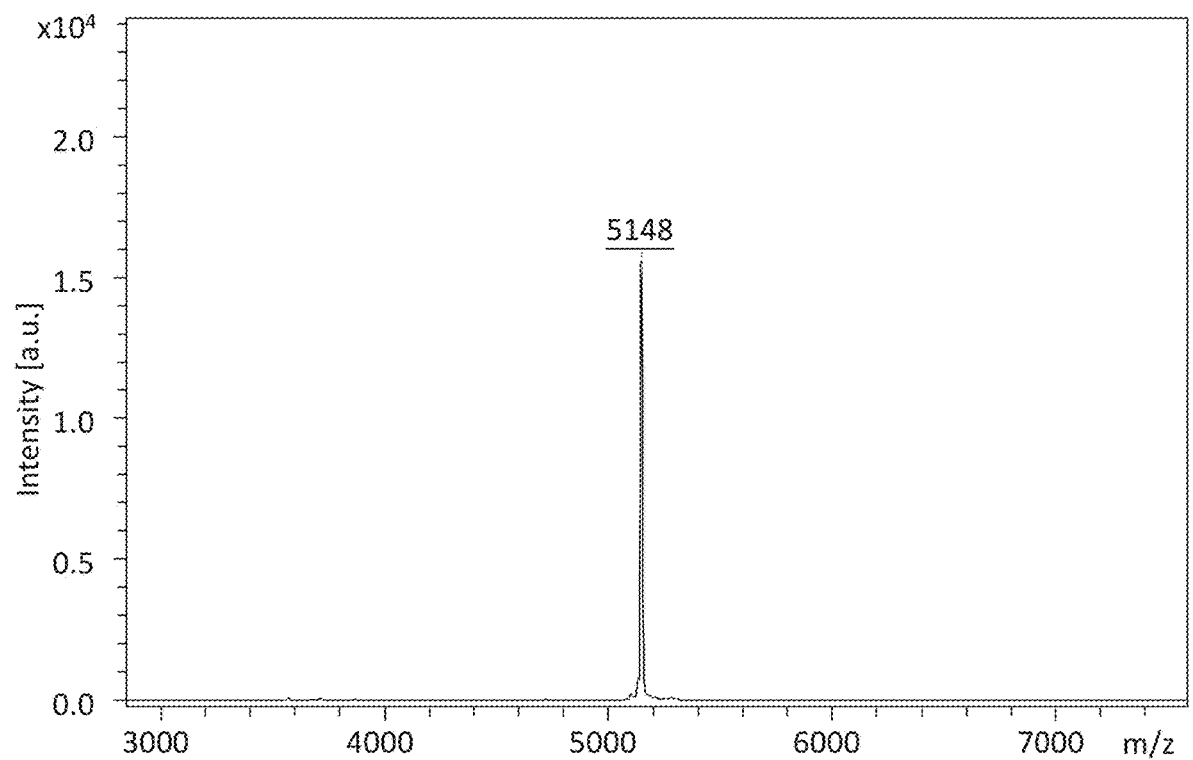

The mass spectroscopic analysis of the thus-synthesized GLP-1-Aib$^8$-EG$_4$-2E-2FA-C18-acid agonist, as provided in FIG. 13B, indicated that the molecular construct of GLP-1-Aib$^8$-EG$_2$-2E-2FA-C18-acid agonist had a m.w. of 5,148 daltons.

Example 14: Synthesis of Molecular Construct Composed of Multi-Arm Linker Unit Conjugated with Three Octreotide Peptides and Two Aliphatic Chains In this example, azide-containing multi-arm linker unit conjugated with three octreotide peptides of Example 5 and one of alkyne-containing fatty acid bundle (alkyne-EG$_4$-2E-2FA-C16) of Example 7 were coupled via CuAAC between azide and alkyne groups to produce a molecular construct composed of multi-arm linker unit conjugated with three octreotide peptides and two aliphatic chains, which is illustrated below.

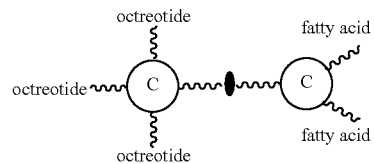

The procedures for synthesis were similar to the procedures described in the Example 8. Briefly, a mixture of azide-containing multi-arm linker unit conjugated with three octreotide peptides of Example 5 (1.0 equiv) and alkyne-containing linker unit having two palmityl chains of Example 7 (alkyne-EG$_4$-2E-2FA-C16) (0.5 equiv) in DMSO (30.0 mL) was degassed and purged with nitrogen gas for 3 times, CuI (0.5 equiv) and DIEA (2.0 equiv) were added, and the mixture was stirred at 25° C. for 1 hour under nitrogen gas atmosphere. Completion of the reaction was confirmed by LC-MS.

The thus-synthesized molecule, as illustrated below, was composed of multi-arm linker unit conjugated with three octreotide peptides and two aliphatic chains.

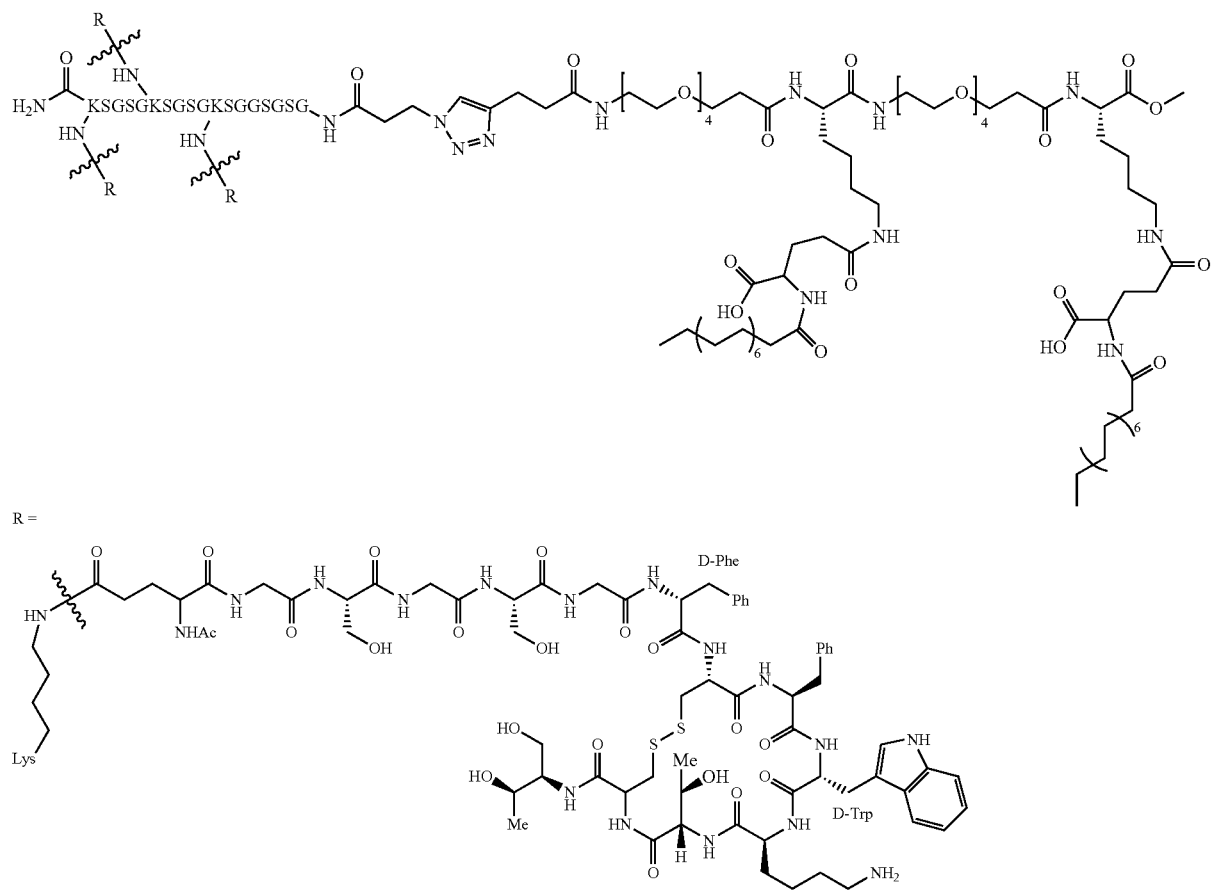

Example 15: Characterizing the Binding of GLP-1-EG₄-2FA-C16 Agonist to GLP-1 Receptor In this example, the binding ability of GLP-1-Ala$^8$-EG$_4$-2FA-C16 agonist (abbreviated as GLP-1-2FA) to GLP-1 receptor was investigated by use of ELISA.

Figure 14:
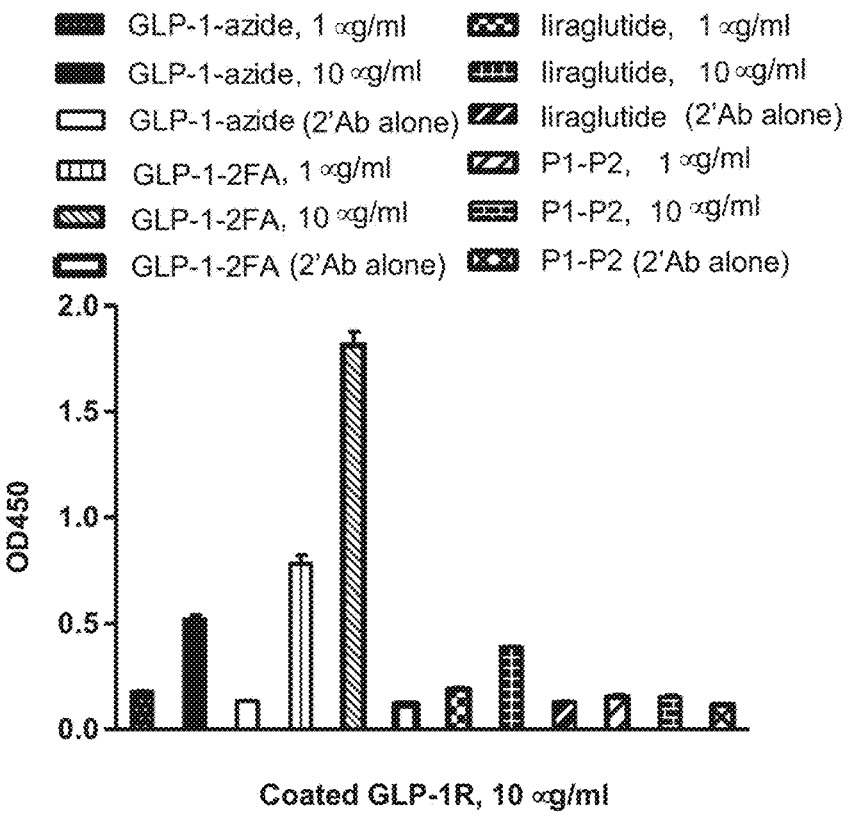
FIG. 14 is the result of ELISA analysis that depicts the binding affinity of 2FA-GLP-1 agonist to GLP-1 receptor, in which the GLP-1R-IgG.Fc fusion protein is coated on a microtiter plate followed by addition of azide-containing GLP-1 agonist (GLP-1-azide), 2FA-GLP-1 agonist (2FA-GLP-1), liraglutide, and control peptide (P1-P2 peptide, GLAGGSAQSQRAPDRVLCHSGQQQGL-PRAAGGSVPHPR, SEQ ID NO: 3) at a final concentration of 1 or 10 µg/ml, according to one example of the present disclosure.

Briefly, a 96-well microtiter plate was coated with recombinant human GLP-1R-IgG.Fc fusion protein (GLP-1R) (purchased from Sino Biological Inc., Taipei, Taiwan), at the concentration of 10 μg/ml, 50 μl per well. After washing off the excess recombinant GLP-1 receptor protein, the wells were blocked with 1% BSA in PBS, pH7.4 containing 0.1% NaN$_3$ for 1 hour, 50 μl per well of GLP-1-EG$_4$-2FA-C16 agonist, alkyne-containing linker unit having two palmitoyl chains (alkyne-EG$_4$-2FA-C16, abbreviated as alkyne-2FA), azide-containing GLP-1 agonist (GLP-1-azide), and liraglutide (Victoza, a gift from Dr. Yi-Cheng Chang, Graduate Institute of Medical Genomics and Proteomics, National Taiwan University) at two concentrations (1 μg/ml and 10 μg/ml) were added. After washing with PBS, mouse mAb IgG anti-hGLP-1 (Abcam, Bristol, UK) at a final concentration of 2 μg/ml was added and incubated at 37° C. for 1 hour. After washing with PBS, pH7.4, the hGLP-1-bound antibodies were detected by HRP-conjugated goat anti-mouse IgG(H+L) (Jackson ImmunoResearch) at 1:10,000 and incubated for 30 minutes at 37° C., followed by incubation with TMB substrate (Clinical Science Products, Mansfield, USA). The reaction was stopped by the addition of 50 μl of 1 M HCl. Absorbance at 450 nm was measured with a plate reader. Each bar represented the mean OD450 value of duplicate samples. The data showed that the GLP-1-2FA agonist could specifically bind to recombinant GLP-1 receptor (see FIG. 14). P1-P2 peptide, which is a segment from the CEmX domain of human membrane bound IgE, served as a negative control.

Example 16: Characterizing the Binding of GLP-1-Ale-EG₄-2FA-C16 Agonist and Human Serum Albumin (HSA)

In this example, the binding ability of GLP-1-Ala$^8$-EG$_4$-2FA-C16 agonist (abbreviated as GLP-1-2FA) to HSA, was investigated using ELISA.

Figure 15:
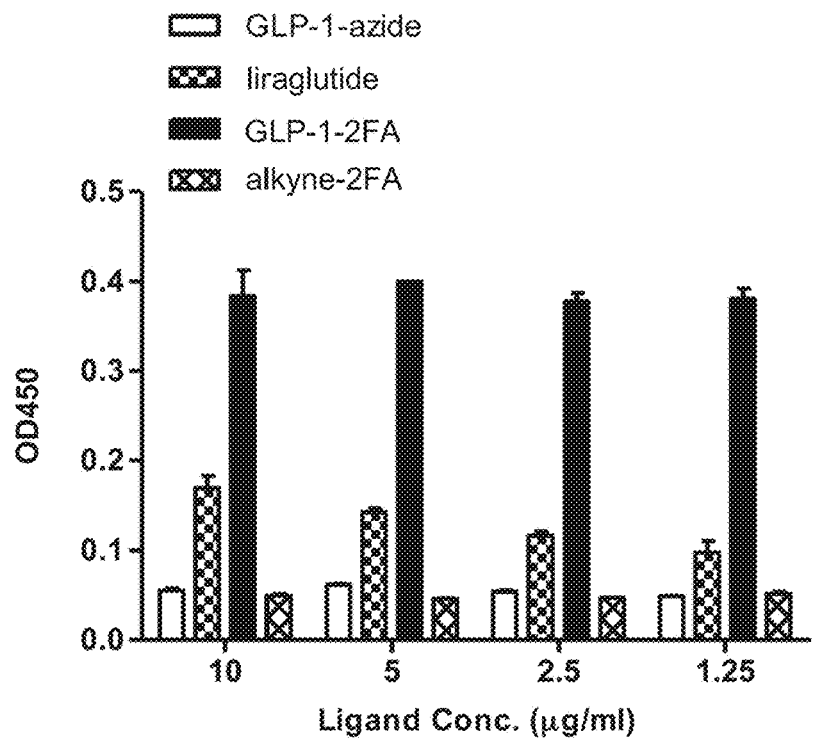
FIG. 15 is the result of ELISA analysis that depicts the binding affinity of 2FA-GLP-1 agonist to human serum albumin (HSA), in which the HSA is coated on a microtiter plate followed by addition of azide-containing GLP-1 agonist (GLP-1-azide), liraglutide, 2FA-GLP-1 agonist (2FA-GLP-1) and alkyne-containing 2FA (Alkyne-2FA), according to one example of the present disclosure.

Briefly, a 96-well microtiter plate was coated with HSA protein in 10 μg/ml concentration, 50 μl per well in 1×PBS, pH7.4 at 37° C. for 1 hour. The wells were then blocked with 1% casein in PBS, pH7.4 containing 0.1% NaN$_3$ for 1 hour and incubated with an azide-containing GLP-1 agonist (GLP-1-azide), alkyne-EG$_4$-2FA-C16 (alkyne-2FA), liraglutide, or GLP-1-2FA agonist at a final concentration of 1 and 10 μg/ml at 37° C. for 1 hour. After washing with PBS, pH7.4, mouse anti-hGLP-1 mAb (Abcam) at a final concentration of 10 μg/ml were added and incubated at 37° C. for 1 hour. After washing with PBS, pH7.4, the hGLP-1-bound antibodies was detected by HRP-conjugated goat anti-mouse IgG(H+L) antibodies (Jackson ImmunoResearch) at 1:10,000 and incubated for 30 minutes at 37° C., followed by incubation with TMB substrate (Clinical Science Products). The reaction was stopped by adding 50 μl of 1 M HCl. Absorbance at 450 nm was measured with a plate reader. Each bar represents the mean OD450 value of duplicate samples. It was found that the GLP-1-2FA exhibited a higher binding activity to HSA than liraglutide (FIG. 15). GLP-1-azide, alkyne-2FA and secondary antibody alone, served as negative controls.

Example 17: Characterizing Albumin-Binding Activity of GLP-1-Ala$^8$-EG$_4$-2FA-C16 Agonist to H SA Using Dialysis Equilibrium Analysis To further examine the binding ability of GLP-1-Ala$^8$-EG$_4$-2FA-C16 agonist (GLP-1-2FA) to HSA in aqueous solution, dialysis-equilibrium analysis was performed using a Float-A-Lyzer G2 Dialysis Device CE (Spectrum Europe B.V., Breda, The Netherlands), which contained 150 μM of 0.2 ml HSA incubation solution with the 30 μM of liraglutide or the GLP-1-2FA agonist. Dialysis sacs had a diameter of 5 mm, an inner volume of 1 ml and a m.w. cut-off of 20 kDa, which allows passage of liraglutide (m.w. 3,751.2 daltons) or the GLP-1-2FA agonist (m.w. 4,937 daltons) in and out of the dialysis sac. The dialysis device was placed in a chamber filled with 4 ml buffer incubation solution and placed on a shaker at room temperature for overnight. One-tenth volume of incubation solution and pre-dialysis control were loaded onto the modified tricine SDS-PAGE. HSA-bound GLP-1-2FA agonist or liraglutide at equilibrium were visualized and quantified by Coomassie-blue stain, to compare the relative binding ability of GLP-1-2FA agonist to HSA, and liraglutide to HSA.

Figure 16A:
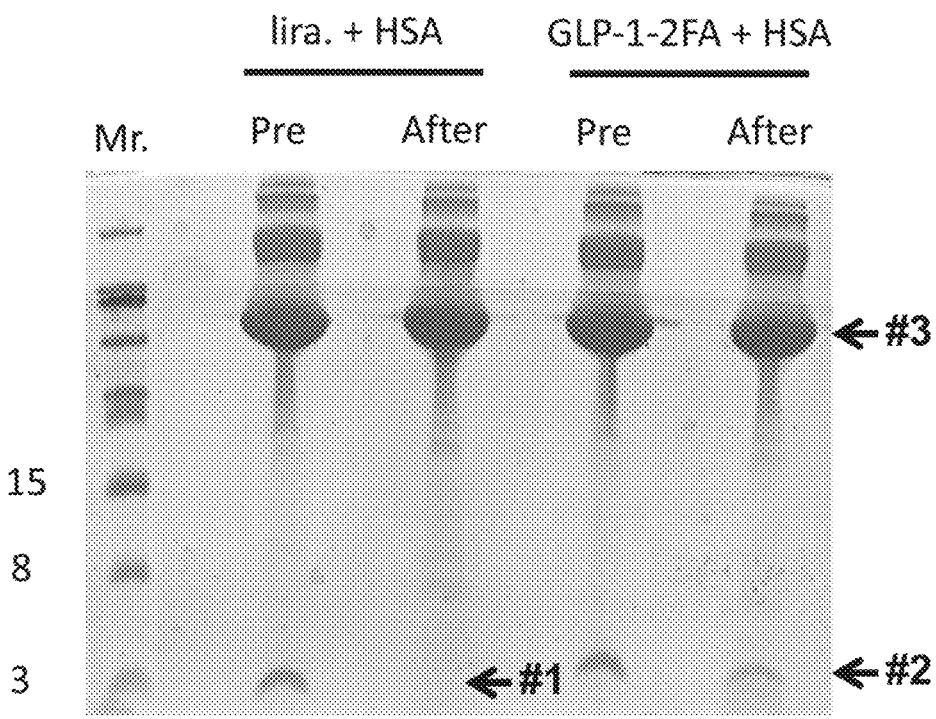
FIGS. 16A and 16B respectively depict the binding affinity of 2FA-GLP-1 agonist to HSA using dialysis equilibrium analysis and the percentage of 2FA-GLP-1 agonist and liraglutide bound to HSA.
Figure 16B:
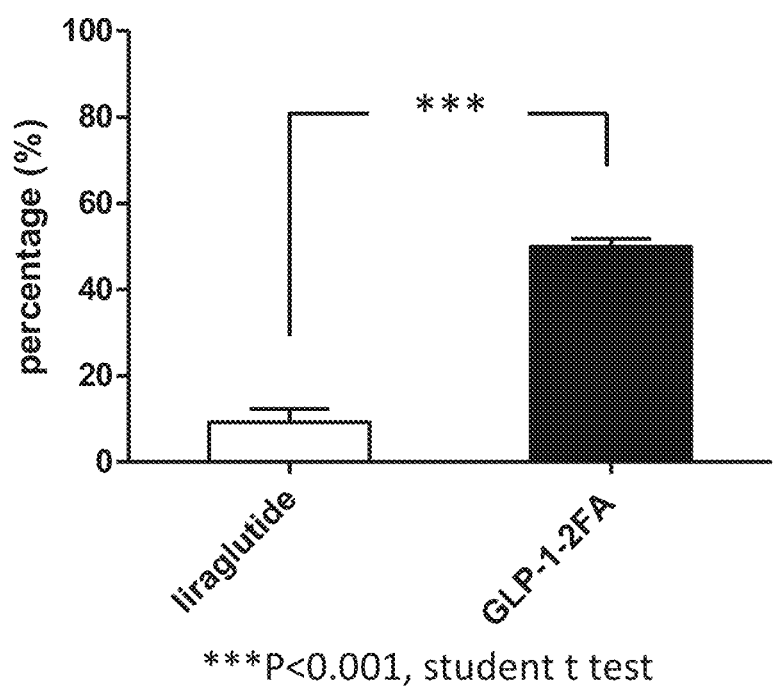

It was found that GLP-1-2FA agonist exhibited a higher binding ability to HSA than liraglutide in aqueous solution (FIG. 16A). Arrow #1 was HSA-bound liraglutide; Arrow #2 was HSA-bound GLP-1-2FA agonist; Arrow #3 was HSA. The percentage of the HSA-bound GLP-1-2FA agonist or liraglutide at equilibrium on SDS-PAGE is illustrated FIG. 16B. Data were presented as mean±SEM of triplicate samples.

Example 18: Functional Assay of GLP-1 Analogues on GLP-1R-Mediated-cAMP Generation in Rat INS-1 Cells It is well known that cyclic AMP (cAMP) is produced in cells in response to incretins released by the intestine in response to food intake. The hormone peptide GLP-1 increases cAMP levels by activating a specific G protein-coupled receptor, GLP-1 receptor, resulting in stimulation of one of a family of G protein-responsive, transmembrane adenylyl cyclases.

In this example, to evaluate the functional activities of these GLP-1 analogues to GLP-1 receptor on β cells, cAMP assay was performed in INS-1 cells.

A cAMP ELISA Kit (Cayman Chemicals, Ann Arbor, USA) was used to measure changes in intracellular cAMP induced by five GLP-1 analogues, GLP-1-Ala$^8$-EG$_4$-2E-2FA-C16, GLP-1-Aib$^8$-EG$_4$-2E-2FA-C16, GLP-1-Aib$^8$-EG$_4$-2E-2FA-C16-acid, GLP-1-Aib$^8$-EG$_2$-2E-2FA-C16-acid, and GLP-1-Aib$^8$-EG$_2$-2E-2FA-C18-acid agonists according to manufacturing's instructions. Briefly, on day one, 2×10$^5$ INS-1 cells were plated in each well of a 24-well plate (ThermoFisher Scientific, Waltham, USA) with 500 μL/well culture medium. On day three, our GLP-1 analogues in concentration of 100 nM were added to the wells with 2.5 mM glucose and incubated for 20 min at 37° C. 100 nM liraglutide, as a positive control for cAMP generation, was added to control wells and incubated for 20 min at 37° C. Glucose at lower concentration (2.5 mM) was used as a negative control, and glucose at higher concentration (16 mM) was used as a control for glucose-induced cAMP generation. After 20 minutes of incubation, the medium was aspirated and 200 μl of 0.1N HCl was added to each well. The cells were scraped off from the surface by cell scraper and subjected to centrifugation at 1,000×g for 10 min at 4° C. The supernatant was transferred to new tubes and used for experiment in a 96-well plate. Cyclic AMP levels in the cells were measured at wavelength of 420 nm using SpectraMax M2 microplate reader (Molecular devices, San Jose, USA).

Figure 17:
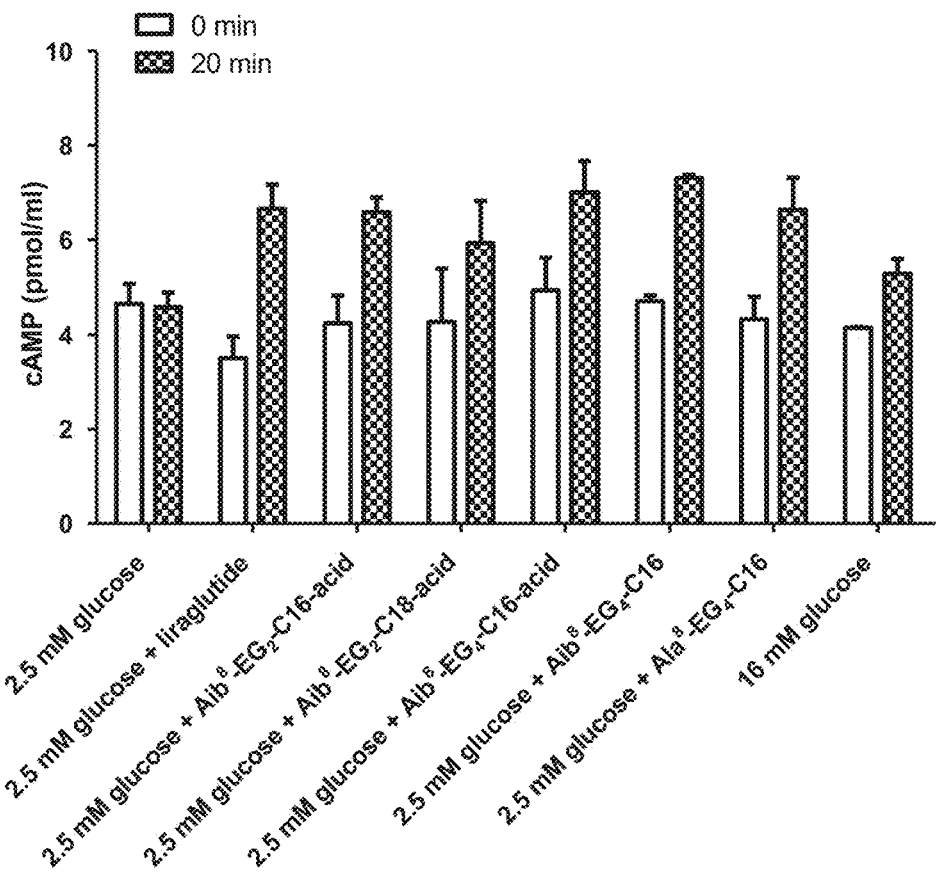
FIG. 17 shows the cAMP measurement of INS-1 cells incubated with synthesized GLP-1 analogues, according to one example of the present disclosure.

FIG. 17 shows the cAMP measurement of INS-1 cells upon the incubation with five GLP-1 analogues, GLP-1-Ala$^8$-EG$_4$-2E-2FA-C16 (abbreviated as Ala$^8$-EG$_4$-C16), GLP-1-Aib$^8$-EG$_4$-2E-2FA-C16 (abbreviated as Aib$^8$-EG$_4$-C16), GLP-1-Aib$^8$-EG$_4$-2E-2FA-C16-acid (abbreviated as Aib$^8$-EG$_4$-C16-acid), GLP-1-Aib$^8$-EG$_2$-2E-2FA-C16-acid (abbreviated as Aib$^8$-EG$_2$-C16-acid), and GLP-1-Aib$^8$-EG$_2$-2E-2FA-C18-acid (abbreviated as Aib$^8$-EG$_2$-C18-acid) agonists. The result indicated that additions of these synthesized GLP-1 analogues and liraglutide to INS-1 cells elicited the expected rise in cellular cAMP level observed at the time point measured (20 min).

Example 19: Western Blot Analysis for the Detection of the Expression of Activated Caspase-3 in INS-1 Cells Cleaved caspase-3 is a key executor in the apoptotic process. In this example, the expression of caspase-3 was detected using western blot analysis.

INS-1 cells treated with GLP-1 analogues were cultured with xx mM glucose and 500 μl. culture medium per well. For the immunoblot analysis, proteins were separated using SDS-PAGE, and then transferred onto a polyvinylidene fluoride (PVDF) membrane. The membrane was probed using antibodies against caspase-3 (Cell Signaling Technology, Danvers, USA), followed by horseradish peroxidase-(HRP) conjugated secondary antibodies (Epitomics, Burlingame, USA). The membrane was visualized using an enhanced chemiluminescence system (GE Healthcare Life Sciences, Buckinghamshire, USA). The levels of protein expression were normalized against β-actin expression.

Figure 18A:
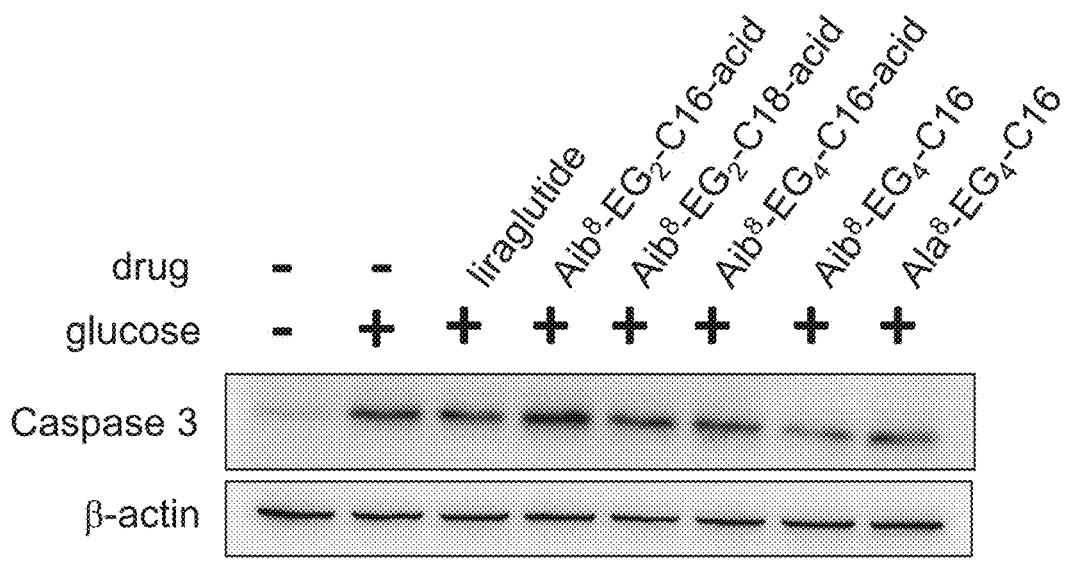
FIGS. 18A and 18B show the result of inhibition assay of synthesized GLP-1 analogues on the expression of activated caspase-3 in INS-1 cells, according to one example of the present disclosure.
Figure 18B:
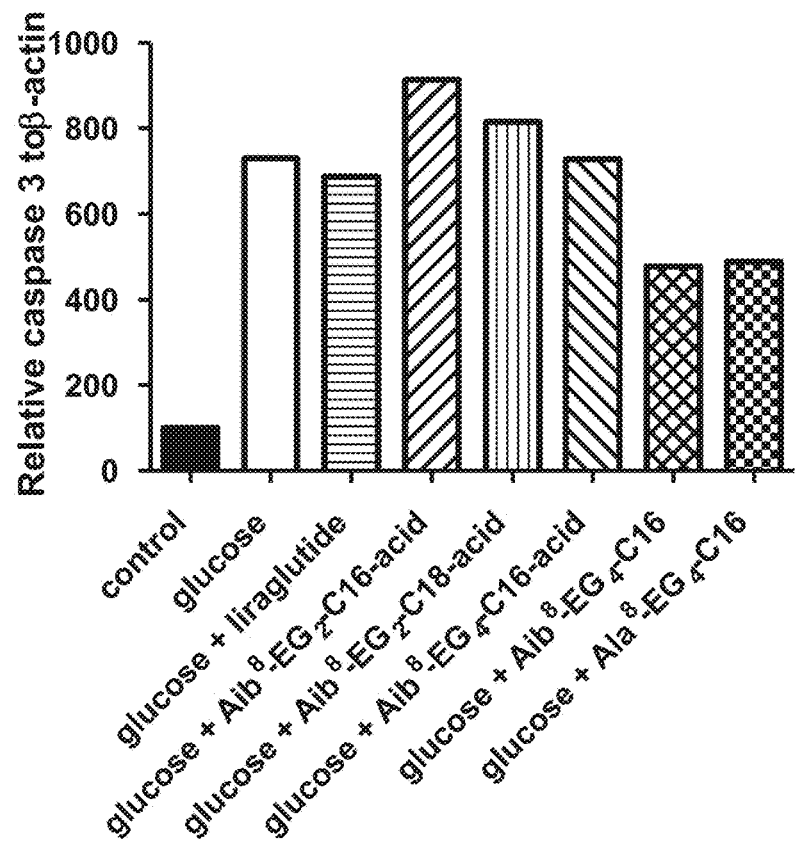

The results summarized in FIG. 18A show that the expression level of caspase-3 treated with GLP-1 analogues. FIG. 18B shows the degree of reduced expression level of caspase-3 on INS-1 cells upon the incubation with GLP-1 analogues. The results of FIGS. 18A and 18B indicated that some of GLP-1 analogues, including GLP-1-Aib$^8$-EG$_4$-2E-2FA-C16 (Aib$^8$-EG$_4$-C16) and GLP-1-Ala$^8$-EG$_4$-2E-2FA-C16 (Ala$^8$-EG$_4$-C16), can effectively reduce the expression level of caspase-3 in INS-1 cells.

Example 20: Alamar Blue Assay for the Determination of Cell Viability of INS-1 Cells The cultured INS-1 cells were seeded at a density of 2×10$^4$ cells/well into 96-well plate in culture medium containing 10% fecal bovine serum. After 48 hours, the cells were further incubated for another 24 hours for serum starvation. When the cells in synchronization state, the cells cultured in medium with 30 mM glucose and treated with 100 nM GLP-1 analogues or liraglutide. The cells cultured in normal medium being used as a control.

After being incubated for 24, 48 and 72 hours, the cell viability was then determined by Alamar Blue cell viability reagent kit (Invitrogen) in accordance with the manufacturer's instruction.

Figure 19:
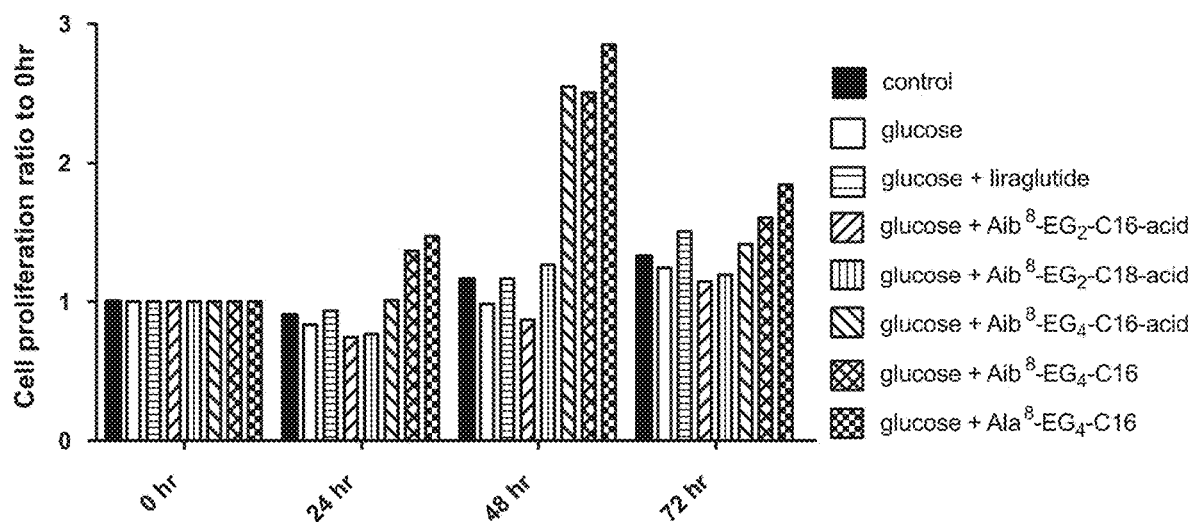
FIG. 19 shows the results of proliferation assay of INS-1 cells incubated with synthesized GLP-1 analogues, according to one example of the present disclosure.

The cell proliferation ratio (see FIG. 19) was a ratio of the cell viability at multiple time points compared to 0 hour. The result indicated that the cell viabilities were significantly improved by some of GLP-1 analogues, including GLP-1-Aib$^8$-EG$_4$-2E-2FA-C16-acid (Aib$^8$-EG$_4$-C16-acid), GLP-1-Aib$^8$-EG$_4$-2E-2FA-C16 (Aib$^8$-EG$_4$-C16) and GLP-1-Ala$^8$-EG$_4$-2E-2FA-C16 (Ala$^8$-EG$_4$-C16), compared with liraglutide.

Example 21: In Vivo Assay of GLP-1 Analogues on Reduction of Blood Glucose Concentration in Type II Diabetic Db/Db Mice 8-week-old BKS.Cg-+Lepr$^{db}$/+Lepr$^{db}$/(db/db) were purchased from National Laboratory Animal Center (NAR-Labs) in Taiwan. They were housed four animals per cage in all experiments under controlled ambient conditions. Animal were given free accessed to drinking water and conventional food.

For preliminary testing of blood glucose measurement in db/db mice treated with GLP-1 analogues, a pretest procedure was performed. Mice were grouped into three mice per group with the respective samples at a concentration of 100 nmole per kg. Mice received the single subcutaneous injections of GLP-1 analogues, liraglutide or vehicle (PBS).

For the measurement of blood glucose, blood samples were collected from the tail vein and blood glucose were measured immediately using commercially available enzyme electrode method (ACCU-CHEK Active, Roche, Germany). The result of preliminary testing indicated that the level of blood glucose in db/db mice treated with GLP-1 analogues can be significantly reduced by some of these GLP-1 analogues across 96 hours, compared with the mice treated with liraglutide.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A linker unit, comprising a center core and 2 to 5 first elements, wherein each of the first elements is independently a $C_{8-28}$ fatty acid derivative or a $C_{8-28}$ dioic fatty acid derivative, and the center core comprises, 2 to 5 lysine (K) residues, wherein the ε-amino group of each of the K residues of the center core is acylated with one of the first elements;

optionally, one or more fillers, wherein any two of the K residues are adjacent to each other or are separated by the filler;

optionally, a terminal spacer, wherein the terminal spacers is an N-terminal spacer linked to the N-terminus of the first K residue or a C-terminal spacer linked to the C-terminus of the last K residue, and each of the filler and the terminal spacer comprises, independently, (1) 1 to 12 non-K amino acid residues, or (2) a PEGylated amino acid having 1 to 12 repeats of ethylene glycol (EG) unit; and a conjugating moiety, linked to the terminal K residue or, in the case where the terminal spacer is present, the terminal amino acid residue of the terminal spacer by forming an amide bond therewith, wherein the conjugating moiety has a conjugating group selected from the group consisting of azide, alkyne, tetrazine, cyclooctene, and cyclooctyne group.

2. The linker unit of claim 1, wherein the fatty acid derivative is derived from octanoic acid, pelargonic acid, decanoic acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, palmitoleic acid, oleic acid, lionleic acid, ricinoleic acid, vaccenic acid, eicosapentaenoic acid (EPA), or docosahexaenoic acid (DHA).

3. The linker unit of claim 2, wherein the fatty acid is derived from myristic acid or palmitic acid.

4. The linker unit of claim 1, wherein the dioic fatty acid derivative is derived from suberic acid, azelaic acid, sebacic acid, undecanedioic acid, dodecanedioic acid, brassylic acid, tetradecanedioic acid, pentadecanedioic acid, thapsic acid, heptadecanedioic acid, or octadecanedioic acid.

5. The linker unit of claim 4, wherein the dioic fatty acid derived is derivable from tetradecanedioic acid or thapsic acid.

6. The linker unit of claim 1, wherein the fatty acid derivative or the dioic fatty acid derivative is modified with a glutamate residue.

7. The linker unit of claim 1, further comprising a second element that is linked to the conjugating group via copper catalyzed azide-alkyne cycloaddition (CuAAC) reaction, strained-promoted azide-alkyne click chemistry (SPAAC) reaction, or inverse electron demand Diels-Alder (iEDDA) reaction.

8. The linker unit of claim 7, wherein the second element is selected from the group consisting of, insulin, insulin-like growth factor, glucagon-like peptide-1 agonist, somatostatin and somatostatin analogues, calcitonin, growth hormone, erythropoietin, gonadotropin releasing factor, granulocyte colony stimulating factor, adenosine deaminase, arginine deiminase, asparaginase, interferon-α, interferon-β, soluble TNF-α receptor, soluble IL-1 receptor, soluble EGF receptor, agalsidase β, agalsidase α, laronidase, idursulphase, alglucosidase α, and galsulphase, or a derivative or variant thereof.

9. The linker unit of claim 8, wherein the somatostatin analogue is octreotide.

10. The linker unit of claim 7, wherein the second element is a drug bundle comprising a plurality of drug molecules.

11. The linker unit of claim 1, wherein the cyclooctene group is norbornene or trans-cyclooctene (TCO); and the cyclooctyne group is dibenzocyclooctyne (DBCO or DIBO), difluorinated cyclooctyne (DIFO), bicyclononyne (BCN), or dibenzoazacyclooctyne (DIBAC).

12. The linker unit of claim 1, wherein the tetrazine group is 1,2,3,4-tetrazine, 1,2,3,5-tetrazine or 1,2,4,5-tetrazine, or derivatives thereof.

13. The linker unit of claim 1, wherein the azide group is a picolyl azide group.

14. The linker unit of claim 1, wherein the center core comprises both the N-terminal spacer and the C-terminal spacer, and when the conjugating group of the N-terminal spacer is azide, alkyne, or cyclooctyne group; the conjugating group of the C-terminal spacer is tetrazine or cyclooctene group; or when the conjugating group of the N-terminal spacer is tetrazine or cyclooctene group, the conjugating group of the C-terminal spacer is azide, alkyne, or cyclooctyne group.

15. The linker unit of claim 14, further comprising a second element and a third element, wherein, the second element is linked to the conjugating group of the N-terminal spacer via CuAAC reaction or SPAAC reaction, and the third element is linked to the conjugating group of the C-terminal spacer via iEDDA reaction; or the second element is linked to the conjugating group of the N-terminal spacer via iEDDA reaction, and the third element is linked to the conjugating group of the C-terminal spacer via CuAAC reaction or SPAAC reaction.

* * * * *